un009763956B2

United States Patent
Bernstein et al.

(10) Patent No.: US 9,763,956 B2
(45) Date of Patent: Sep. 19, 2017

(54) DIAGNOSTIC AND TREATMENT METHODS IN SUBJECTS HAVING OR AT RISK OF DEVELOPING RESISTANCE TO CANCER THERAPY

(71) Applicants: The Broad Institute, Inc., Cambridge, MA (US); The Brigham and Women's Hospital, Inc., Boston, MA (US); The General Hospital Corporation, Boston, MA (US); Dana-Farber Cancer Institute, Inc., Boston, MA (US)

(72) Inventors: Bradley E. Bernstein, Cambridge, MA (US); Jon C. Aster, Lexington, MA (US); James E. Bradner, Weston, MA (US); Birgit Knoechel, Brookline, MA (US); Christopher J. Ott, Cambridge, MA (US); David Root, Brookline, MA (US)

(73) Assignees: The Broad Institute, Inc., Cambridge, MA (US); The Brigham and Women's Hospital, Inc., Boston, MA (US); The General Hospital Corporation, Boston, MA (US); Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/409,138

(22) PCT Filed: Jun. 19, 2013

(86) PCT No.: PCT/US2013/046485
§ 371 (c)(1),
(2) Date: Dec. 18, 2014

(87) PCT Pub. No.: WO2013/192274
PCT Pub. Date: Dec. 27, 2013

(65) Prior Publication Data
US 2015/0174138 A1 Jun. 25, 2015

Related U.S. Application Data

(60) Provisional application No. 61/780,665, filed on Mar. 13, 2013, provisional application No. 61/661,884, filed on Jun. 20, 2012, provisional application No. 61/661,772, filed on Jun. 19, 2012.

(51) Int. Cl.
*A61K 45/06* (2006.01)
*A61K 31/551* (2006.01)
*A61K 31/5517* (2006.01)
*A61K 31/55* (2006.01)
*A61K 31/713* (2006.01)
*C12N 15/113* (2010.01)

(52) U.S. Cl.
CPC ............ *A61K 31/551* (2013.01); *A61K 31/55* (2013.01); *A61K 31/5517* (2013.01); *A61K 31/713* (2013.01); *A61K 45/06* (2013.01); *C12N 15/113* (2013.01); *C12N 2310/14* (2013.01)

(58) Field of Classification Search
CPC .... A61K 31/551; A61K 31/713; A61K 45/06; C12N 15/113; C12N 2310/14
See application file for complete search history.

(56) References Cited

U.S. PATENT DOCUMENTS

2012/0028912 A1    2/2012   Zhou et al.

FOREIGN PATENT DOCUMENTS

| JP | 2008-156311 A | 7/2008 |
|---|---|---|
| JP | 2009-028043 A | 5/2009 |
| JP | 2009-183291 A | 8/2009 |
| WO | WO 2009/084693 A1 | 7/2009 |
| WO | WO 2011/054843 A1 | 5/2011 |
| WO | WO 2011/054844 A1 | 5/2011 |
| WO | WO 2011/054846 A1 | 5/2011 |
| WO | WO 2011/054848 A1 | 5/2011 |
| WO | WO 2011/054851 A1 | 5/2011 |
| WO | WO 2011/143651 A1 | 11/2011 |
| WO | WO 2011/143660 A2 | 11/2011 |
| WO | WO 2011/143669 A2 | 11/2011 |

OTHER PUBLICATIONS

Jayanthan et al. (Pediatric Blood and Cancer, Mar. 2011 56(3):353-360).*
Blobel et al., Short hairpin RNA screen reveals bromodomain proteins as novel targets in acute myeloid leukemia. Cancer Cell. Sep. 13, 2011;20(3):287-8. doi: 10.1016/j.ccr.2011.08.019.
Bolós et al., Notch signaling in development and cancer. Endocr Rev. May 2007;28(3):339-63. Epub Apr. 4, 2007.
Chan et al., Notch signals positively regulate activity of the mTOR pathway in T-cell acute lymphoblastic leukemia. Blood. Jul. 1, 2007;110(1):278-86. Epub Mar. 15, 2007.
Chung et al., Discovery and characterization of small molecule inhibitors of the BET family bromodomains. J Med Chem. Jun. 9, 2011;54(11):3827-38. doi: 10.1021/jm200108t. Epub May 13, 2011.
Chung et al., Progress in the discovery of small-molecule inhibitors of bromodomain—histone interactions. J Biomol Screen. Dec. 2011;16(10):1170-85. doi: 10.1177/1087057111421372. Epub Sep. 28, 2011.
Dawson et al., Cancer epigenetics: from mechanism to therapy. Cell. Jul. 6, 2012;150(1):12-27. doi: 10.1016/j.cell.2012.06.013.
Dawson et al., Inhibition of BET recruitment to chromatin as an effective treatment for MLL-fusion leukaemia. Nature. Oct. 2, 2011;478(7370):529-33. doi: 10.1038/nature10509.
(Continued)

*Primary Examiner* — J. E. Angell
(74) *Attorney, Agent, or Firm* — Wolf, Greenfield & Sacks, P.C.

(57) ABSTRACT

The invention relates to methods of treatment and diagnosis of subjects with cancer. In some aspects, the invention relates to methods of treatment and diagnosis of subjects with cancer, wherein the cancer is characterized by a Notch pathway activation mutation or by resistance to a Notch pathway inhibitor.

12 Claims, 26 Drawing Sheets

(56) References Cited

OTHER PUBLICATIONS

Dunham et al., An integrated encyclopedia of DNA elements in the human genome. Nature. Sep. 6, 2012;489(7414):57-74. doi: 10.1038/nature11247.

Filippakopoulos et al., Benzodiazepines and benzotriazepines as protein interaction inhibitors targeting bromodomains of the BET family. Bioorg Med Chem. Mar. 15, 2012;20(6):1878-86. doi: 10.1016/j.bmc.2011.10.080. Epub Nov. 4, 2011.

Guruharsha et al., The Notch signalling system: recent insights into the complexity of a conserved pathway. Nat Rev Genet. Sep. 2012;13(9):654-66. doi: 10.1038/nrg3272. Epub Aug. 7, 2012.

Gutierrez et al., High frequency of PTEN, PI3K, and AKT abnormalities in T-cell acute lymphoblastic leukemia. Blood. Jul. 16, 2009;114(3):647-50. doi: 10.1182/blood-2009-02-206722. Epub May 20, 2009.

Haber et al., The evolving war on cancer. Cell. Apr. 1, 2011;145(1):19-24. doi: 10.1016/j.cell.2011.03.026.

Kalaitzidis et al., mTOR complex 1 plays critical roles in hematopoiesis and Pten-loss-evoked leukemogenesis. Cell Stem Cell. Sep. 7, 2012;11(3):429-39. doi: 10.1016/j.stem.2012.06.009.

Lu et al., Metabolic regulation of epigenetics. Cell Metab. Jul. 3, 2012;16(1):9-17. doi: 10.1016/j.cmet.2012.06.001.

Nicodeme et al., Suppression of inflammation by a synthetic histone mimic. Nature. Dec. 23, 2010;468(7327):1119-23. doi: 10.1038/nature09589. Epub Nov. 10, 2010.

Palomero et al., Mutational loss of PTEN induces resistance to NOTCH1 inhibition in T-cell leukemia. Nat Med. Oct. 2007;13(10):1203-10. Epub Sep. 16, 2007.

Palomero et al., NOTCH1 directly regulates c-MYC and activates a feed-forward-loop transcriptional network promoting leukemic cell growth. Proc Natl Acad Sci U S A. Nov. 28, 2006;103(48):18261-6. Epub Nov. 17, 2006.

Palomero et al., Therapeutic targeting of NOTCH1 signaling in T-cell acute lymphoblastic leukemia. Clin Lymphoma Myeloma. 2009;9 Suppl 3:S205-10. doi: 10.3816/CLM.2009.s.013.

Sethi et al., Notch signaling in cancer progression and bone metastasis. Br J Cancer. Dec. 6, 2011;105(12):1805-10. doi: 10.1038/bjc.2011.497. Epub Nov. 10, 2011.

Sharma et al., A chromatin-mediated reversible drug-tolerant state in cancer cell subpopulations. Cell. Apr. 2, 2010;141(1):69-80. doi: 10.1016/j.cell.2010.02.027.

Tang et al., Pyrogallol-based molecules as potent inhibitors of the antiapoptotic Bcl-2 proteins. J Med Chem. Apr. 19, 2007;50(8):1723-6. Epub Mar. 23, 2007.

Weng et al., c-Myc is an important direct target of Notch1 in T-cell acute lymphoblastic leukemia/lymphoma. Genes Dev. Aug. 1, 2006;20(15):2096-109. Epub Jul. 17, 2006.

Zhao et al., Gene bookmarking accelerates the kinetics of post-mitotic transcriptional reactivation. Nat Cell Biol. Oct. 9, 2011;13(11):1295-304. doi: 10.1038/ncb2341.

Zhou et al., Charting histone modifications and the functional organization of mammalian genomes. Nat Rev Genet. Jan. 2011;12(1):7-18. doi: 10.1038/nrg2905. Epub Nov. 30, 2010.

Zuber et al., RNAi screen identifies Brd4 as a therapeutic target in acute myeloid leukaemia. Nature. Aug. 3, 2011;478(7370):524-8. doi: 10.1038/nature10334.

Invitation to Pay Additional Fees and Partial Search Report mailed Aug. 27, 2013 for Application No. PCT/US2013/046485.

International Search Report and Written Opinion mailed Jan. 23, 2014 for Application No. PCT/US2013/046485.

International Preliminary Report on Patentability mailed Dec. 31, 2014 for Application No. PCT/US2013/046485.

Chesi et al., Drug response in a genetically engineered mouse model of multiple myeloma is predictive of clinical efficacy. Blood. Jul. 12, 2012;120(2):376-85. doi: 10.1182/blood-2012-02-412783. Epub Mar. 26, 2012. 36 pages.

Da Costa et al., 77 Inhibition of BRD4 Bromodomains Is a Potent Novel Strategy to Target Apoptosis Resistance in Paediatric ALL. Blood. Dec. 11, 2011; XP055075511. https://ash.confex.com/ash/2011/webprogram/Paper37948.html [Last accessed Oct. 16, 2013]. Abstract.

Filippakopoulos et al., Selective inhibition of BET bromodomains. Nature. Dec. 23, 2010;468(7327):1067-73. doi: 10.1038/nature09504. Epub Sep. 24, 2010.

Knoechel et al., An epigenetic mechanism of resistance to targeted therapy in T cell acute lymphoblastic leukemia. Nat Genet. Apr. 2014;46(4):364-70. doi: 10.1038/ng.2913. Epub Oct. 1, 2014. 21 pages.

Kotz, BET-ting on bromodomains. J SciBX. 2010;3(41). doi:10.1038/scibx.2010.1224. Epub Oct. 21, 2010. 2 pages.

Li et al., Combined inhibition of Notch signaling and Bcl-2/Bcl-xL results in synergistic antimyeloma effect. Mol Cancer Ther. Dec. 2010;9(12):3200-9. doi: 10.1158/1535-7163.MCT-10-0372.

MacKeen et al., Small-molecule-based inhibition of histone demethylation in cells assessed by quantitative mass spectrometry. J Proteome Res. Aug. 6, 2010;9(8):4082-92. doi: 10.1021/pr100269b.

Moellering et al, Direct inhibition of the NOTCH transcription factor complex. Nature. Nov. 12, 2009;462(7270):182-8. doi: 10.1038/nature08543. Epub Oct. 7, 2010. 16 pages.

Muller et al., Bromodomains as therapeutic targets. Expert Rev Mol Med. Sep. 13, 2011;13:e29. doi: 10.1017/S1462399411001992. Review. 21 pages.

Rao et al., Inhibition of NOTCH Signaling by Gamma Secretase Inhibitor Engages the RB Pathway and Elicits Cell Cycle Exit in T-Cell Acute Lymphoblastic Leukemia Cells. Cancer Res. Apr. 1, 2009;69(7):3060-8.

Sack et al, Structural basis for CARM1 inhibition by indole and pyrazole inhibitors. Biochem J. Jun. 1, 2011;436(2):331-9. doi: 10.1042/BJ20102161.

Selvi et al, Identification of a novel inhibitor of coactivator-associated arginine methyltransferase 1 (CARM1)-mediated methylation of histone H3 Arg-17. J Biol Chem. Mar. 5, 2010;285(10):7143-52. doi: 10.1074/jbc.M109.063933. Epub Dec. 17, 2009.

Séveno et al., γ-Secretase inhibition promotes cell death, Noxa upregulation, and sensitization to BH3 mimetic ABT-737 in human breast cancer cells. Breast Cancer Res. 2012;14:R96. 15 pages.

Wang et al., TW-37, a Small-Molecule Inhibitor of Bcl-2, Inhibits Cell Growth and Induces Apoptosis in Pancreatic Cancer: Involvement of Notch-1 Signaling Pathway. Cancer Res. 2009;69:2757-65.

Wu et al., Therapeutic antibody targeting of individual Notch receptors. Nature. Apr. 15, 2010;464(7291):1052-7. doi: 10.1038/nature08878.

PCT/US2013/046485, Aug. 27, 2013, Invitation to Pay Additional Fees and Partial Search Report.

PCT/US2013/046485, Jan. 23, 2014, International Search Report and Written Opionion.

PCT/US2013/046485, Dec. 31, 2014, International Preliminary Report on Patentability.

\* cited by examiner

N – Naïve
ST – short-term treated
R – Resistant

Partial MNase digestion

Time (minutes)

N – Naïve
R – Resistant

Global levels of repressive chromatin marks

| Motifs enriched at distal BRD4 sites | Related motif | p-value | % of targets |
|---|---|---|---|
| ₐcTTCCTgᵧ | ERG/ETS | 1E-92 | 43.2% |
| AAACCACA | Runx1 | 1E-48 | 22.3% |

Fig. 16A

DIAGNOSTIC AND TREATMENT METHODS IN SUBJECTS HAVING OR AT RISK OF DEVELOPING RESISTANCE TO CANCER THERAPY

CROSS-REFERENCE TO RELATED APPLICATIONS

This application is a national stage filing under 35 U.S.C. §371 of International Application No. PCT/US2013/046485, filed Jun. 19, 2013, which was published under PCT Article 21(2) in English and which claims the benefit of U.S. Provisional Application No. 61/661,772, filed Jun. 19, 2012, U.S. Provisional Application No. 61/661,884, filed Jun. 20, 2012, and U.S. Provisional Application No. 61/780,665, filed Mar. 13, 2013. The entire contents of each of these referenced applications are incorporated by reference herein.

GOVERNMENT SUPPORT

This invention was made with government support under 5U01ES017155 awarded by the National Institutes of Health. The Government has certain rights in the invention.

FIELD OF INVENTION

The invention relates to treatment of certain cancers, including cancers that are resistant to the standard of care, and to methods of diagnosing the resistance phenotype.

BACKGROUND OF INVENTION

T-cell acute lymphoblastic leukemia (T-ALL) is a devastating form of cancer characterized by malignant, immature white blood cells that continuously multiply and are overproduced in the bone marrow. T-ALL leads to pain and damage throughout the body and eventually death due to the crowding out of normal cells in the bone marrow and the spreading of tumor cells to other organs. 50% of T-ALL cases harbor a mutation in the Notch signaling pathway. As a result, gamma secretase inhibitors (GSI) that inhibit cleavage of the activated form of Notch have been developed. Unfortunately, early relapse and refractory disease are common in T-ALL cases due to the transient response of the cancer to a GSI. Additionally, GSI treatment is also associated with toxicity, especially damage to the gastrointestinal tract.

SUMMARY OF INVENTION

The invention provides new therapies to treat certain cancers, including those having Notch pathway activation mutations, those having observed resistance to Notch inhibitors, and those likely to manifest resistance to Notch inhibitors. The invention also provides methods for identifying subjects to be treated with the new therapies provided herein.

Thus, in one aspect, the invention provides a method comprising administering to a subject having cancer (i) a bromodomain inhibitor and/or (ii) a Bcl-2 inhibitor, and a Notch pathway inhibitor, in an effective amount to treat the cancer.

In some embodiments, the cancer is resistant to a previously-administered Notch pathway inhibitor. In some embodiments, the cancer is characterized by the presence of a Notch pathway activation mutation. In some embodiments, the cancer is characterized by abnormal increased HPI-alpha, HPI-beta, and/or HPI-gamma level. In some embodiments, the cancer is characterized by a chromatin compactness or a marker thereof.

In some embodiments, the bromodomain inhibitor and the Notch pathway inhibitor are administered concurrently or sequentially. In some embodiments, the Bcl-2 inhibitor and the Notch pathway inhibitor are administered concurrently or sequentially. In some embodiments, the bromodomain inhibitor, the Bcl-2 inhibitor and the Notch pathway inhibitor are administered. In some embodiments, the bromodomain inhibitor, the Bcl-2 inhibitor and the Notch pathway inhibitor are administered concurrently or sequentially.

In another aspect, the invention provides a method comprising: administering to a subject having cancer (i) a bromodomain inhibitor and/or (ii) a Bcl-2 inhibitor, in an effective amount to treat the cancer, wherein the cancer is characterized by the presence of a Notch pathway activation mutation.

In some embodiments, the method further comprises identifying the subject having cancer characterized by the presence of a Notch pathway activation mutation. In some embodiments, the method further comprises administering to the subject a Notch pathway inhibitor in an effective amount to treat the cancer.

In some embodiments, the bromodomain inhibitor and the Notch pathway inhibitor are administered concurrently or sequentially. In some embodiments, the Bcl-2 inhibitor and the Notch pathway inhibitor are administered concurrently or sequentially. In some embodiments, the bromodomain inhibitor, the Bcl-2 inhibitor, and the Notch pathway inhibitor are administered. In some embodiments, the bromodomain inhibitor, the Bcl-2 inhibitor, and the Notch pathway inhibitor are administered concurrently or sequentially.

In another aspect, the invention provides a method comprising: administering to a subject having cancer (i) a bromodomain inhibitor and/or (ii) a Bcl-2 inhibitor in an effective amount to treat the cancer, wherein the cancer is resistant to treatment with a Notch pathway inhibitor.

In some embodiments, the method further comprises administering to the subject a Notch pathway inhibitor in an effective amount to treat the cancer. In some embodiments, the bromodomain inhibitor and the Notch pathway inhibitor are administered concurrently or sequentially. In some embodiments, the Bcl-2 inhibitor and the Notch pathway inhibitor are administered concurrently or sequentially. In some embodiments, the bromodomain inhibitor, the Bcl-2 inhibitor, and the Notch pathway inhibitor are administered. In some embodiments, the bromodomain inhibitor, the Bcl-2 inhibitor, and the Notch pathway inhibitor are administered concurrently or sequentially.

In another aspect, the invention provides a method comprising: administering to a subject having cancer (i) a bromodomain inhibitor and/or (ii) a Bcl-2 inhibitor in an effective amount to treat the cancer, wherein the cancer is characterized by abnormal increased HPI level, wherein the HPI level is HPI-alpha level, HPI-beta level and/or HPI-gamma level.

In some embodiments, the method further comprises identifying a subject having cancer characterized by the abnormal increased HPI level. In some embodiments, the method further comprises administering to the subject a Notch pathway inhibitor in an effective amount to treat the cancer.

In some embodiments, the bromodomain inhibitor and the Notch pathway inhibitor are administered concurrently or sequentially. In some embodiments, the Bcl-2 inhibitor and the Notch pathway inhibitor are administered concurrently or sequentially. In some embodiments, the bromodomain inhibitor, the Bcl-2 inhibitor, and the Notch pathway inhibitor are administered. In some embodiments, the bromodomain inhibitor, the Bcl-2 inhibitor and the Notch pathway inhibitor are administered concurrently or sequentially.

In embodiments of any of the aspects of the invention, the bromodomain inhibitor, the Bcl-2 inhibitor and/or the Notch pathway inhibitor is a small compound or inhibitory nucleic acid molecule. In some embodiments, the inhibitory nucleic acid molecule is an siRNA, shRNA, or antisense nucleic acid molecule. In some embodiments, the bromodomain inhibitor is a BET inhibitor. In some embodiments, the bromodomain inhibitor is JQ1 or a derivative thereof including those compounds described in WO 2011/143660. In some embodiments, the Bcl-2 inhibitor is G3139, GX15-070, ABT-737 or ABT-199, or a derivative thereof. In some embodiments, the Notch pathway inhibitor is a gamma secretase inhibitor.

In another aspect, the invention provides a method comprising: administering to a subject having cancer an inhibitor of ARID3B, EZH2, PRMT2, SND1, BRD1, SUV39H1, PRMT5, SS18, BRD4, KDM5D, PRMT7, STAG3L1, CD2BP2, MLL5, SUDS3, CHD1, MINA, CHD8, MORF4L1, or CHRAC1, wherein the cancer is resistant to a Notch pathway inhibitor.

In some embodiments, the method further comprises administering to the subject a Notch pathway inhibitor. In some embodiments, the method further comprises administering to the subject a bromodomain inhibitor and/or a Bcl-2 inhibitor in an effective amount to treat the cancer. In some embodiments, the inhibitor is an shRNA, an siRNA, or an antisense nucleic acid molecule.

In another aspect, the invention provides a method comprising: (a) measuring nucleus size in a tumor sample from a subject; and (b) comparing nucleus size in the tumor sample to a control, wherein a decreased nucleus size in the tumor sample compared to the control identifies a subject to be treated with a bromodomain inhibitor and/or Bcl-2 inhibitor. In some embodiments, the nucleus size is nucleus diameter or nucleus volume.

In another aspect, the invention provides a method comprising: (a) measuring HPI level in a tumor sample from a subject; and (b) comparing the HPI level in the tumor sample to a control, wherein an increased HPI level in the tumor sample compared to the control identifies a subject to be treated with a bromodomain inhibitor and/or Bcl-2 inhibitor, wherein the HPI level is HPI-alpha level, HPI-beta level, and/or HPI-gamma level.

In another aspect, the invention provides a method comprising: (a) measuring level of a chromatin state biomarker (CSB) in a tumor sample from a subject, the CSB selected from: (i) a first CSB group consisting of NPM1, NARG1, RCC1, SSRP1, PRMT3, SAP30, CBX6, CHMP2B, UBE2M, WDR77, HMGB1, CARM1, USP13, HDAC4, COQ3, SET, GATAD2A, PRMT6, HMG20B, DNMT1, ADA, SS18, UBE3A, ZMYND11, and NOC2LL ("Group I CSB"); and (ii) a second CSB group consisting of UTX, SIN3A, SAP30L, FLJ20309, RCOR2, ARID5A, UBE2Q2, TRIM24, BAZ2B, SMYD3, EZH2, PHF1, PHF2, BCR, SMARCD3, BMI1, CHD6, FBXL11, SIRT7, ASF1A, RCOR3, CBX4, EPC1, BRD1, and BNF11 ("Group II CSB"); (b) comparing the Group I and/or Group II CSB level with a control, wherein a Group I CSB level that is reduced in the tumor sample compared to a control and/or a Group II CSB level that is elevated in the tumor sample compared to a control identifies a subject to be treated with a bromodomain inhibitor and/or Bcl-2 inhibitor.

In another aspect, the invention provides a method comprising: (a) measuring a level of a biomarker in a tumor sample from a subject, the biomarker selected from DTX1, HES4, CD1d, ETS1, ETV6, Runx1, Bcl-2, MYC and CD52; and (b) comparing the biomarker level with a control, wherein a level of DTX1, HES4, or CD1d that is reduced in the tumor sample compared to the control and/or a level of ETS1, ETV6, Runx1, CD52, MYC or Bcl-2 that is elevated in the tumor sample compared to the control identifies a subject to be treated with a bromodomain inhibitor and/or Bcl-2 inhibitor.

In another aspect, the invention provides a method comprising: (a) measuring a level of histone modification in a tumor sample from a subject, the histone modification selected from H3K27me3 and H3K9me3; and (b) comparing the histone modification level with a control, wherein a level of histone modification that is elevated in the tumor sample compared to the control identifies a subject to be treated with a bromodomain inhibitor and/or Bcl-2 inhibitor.

In another aspect, the invention provides a method comprising: (a) measuring a level of H3K27Ac histone modification in a tumor sample from a subject; and (b) comparing the H3K27Ac histone modification level with a control, wherein a level of H3K27Ac histone modification that is reduced in the tumor sample compared to the control identifies a subject to be treated with a bromodomain inhibitor and/or Bcl-2 inhibitor.

In another aspect, the invention provides a method comprising: (a) measuring a level of H3K4me1 histone modification at a site of elevated H3K27Ac histone modification; and (b) comparing the H3K4me1 histone modification level with a control, wherein a level of H3K4me1 histone modification at a site of elevated H3K27Ac histone modification that is elevated in the tumor sample compared to the control identifies a subject to be treated with a bromodomain inhibitor and/or Bcl-2 inhibitor.

In some embodiments of the foregoing methods, the level is an mRNA level or a protein level. In some embodiments, the control is a nucleus size, an HPI-alpha level, an HPI-beta level, an HPI-gamma level, a CSB level, a histone modification level or a biomarker level selected from DTX1, HES4, CD1d, ETS1, ETV6, Runx1, Bcl-2, MYC and CD52 in a non-tumor sample. In some embodiments, the control is a predetermined threshold. In some embodiments, the methods further comprise identifying the subject to be treated with a bromodomain inhibitor and/or Bcl-2 inhibitor. In some embodiments, the methods further comprise administering to the identified subject a bromodomain inhibitor and/or Bcl-2 inhibitor in an effective amount. In some embodiments, the methods further comprise further comprising administering to the identified subject a Notch pathway inhibitor in an effective amount. In some embodiments, the cancer or tumor is a T-ALL. In some embodiments, the T-ALL is resistant to a Notch pathway inhibitor.

BRIEF DESCRIPTION OF DRAWINGS

FIG. 3 depicts cell and nucleus size changes in resistant leukemia cells compared to naïve leukemia cells.

FIG. 4 is an analysis of the chromatin state of naïve leukemia cells and resistant leukemia cells.

FIG. 5 depicts the chromatin compaction state in naïve and resistant leukemia cells.

FIG. 9 depicts the presence of BRD4 near the Bcl-2 gene.

FIG. 12 is an analysis of Notch signaling in naïve (N), short-term treated (ST, 5 days), persister (P), reversed (Rev) and re-treated (Rev tx) cells.

FIG. 16 shows that ETS and Runx transcription factors are targets of BRD4. FIG. 16A shows the motifs enriched at BRD4 binding sites.

Figure 1:
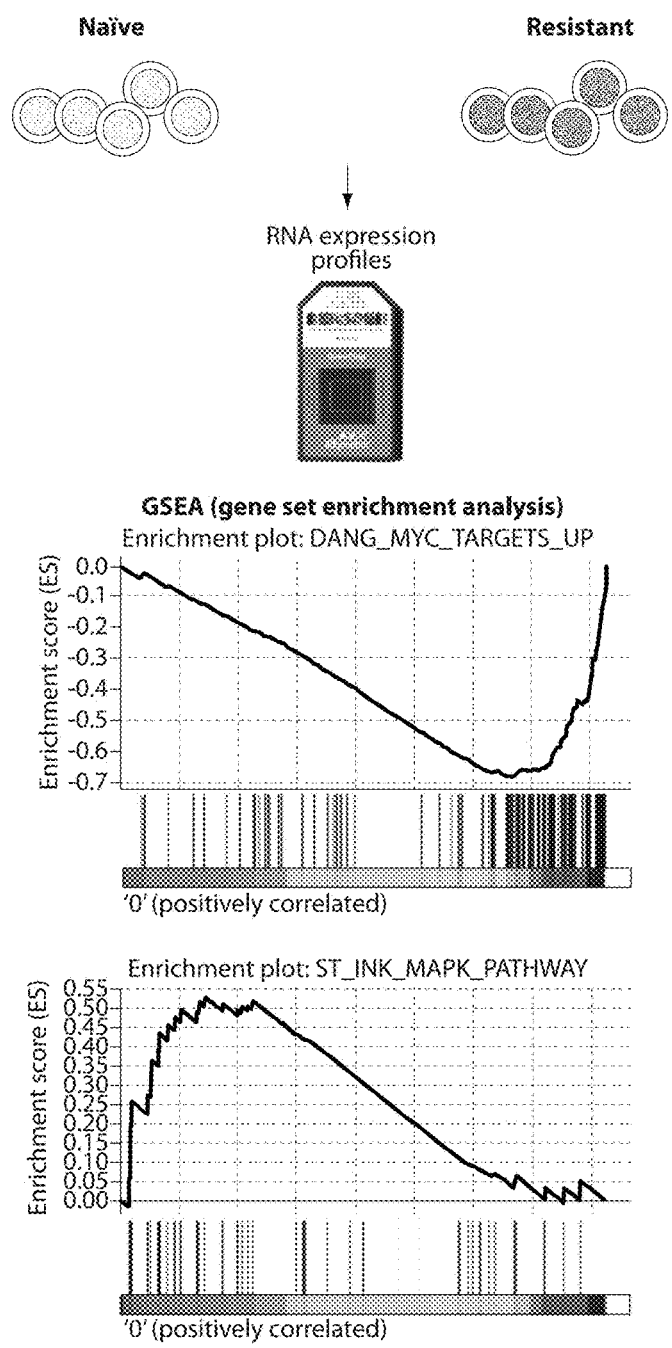
FIG. 1 is a line graph depicting Gene Set Enrichment Analysis (GSEA) for leukemia cells resistant to a gamma secretase inhibitor (GSI) and naïve leukemia cells (not treated with a GSI).

It is to be understood that the Figures are not required for enablement of the invention.

DETAILED DESCRIPTION OF INVENTION

The invention provides methods to diagnose and treat subjects using single or combination therapy. Certain methods of the invention relate to treatment of cancers that are resistant to therapy with a Notch pathway inhibitor or that are likely to become resistant to therapy with a Notch pathway inhibitor.

It has been found, in accordance with the invention, that a Notch inhibitor resistant phenotype (also referred to herein as a resister or persister phenotype) correlated with changes in chromatin structure of the cancer cells, resulting in more compact chromatin and smaller cell size, and with changes in expression of heterochromatin markers such as HPI-alpha, beta and gamma and various chromatin regulatory markers, such as histone modifications, or chromatin state biomarkers such as but not limited to BRD4. It was also found that changes in biomarkers selected from DTX1, HES4, CD1d, ETS1, ETV6, Runx1, Bcl-2, MYC and CD52 correlated with resistance to a Notch pathway inhibitor. Significantly, it has also been found, in accordance with the invention, that the resistance to the Notch pathway inhibitor could be reversed by using the Notch pathway inhibitor with a bromodomain inhibitor such as a BRD4 inhibitor. Without intending to be bound by any particular mechanism or theory, it is believed that the bromodomain inhibitor reverses the observed changes in chromatin structure, thereby reversing the resistance to the Notch pathway inhibitor. The invention further contemplates that a bromodomain inhibitor may be administered before resistance to a Notch pathway inhibitor is even manifest, thereby preventing the resistant phenotype from developing altogether or delaying its onset. The invention therefore contemplates treating subjects having certain cancers with a Notch pathway inhibitor and a bromodomain inhibitor. It has also been found, in accordance with the invention, that Notch pathway inhibitor resistant cells were sensitive to treatment with an mTOR or AKT inhibitor. The invention therefore contemplates treating subjects having certain cancers with a Notch pathway inhibitor and an mTOR and/or AKT inhibitor. The inhibitors may be administered before or after resistance to the Notch pathway inhibitor is observed. The cancers to be treated in this manner may be those that would be treated with a Notch pathway inhibitor, such as for example T-ALL, and those that are characterized by the presence of a Notch pathway activation mutation.

The invention further contemplates use of a bromodomain inhibitor alone or in combination with other anti-cancer agents in the treatment of cancers characterized by chromatin compaction or abnormal expression of chromatin regulatory markers or chromatin state biomarkers. Such cancers may manifest a reduced nucleus or cell size (or diameter) relative to normal, non-cancerous cells and/or they may have an increased expression level of HPI-alpha, beta and/or gamma mRNA and/or proteins relative to normal, non-cancerous cells, inter alia. In some embodiments, the cancer is (a) characterized by a compact nucleus or smaller cell size compared to a normal control, (b) characterized by abnormal increased (mRNA or protein) levels of HPI-alpha, beta and/or gamma, (c) characterized by abnormal increased (mRNA or protein) levels of certain chromatin regulatory proteins or chromatin state biomarkers such as but not limited to BRD4 and/or abnormal decreased (mRNA or protein) levels of other chromatin regulatory proteins or chromatin state biomarkers, (d) characterized by decreased expression of DTX1, HES4, and/or CD1d and/or by increased expression of ETS1, ETV6, Runx1, CD52, MYC or Bcl-2, (e) characterized by increased levels of repressive chromatin markers such as H3K27me3, or H3K9me2/3 and/or decreased levels of other chromatin markers such as H3K27Ac. and/or (f) characterized by resistance to a previously administered anti-cancer agent such as a Notch pathway inhibitor.

It has also been found, in accordance with the invention, that bromodomain inhibition, such as BRD4 inhibition, inhibits expression of Bcl-2, a known anti-apoptotic mediator. It is therefore contemplated by the invention that bromodomain inhibition may mediate its effects via Bcl-2 inhibition. This suggests that Bcl-2 inhibitors may be used instead of bromodomain inhibitors in certain methods of the invention, including those that involve combination therapy with a Notch pathway inhibitor.

In addition to treatment methods, the invention also provides methods of identifying subjects to be treated with bromodomain inhibitors alone or in combination with another anti-cancer such as but not limited to a Notch pathway inhibitor. Such subjects will be identified based on the presence of a cancer that is (a) characterized by the presence of a Notch pathway activation mutation, (b) characterized by a compact nucleus or smaller cell size compared to a normal control, (c) characterized by abnormal increased (mRNA or protein) levels of HPI-alpha, beta and/or gamma, (d) characterized by abnormal increased (mRNA or protein) levels of certain chromatin regulatory proteins or chromatin state biomarkers such as but not limited to BRD4 and/or abnormal decreased (mRNA or protein) levels of other chromatin regulatory proteins or chromatin state biomarkers, (e) characterized by decreased expression of DTX1, HES4, and/or CD1d and/or by increased expression of ETS1, ETV6, Runx1, CD52, MYC or Bcl-2, (f) characterized by increased levels of repressive chromatin markers such as H3K27me3, or H3K9me2/3 and/or decreased levels of other chromatin markers such as H3K27Ac. and/or (g) characterized by resistance to a previously administered anti-cancer agent such as a Notch pathway inhibitor.

In still other aspects, the invention provides methods for treating a subject having a cancer that is resistant to a Notch pathway inhibitor using inhibitors of a number of chromatin regulatory proteins such as ARID3B, EZH2, PRMT2, SND1, BRD1, SUV39H1, PRMT5, SS18, BRD4, KDM5D, PRMT7, STAG3L1, CD2BP2, MLL5, SUDS3, CHD1, MINA, CHD8, MORF4L1, or CHRAC1.

As shown in the Examples, shRNA based knock-down of any of these chromatin regulatory proteins caused cell death in cell lines that were resistant to Notch pathway inhibition.

These and other aspects of the invention will be described in greater detail herein.

Bromodomain-Containing Proteins

As described herein, various methods of the invention involve the use of a bromodomain inhibitor. Bromodomain inhibitors are compounds that inhibit the activity of bromodomain-containing proteins. Bromodomain-containing proteins, as their name implies, are proteins that comprise a bromodomain. Bromodomains (BRDs) function by detecting lysine acetylation (i.e., detecting ε-N-acetyl lysine, also known as Kac) on other proteins. Lysine acetylation neutralizes charge and can therefore alter protein conformation and protein-protein interactions. Lysine acetylation involves histone acetyltransferases (or HATs) and lysine deacetylation involves histone deactylases (or HDACs).

Bromodomains (BRDs) are a diverse family of evolutionarily conserved protein-interaction modules. One family of bromodomain-containing proteins, the BET (bromodomain and extra-terminal) family, is represented by six members in humans (BRD1, BRD2, BRD3, BRD4, BRD7 and the testis-specific isoform BRDT), with each containing two N-terminal BRDs. BRD4 and BRD2 mediate transcriptional elongation by recruiting the positive transcription elongation factor complex (P-TEFb). The P-TEFb core complex is composed of cyclin-dependent kinase-9 (CDK9) and its activator cyclin T. CDK9 phosphorylates the RNA polymerase II (RNAPII)C-terminal domain. RNAPII undergoes sequential phosphorylation at Ser5 during promoter clearance and at Ser2 by P-TEFb at the start of elongation. It has been shown that BRD4 couples P-TEFb to acetylated chromatin through its BRDs.

Examples of BRD-containing proteins include, but are not limited to, ASH1L, ATAD2A/B, BAZ1A/B, BAZ2A/B, BRD1, BRD2, BRD3, BRD4, BRDT, BRD7, BRD8A/B, BRD9, BRPF1A/B, BRPF3A, BRWD3, CECR2, CREBBP, EP300, FALZ, GCN5L2, MLL, PB1, PCAF, PHIP, PRKCBP1, SMARCA2A/B, SMARCA4, SP100/SP110/SP140, TAF1/TAF1L, TRIM24/TRIM28/TRIM33/TRIM66, WDR9, and ZMYND11.

As described herein, a novel role for BRD-containing proteins and other chromatin regulatory proteins in cancer has been elucidated in accordance with the invention. Tumor cells resistant to Notch pathway inhibitor treatment were found to have globally compact chromatin and altered expression of certain chromatin regulatory proteins with some having increased expression levels and some having decreased expression levels compared to a normal control. Knock-down of several chromatin regulatory proteins, including BRD4, in Notch pathway inhibitor-resistant tumor cells, using shRNA, resulted in decreased proliferation and increased cell death. Accordingly, aspects of the invention provide methods comprising administering to a subject having cancer a bromodomain inhibitor in an effective amount to treat the cancer, wherein the cancer is characterized by a Notch Activation mutation or by resistance to a Notch pathway inhibitor.

As described herein, use of a BRD inhibitor in combination with a Notch pathway inhibitor was found to result in reduction of tumor burden in a mouse model that was greater than treatment with the BRD inhibitor or the Notch pathway inhibitor alone. Additionally, use of the BRD inhibitor in combination with the Notch pathway inhibitor reduces the side effects associated with treatment using either agent alone. In particular, the side effects observed with the BRD inhibitor, JQ1, are reduced when the inhibitor is used in combination with a Notch pathway inhibitor. Such side effects include without limitation gastrointestinal side effects. The invention therefore contemplates a combination therapy that is associated with a lower frequency of side effects and/or less severe side effects. Accordingly, aspects of the invention provide methods comprising administering to a subject having cancer a BRD inhibitor and a Notch pathway inhibitor in an effective amount to treat the cancer.

Bromodomain Inhibitors

Bromodomain inhibitors are known in the art. A bromodomain inhibitor is any molecule or compound that can prevent or inhibit, in part or in whole, the binding of at least one bromodomain to acetyl-lysine residues of proteins (e.g., to the acetyl-lysine residues of histones). The bromodomain inhibitor may be any molecule or compound that inhibits a bromodomain as described above, including nucleic acids such as DNA and RNA aptamers, antisense oligonucleotides, siRNA and shRNA, small peptides, antibodies or antibody fragments, and small molecules such as small chemical compounds. It is to be understood that the bromodomain inhibitor may inhibit only one bromo-domain-containing protein or it may inhibit more than one or all bromodomain-containing proteins.

Examples of bromodomain inhibitors are described in JP 2009028043, JP 2009183291, WO 2011054843, WO 2011054848, WO2009/084693A1, WO2009084693, WO 2011054844, WO 2011054846, US 2012028912, Filippakopoulos et al. Bioorg Med Chem. 20(6): 1878-1886, 2012; Chung et al. J Med Chem. 54(11):3827-38, 2011; and Chung et al. J Biomol Screen. 16(10):1170-85, 2011, which are incorporated herein by reference.

In some embodiments, the bromodomain inhibitor is 1-[2-(1/-/-benzimidazol-2-ylthio)ethyl]-1,3-dihydro-3-methyl-2H-benzinidazole-2-thione (JP2008-156311), Alprazolam (Sigma-Aldrich), Midazolam (Sigma-Aldrich, GW841819X (BZD, GlaxoSmithKline), a compound in Table 1 (WO 2011054843), or any other bromodomain inhibitor compound described herein.

TABLE 1

Examples of Bromodomain inhibitors

| | Name | Structure |
|---|---|---|
| Example 1 | 1-methylethyl((2S,4R)-1-acetyl-2-methyl-6-{4-[(methylamino)methyl]phenyl}-1,2,3,4-tetrahydro-4-quinolinyl)carbamate | 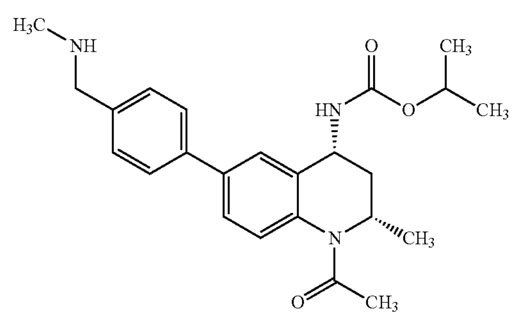 [SMILES: CNCc1ccc(-c2ccc3c(c2)[C@H](NC(=O)OC(C)C)C[C@H](C)N3C(C)=O)cc1] |
| Example 2 | 2-[(4S)-6-(4-Chlorophenyl)-1-methyl-8-(methyloxy)-4H-[1,2,4]triazolo[4,3-a][1,4]benzodiazepin-4-yl]-N-ethylacetamide | 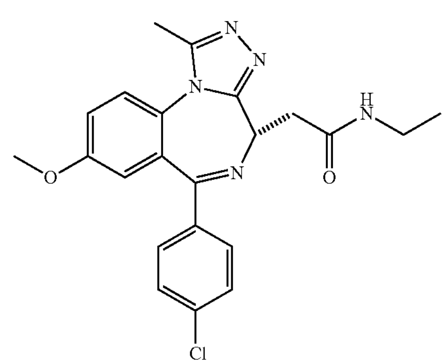 [SMILES: CCNC(=O)C[C@@H]1N=C(c2ccc(Cl)cc2)c2cc(OC)ccc2-n2c(C)nnc21] |

TABLE 1-continued

Examples of Bromodomain inhibitors

| Name | Structure |
| --- | --- |
| Example 3 | 7-(3,5-dimethyl-4-isoxazolyl)-8-(methoxy)-1-[(1R)-1-(2-pyridinyl)ethyl]-1,3-dihydro-2H-imidazo[4,5-c]quinolin-2-one |
| Example 4 | 7-(3,5-dimethyl-4-isoxazolyl)-8-(methoxy)-1-[(1R)-1-phenylethyl]-2-(tetrahydro-2H-pyran-4-yl)-1H-imidazo[4,5-c]quinoline |
| Example 5 | 4-{(2S,4R)-1-acetyl-4-[(4-chlorophenyl)amino]-2-methyl-1,2,3,4-tetrahydro-6-quinolinyl}benzoic acid |
| Example 6 | N-{1-methyl-7-[4-(1-piperidinylmethyl)phenyl][1,2,4]triazolo[4,3-a]quinolin-4-yl}urea |

In some embodiments, the bromodomain inhibitor is a BET inhibitor. A BET inhibitor is any molecule or compound that can prevent or inhibit the binding of the bromodomain of at least one BET family member to acetyl-lysine residues of proteins. The BET inhibitor may be any molecule or compound that inhibits a BET as described above, including nucleic acids such as DNA and RNA aptamers, antisense oligonucleotides, siRNA and shRNA, small peptides, antibodies or antibody fragments, and small molecules such as small chemical compounds.

Examples of BET inhibitors are described in US 2011143651, WO2009/084693A1, WO 2011143669, WO 2011143660, WO 2011054851, and JP 2008156311, which are incorporated herein by reference. It is to be understood that a BET inhibitor may inhibit only one BET family member or it may inhibit more than one or all BET family members. Examples of BET inhibitors known in the art include, but are not limited to, RVX-208 (Resverlogix), PFI-1 (Structural Genomics Consortium), OTX015 (Mitsubishi Tanabe Pharma Corporation), BzT-7, GSK525762A (iBET, GlaxoSmithKline), and the compounds below (WO 2011054851, GlaxoSmithKline):

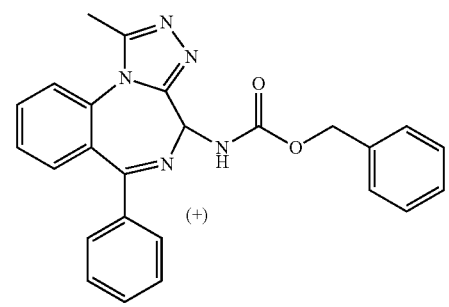

(I)

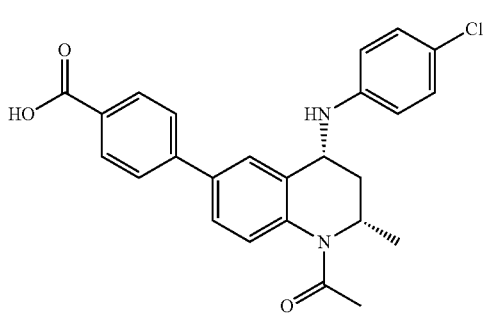 [SMILES: CC(=O)N1c2ccc(-c3ccc(C(=O)O)cc3)cc2[C@H](Nc2ccc(Cl)cc2)C[C@@H]1C]

(II)

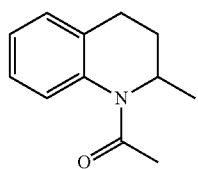

(III)

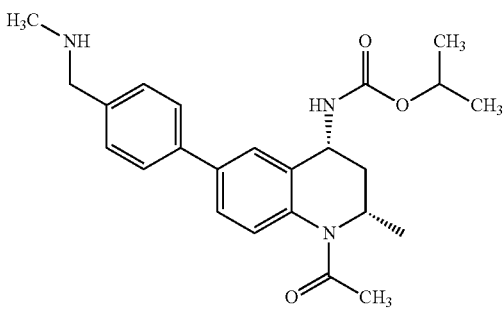

(IV)

In some embodiments, the BET inhibitor is a small molecule compound (e.g., JQ1 or derivatives thereof and compounds of formulas I-XXII or any other compound described herein) that binds to the binding pocket of the first bromodomain of a BET family member (e.g., BRD1, BRD2, BRD3, BRD4, BRD7, BRDT; see WO 2011143669).

In some important embodiments, the BET inhibitor is JQ1 and has the formula below:

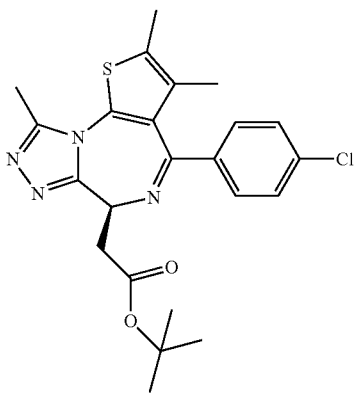

JQ1

In some embodiments, the BET inhibitor has the structures of Formulas I-XXII or any other compound as described below. These structures are known in the art (WO 2011143660, which is incorporated herein by reference).

In some embodiments, a bromodomain or BET inhibitor is a compound of Formula I:

(I)

wherein X is N or $CR_5$; $R_5$ is H, alkyl, cycloalkyl, heterocycloalkyl, aryl, or heteroaryl, each of which is optionally substituted; $R_B$ is H, alkyl, hydroxylalkyl, aminoalkyl, alkoxyalkyl, haloalkyl, hydroxy, alkoxy, or —COO—R3, each of which is optionally substituted; ring A is aryl or heteroaryl; each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group; R is alkyl, cycloalkyl, heterocycloalkyl, aryl, or heteroaryl; each of which is optionally substituted;

$R_i$ is —$(CH_2)_n$-L, in which n is 0-3 and L is H, —COO—R3, —CO—R3, —CO—N($R_3R_4$), —S(O)$_2$—$R_3$, —S(O)$_2$—N($R_3R_4$), N($R_3R4$), N(R4)C(O)$R_3$, optionally substituted aryl, or optionally substituted heteroaryl;

$R_2$ is H, D (deuterium), halogen, or optionally substituted alkyl;

each $R_3$ is independently selected from the group consisting of:
(i) H, aryl, substituted aryl, heteroaryl, or substituted heteroaryl;
(ii) heterocycloalkyl or substituted heterocycoalkyl;
(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$Ci_2$ cycloalkyl, substituted —$C_3$-$Ci_2$ cycloalkyl, —$C_3$-$Ci_2$ cycloalkenyl, or substituted —$C_3$-$Ci_2$ cycloalkenyl, each of which may be optionally substituted; and
(iv) $NH_2$, N=$CR_4R_6$;

each $R_4$ is independently H, alkyl, cycloalkyl, heterocycloalkyl, aryl, or heteroaryl, each of which is optionally substituted;

or $R_3$ and $R_4$ are taken together with the nitrogen atom to which they are attached to form a 4-10-membered ring;

$R_6$ is alkyl, alkenyl, cycloalkyl, cycloalkenyl, heterocycloalkyl, aryl, or heteroaryl, each of which is optionally substituted; or $R_4$ and $R_6$ are taken together with the carbon atom to which they are attached to form a 4-10-membered ring;

m is 0, 1, 2, or 3;

provided that (a) if ring A is thienyl, X is N, R is phenyl or substituted phenyl, $R_2$ is H, RB is methyl, and Ri is —$(CH_2)_n$-L, in which n is 1 and L is —CO—N($R_3R_4$), then $R_3$ and $R_4$ are not taken together with the nitrogen atom to which they are attached to form a morpholino ring;

(b) if ring A is thienyl, X is N, R is substituted phenyl, $R_2$ is H, RB is methyl, and Ri is —$(CH_2)_n$-L, in which n is 1 and L is —CO—N($R_3R_4$), and one of $R_3$ and $R_4$ is H, then the other of $R_3$ and $R_4$ is not methyl, hydroxyethyl, alkoxy, phenyl, substituted phenyl, pyridyl or substituted pyridyl; and (c) if ring A is thienyl, X is N, R is substituted phenyl, $R_2$ is H, $R_B$ is methyl, and Ri is —$(CH_2)_n$-L, in which n is 1 and L is —COO—$R_3$ then $R_3$ is not methyl or ethyl; or a salt, solvate or hydrate thereof.

In certain embodiments, R is aryl or heteroaryl, each of which is optionally substituted.

In certain embodiments, L is H, —COO—$R_3$, —CO—N($R_3R_4$), —S(O)$_2$—$R_3$, —S(O)$_2$—N($R_3R_4$), N($R_3R_4$), N($R_4$)C(O)$R_3$ or optionally substituted aryl. In certain embodiments, each $R_3$ is independently selected from the group consisting of: H, —Ci-$C_8$ alkyl, which is optionally substituted, containing 0, 1, 2, or 3 heteroatoms selected from O, S, or N; or NH$_2$, N=CR$_4$R$_6$.

In certain embodiments, $R_2$ is H, D, halogen or methyl.

In certain embodiments, $R_B$ is alkyl, hydroxyalkyl, haloalkyl, or alkoxy; each of which is optionally substituted.

In certain embodiments, $R_B$ is methyl, ethyl, hydroxymethyl, methoxymethyl, trifluoromethyl, COOH, COOMe, COOEt, or COOCH$_2$OC(O)CH$_3$.

In certain embodiments, ring A is a 5 or 6-membered aryl or heteroaryl. In certain embodiments, ring A is thiofuranyl, phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

In certain embodiments, ring A is phenyl or thienyl.

In certain embodiments, m is 1 or 2, and at least one occurrence of $R_A$ is methyl.

In certain embodiments, each $R_A$ is independently H, an optionally substituted alkyl, or any two $R_A$ together with the atoms to which each is attached, can form an aryl.

In some embodiments, a bromodomain or BET inhibitor is a compound of Formula II:

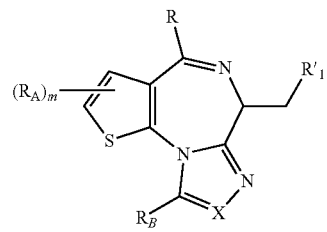

(II)

wherein X is N or CR$_5$; R$_5$ is H, alkyl, cycloalkyl, heterocycloalkyl, aryl, or heteroaryl, each of which is optionally substituted; R$_B$ is H, alkyl, hydroxylalkyl, aminoalkyl, alkoxyalkyl, haloalkyl, hydroxy, alkoxy, or —COO—R$_3$, each of which is optionally substituted;

each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;

R is alkyl, cycloalkyl, heterocycloalkyl, aryl, or heteroaryl, each of which is optionally substituted;

R'$_1$ is H, —COO—R$_3$, —CO—R$_3$, optionally substituted aryl, or optionally substituted heteroaryl;

each R$_3$ is independently selected from the group consisting of:
(i) H, aryl, substituted aryl, heteroaryl, substituted heteroaryl;
(ii) heterocycloalkyl or substituted heterocycloalkyl;
(iii) —C$_1$-C$_8$ alkyl, —C$_2$-C$_8$ alkenyl or —C$_2$-C$_8$ alkynyl, each containing 0, 1, 2, or 3 heteroatoms selected from O, S, or N; —C$_3$-C$_{12}$ cycloalkyl, substituted —C$_3$-C$_{12}$ cycloalkyl; —C$_3$-C$_{12}$ cycloalkenyl, or substituted —C$_3$-C$_{12}$ cycloalkenyl; each of which may be optionally substituted;

m is 0, 1, 2, or 3;

provided that if R'$_1$ is —COO—R$_3$, X is N, R is substituted phenyl, and R$_B$ is methyl, then R$_3$ is not methyl or ethyl;

or a salt, solvate or hydrate thereof.

In certain embodiments, R is aryl or heteroaryl, each of which is optionally substituted. In certain embodiments, R is phenyl or pyridyl, each of which is optionally substituted. In certain embodiments, R is p-Cl-phenyl, o-Cl-phenyl, m-Cl-phenyl, p-F-phenyl, o-F-phenyl, m-F-phenyl or pyridinyl.

In certain embodiments, R'$_1$ is —COO—R$_3$, optionally substituted aryl, or optionally substituted heteroaryl; and R$_3$ is —C$_3$-C$_8$ alkyl, which contains 0, 1, 2, or 3 heteroatoms selected from O, S, or N, and which may be optionally substituted. In certain embodiments, R'$_1$ is —COO—R$_3$, and R$_3$ is methyl, ethyl, propyl, i-propyl, butyl, sec-butyl, or t-butyl; or R'$_1$ is H or optionally substituted phenyl.

In certain embodiments, R$_B$ is methyl, ethyl, hydroxymethyl, methoxymethyl, trifluoromethyl, COOH, COOMe, COOEt, COOCH$_2$OC(O)CH$_3$.

In certain embodiments, R$_B$ is methyl, ethyl, hydroxymethyl, methoxymethyl, trifluoromethyl, COOH, COOMe, COOEt, or COOCH$_2$OC(O)CH$_3$.

In certain embodiments, each $R_A$ is independently an optionally substituted alkyl, or any two $R_A$ together with the atoms to which each is attached, can form a fused aryl.

In certain embodiments, each $R_A$ is methyl.

In some embodiments, a bromodomain or BET inhibitor is a compound of formula III:

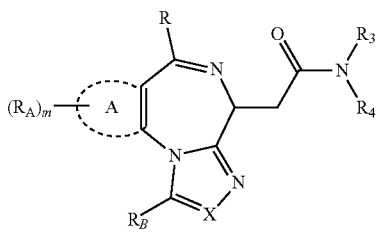

(III)

wherein

X is N or CR$_5$; R$_5$ is H, alkyl, cycloalkyl, heterocycloalkyl, aryl, or heteroaryl, each of which is optionally substituted; RB is H, alkyl, hydroxylalkyl, aminoalkyl, alkoxyalkyl, haloalkyl, hydroxy, alkoxy, or —COO—R3, each of which is optionally substituted; ring A is aryl or heteroaryl; each R$_4$ is independently alkyl, cycloalkyl, heterocycloalkyl, aryl, or heteroaryl, each of which is optionally substituted; or any two RA together with the atoms to which each is attached, can form a fused aryl or heteroaryl group;

R is alkyl, cycloalkyl, heterocycloalkyl, aryl, or heteroaryl, each of which is optionally substituted;

each R$_3$ is independently selected from the group consisting of:
(i) H, aryl, substituted aryl, heteroaryl, or substituted heteroaryl;
(ii) heterocycloalkyl or substituted heterocycloalkyl;
(iii) —C$_1$-C$_8$ alkyl, —C$_2$-C$_8$ alkenyl or —C$_2$-C$_8$ alkynyl, each containing 0, 1, 2, or 3 heteroatoms selected from O, S, or N; —C$_3$-C$_{12}$ cycloalkyl, substituted —C$_3$-C$_{12}$ cycloalkyl, —C$_3$-C$_{12}$ cycloalkenyl, or substituted —C$_3$-C$_{12}$ cycloalkenyl, each of which may be optionally substituted; and
(iv) NH$_2$, N=CR$_4$R$_6$;

each R$_4$ is independently H, alkyl, alkyl, cycloalkyl, heterocycloalkyl, aryl, or heteroaryl, each of which is optionally substituted; or R$_3$ and R$_4$ are taken together with the nitrogen atom to which they are attached to form a 4-10-membered ring;

R$_6$ is alkyl, alkenyl, cycloalkyl, cycloalkenyl, heterocycloalkyl, aryl, or heteroaryl, each of which is optionally substituted; or R$_4$ and R$_6$ are taken together with the carbon atom to which they are attached to form a 4-10-membered ring;

m is 0, 1, 2, or 3;

provided that:
(a) if ring A is thienyl, X is N, R is phenyl or substituted phenyl, R$_B$ is methyl, then R$_3$ and R$_4$ are not taken together with the nitrogen atom to which they are attached to form a morpholino ring; and
(b) if ring A is thienyl, X is N, R is substituted phenyl, R$_2$ is H, R$_B$ is methyl, and one of R$_3$ and R$_4$ is H, then the other of R$_3$ and R$_4$ is not methyl, hydroxyethyl, alkoxy, phenyl, substituted phenyl, pyridyl or substituted pyridyl;

or a salt, solvate or hydrate thereof.

In certain embodiments, R is aryl or heteroaryl, each of which is optionally substituted.

In certain embodiments, R is phenyl or pyridyl, each of which is optionally substituted.

In certain embodiments, R is p-Cl-phenyl, o-Cl-phenyl, m-Cl-phenyl, p-F-phenyl, o-F-phenyl, m-F-phenyl or pyridinyl. In certain embodiments, R$_3$ is H, NH$_2$, or N=CR$_4$R$_6$.

In certain embodiments, each R$_4$ is independently H, alkyl, cycloalkyl, heterocycloalkyl, aryl, heteroaryl; each of which is optionally substituted.

In certain embodiments, R$_6$ is alkyl, alkenyl, cycloalkyl, cycloalkenyl, heterocycloalkyl, aryl, or heteroaryl, each of which is optionally substituted.

In some embodiments, a bromodomain or BET inhibitor is a compound of formula IV:

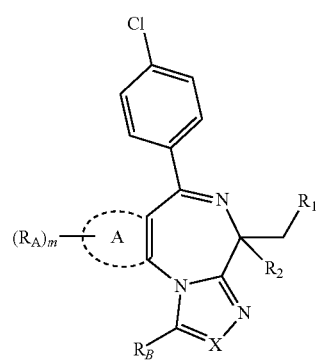

(IV)

wherein X is N or CR$_5$; R$_5$ is H, alkyl, cycloalkyl, heterocycloalkyl, aryl, or heteroaryl, each of which is optionally substituted;

R$_B$ is H, alkyl, hydroxylalkyl, aminoalkyl, alkoxyalkyl, haloalkyl, hydroxy, alkoxy, or —COO—R3, each of which is optionally substituted;

ring A is aryl or heteroaryl;

each R$_A$ is independently alkyl, cycloalkyl, heterocycloalkyl, aryl, or heteroaryl, each of which is optionally substituted; or any two R$_A$ together with the atoms to which each is attached, can form a fused aryl or heteroaryl group;

Ri is —(CH$_2$)$_n$-L in which n is 0-3 and L is H, —COO—R3, —CO—R3, —CO—N(R$_3$R$_4$), —S(O)$_2$—R$_3$, —S(O)$_2$—N(R$_3$R$_4$), N(R$_3$R4), N(R4)C(O)R$_3$, optionally substituted aryl, or optionally substituted heteroaryl;

R$_2$ is H, D, halogen, or optionally substituted alkyl;

each R$_3$ is independently selected from the group consisting of:
(i) H, aryl, substituted aryl, heteroaryl, or substituted heteroaryl;
(ii) heterocycloalkyl or substituted heterocycloalkyl;
(iii) —C$_1$-C$_8$ alkyl, —C$_2$-C$_8$ alkenyl or —C$_2$-C$_8$ alkynyl, each containing 0, 1, 2, or 3 heteroatoms selected from O, S, or N; —C$_3$-C$_{12}$ cycloalkyl, substituted —C$_3$-C$_{12}$ cycloalkyl, —C$_3$-C$_{12}$ cycloalkenyl, or substituted —C$_3$-C$_{12}$ cycloalkenyl, each of which may be optionally substituted; and
(iv) NH$_2$, N=CR$_4$R$_6$;

each R$_4$ is independently H, alkyl, alkyl, cycoloalkyl, heterocycloalkyl, aryl, or heteroaryl, each of which is optionally substituted;

or R$_3$ and R$_4$ are taken together with the nitrogen atom to which they are attached to form a 4-10-membered ring;

R$_6$ is alkyl, alkenyl, cycloalkyl, cycloalkenyl, heterocycloalkyl, aryl, or heteroaryl, each of which is optionally substituted; or R$_4$ and R$_6$ are taken together with the carbon atom to which they are attached to form a 4-10-membered ring;

m is 0, 1, 2, or 3;

provided that (a) if ring A is thienyl, X is N, $R_2$ is H, RB is methyl, and Ri is —(CH$_2$)$_n$-L, in which n is 0 and L is —CO—N(R$_3$R$_4$), then R$_3$ and R$_4$ are not taken together with the nitrogen atom to which they are attached to form a morpholino ring;

(b) if ring A is thienyl, X is N, $R_2$ is H, RB is methyl, and Ri is —(CH$_2$)$_n$-L, in which n is 0 and L is —CO—N(R$_3$R$_4$), and one of R$_3$ and R$_4$ is H, then the other of R$_3$ and R$_4$ is not methyl, hydroxyethyl, alkoxy, phenyl, substituted phenyl, pyridyl or substituted pyridyl; and (c) if ring A is thienyl, X is N, $R_2$ is H, $R_B$ is methyl, and Ri is —(CH$_2$)$_n$-L, in which n is 0 and L is —COO—R$_3$, then R$_3$ is not methyl or ethyl; or a salt, solvate or hydrate thereof.

In certain embodiments, Ri is —(CH$_2$)$_n$-L, in which n is 0-3 and L is —COO—R$_3$, optionally substituted aryl, or optionally substituted heteroaryl; and R$_3$ is —C$_1$-C$_8$ alkyl, which contains 0, 1, 2, or 3 heteroatoms selected from O, S, or N, and which may be optionally substituted. In certain embodiments, n is 1 or 2 and L is alkyl or —COO—R$_3$, and R$_3$ is methyl, ethyl, propyl, i-propyl, butyl, sec-butyl, or t-butyl; or n is 1 or 2 and L is H or optionally substituted phenyl.

In certain embodiments, $R_2$ is H or methyl.

In certain embodiments, $R_B$ is methyl, ethyl, hydroxy methyl, methoxymethyl, trifluoromethyl, COOH, COOMe, COOEt, COOCH$_2$OC(O)CH$_3$.

In certain embodiments, ring A is phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

In certain embodiments, each $R_A$ is independently an optionally substituted alkyl, or any two $R_A$ together with the atoms to which each is attached, can form an aryl.

The invention also provides compounds of Formulae V-XXII, and any compound described herein.

In some embodiments, a bromodomain or BET inhibitor is:

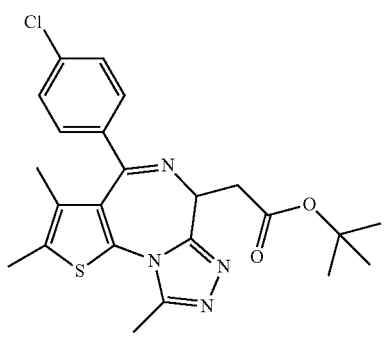 [SMILES: Cc1sc2c(c1C)C(c1ccc(Cl)cc1)=NC(CC(=O)OC(C)(C)C)c1nnc(C)n1-2]

a salt, solvate or hydrate thereof.

In certain embodiments, the compound is (+)-JQ1:

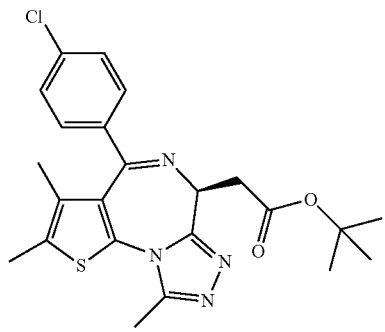 [SMILES: Cc1sc2c(c1C)C(c1ccc(Cl)cc1)=N[C@@H](CC(=O)OC(C)(C)C)c1nnc(C)n1-2]

or a salt, solvate or hydrate thereof.

In some embodiments, a bromodomain or BET inhibitor is a compound represented by the formula:

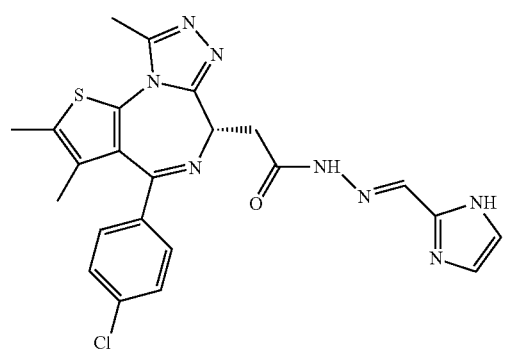

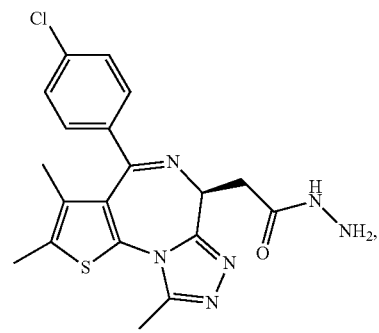

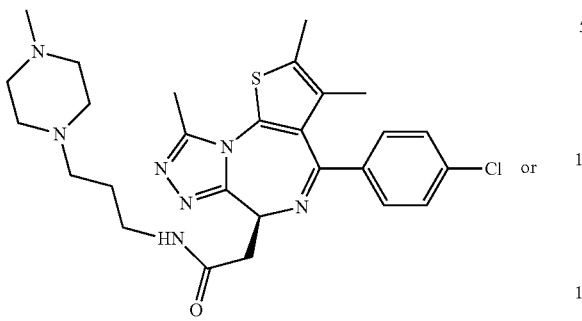
or
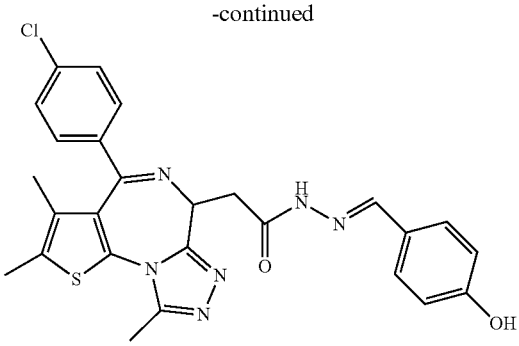
a salt, solvate or hydrate thereof.
In some embodiments, a bromodomain or BET inhibitor is a compound represented by the formula:
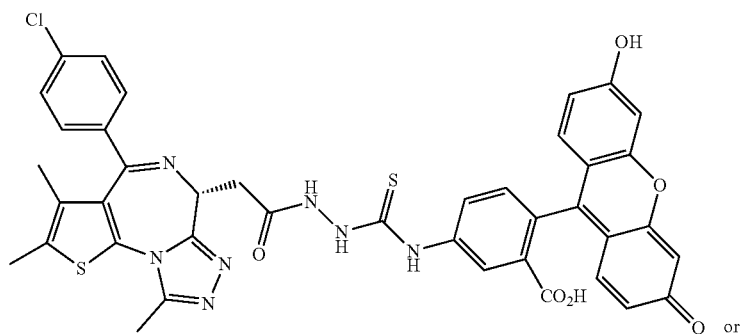
or
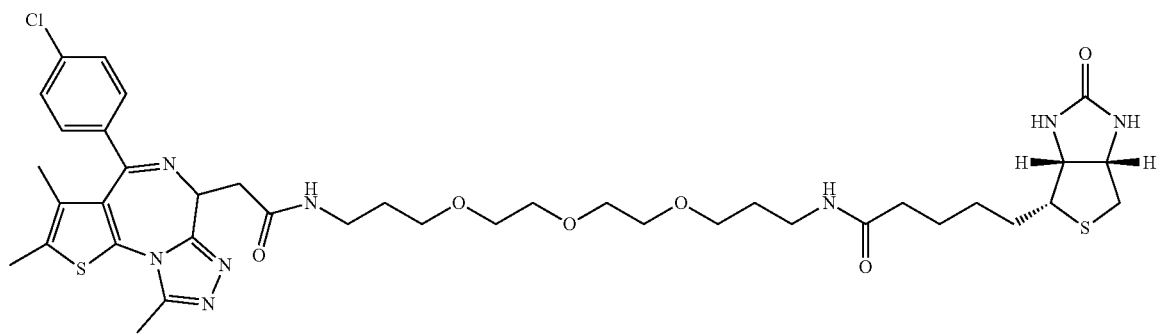
a salt, solvate or hydrate thereof.

In some embodiments, a bromodomain or BET inhibitor is a compound represented by any following formulae:
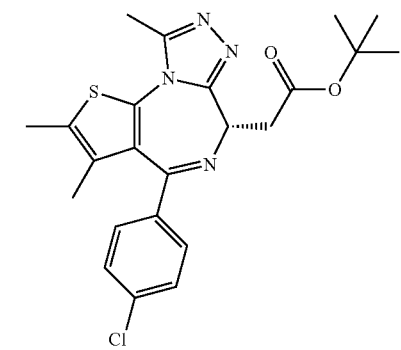
JQ1S
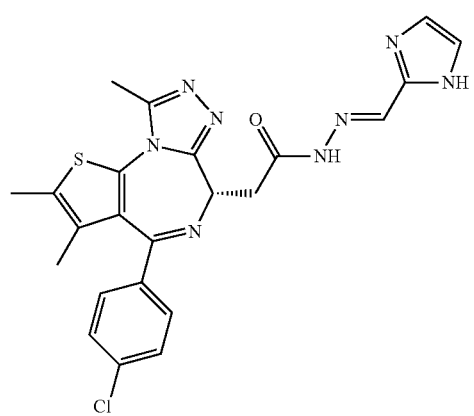
JQ6
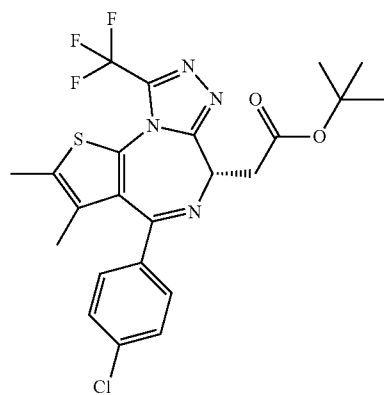
JQ11
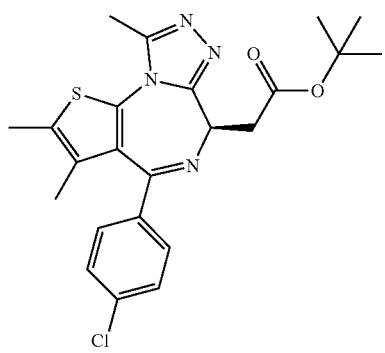
JQ1R
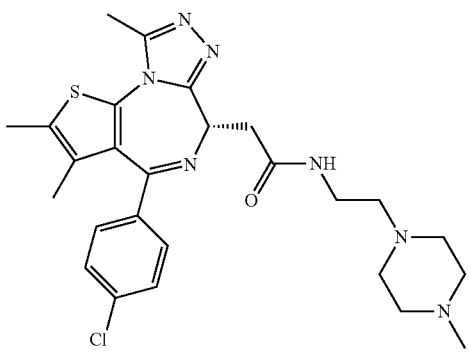
JQ13
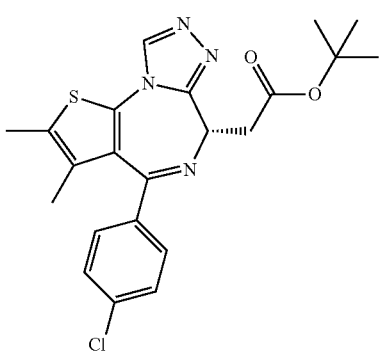
JQ21
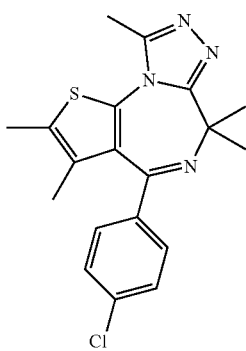
JQ20
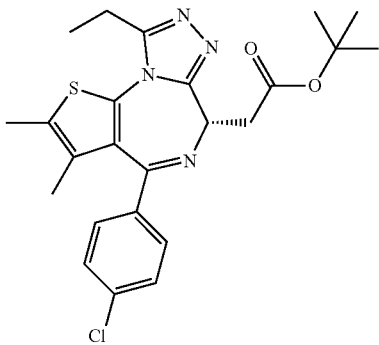
JQ19

JQ24B
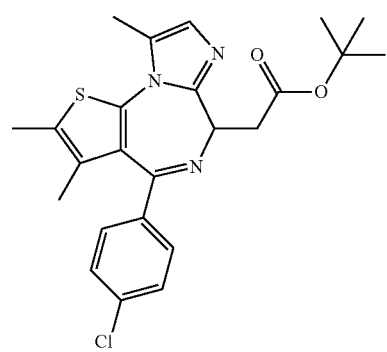
JQ8
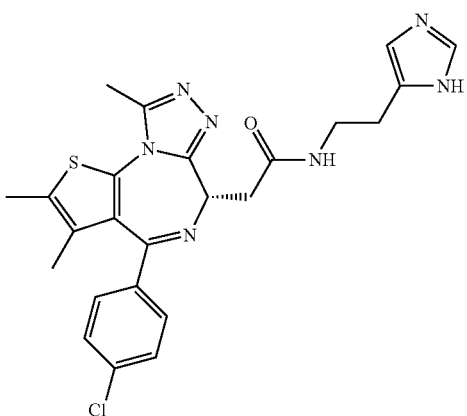
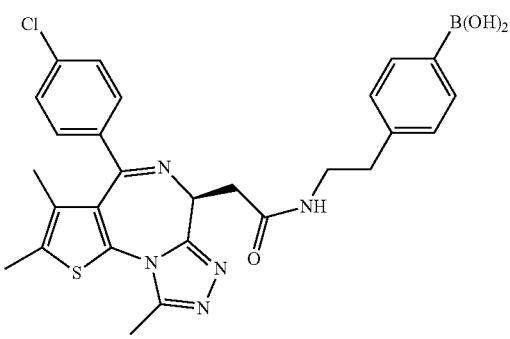
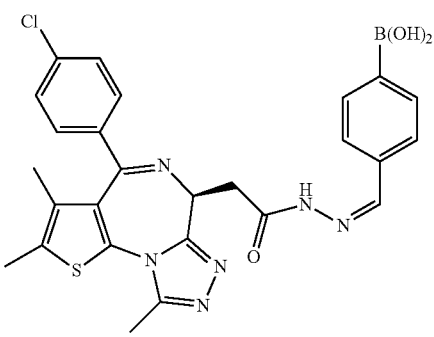
a salt, solvate or hydrate thereof. In some embodiments, a bromodomain or BET inhibitor is a compound represented by any following structures:
JQ18
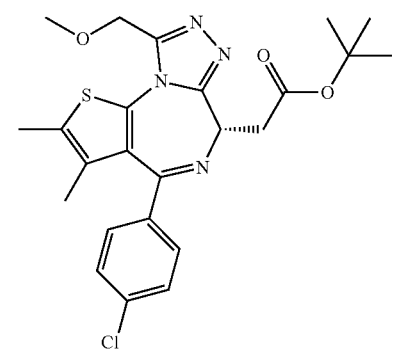
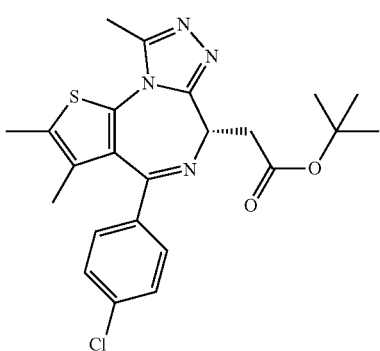
KS1
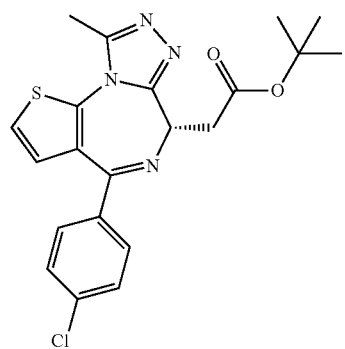
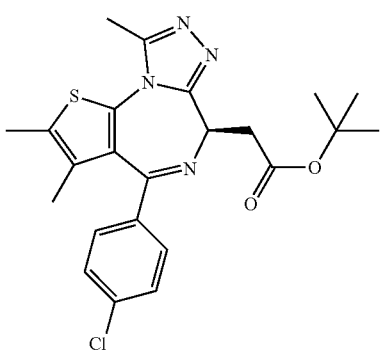
or a salt, solvate or hydrate thereof. In some embodiments, a bromodomain or BET inhibitor is a compound represented by any one of the following formulae:

27
-continued
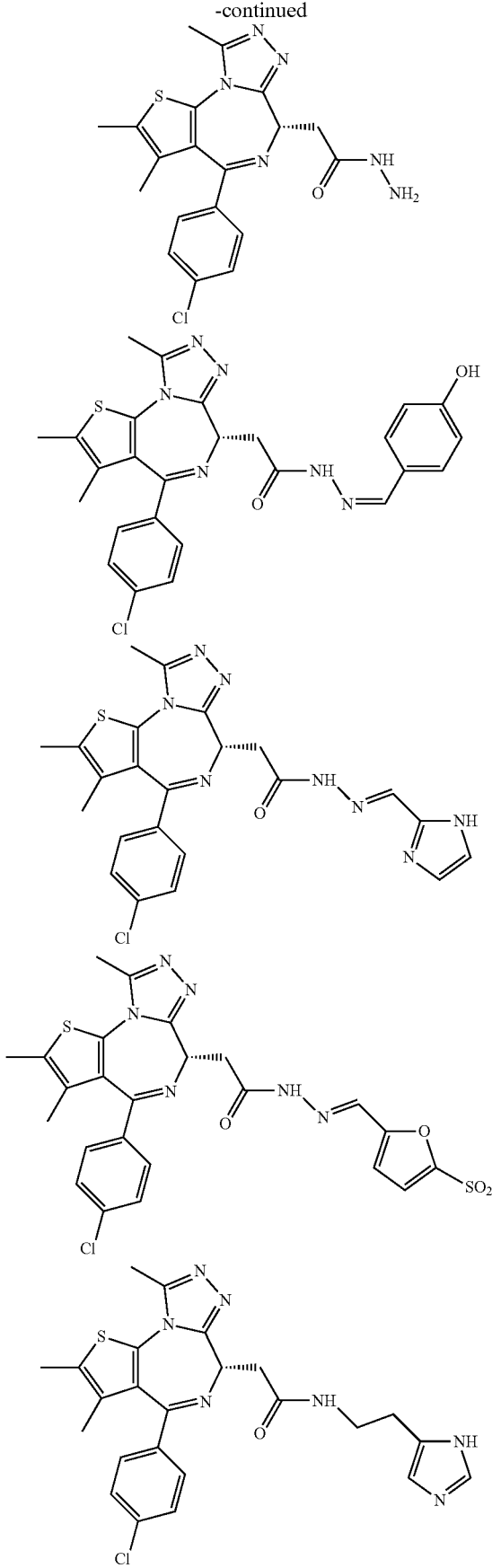
28
-continued
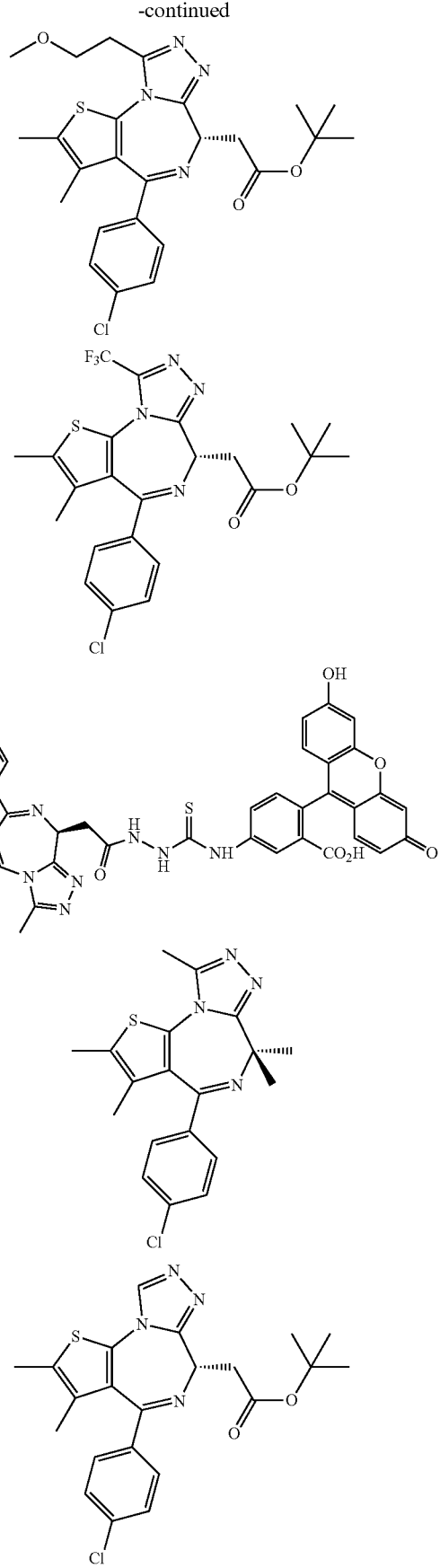

29
-continued
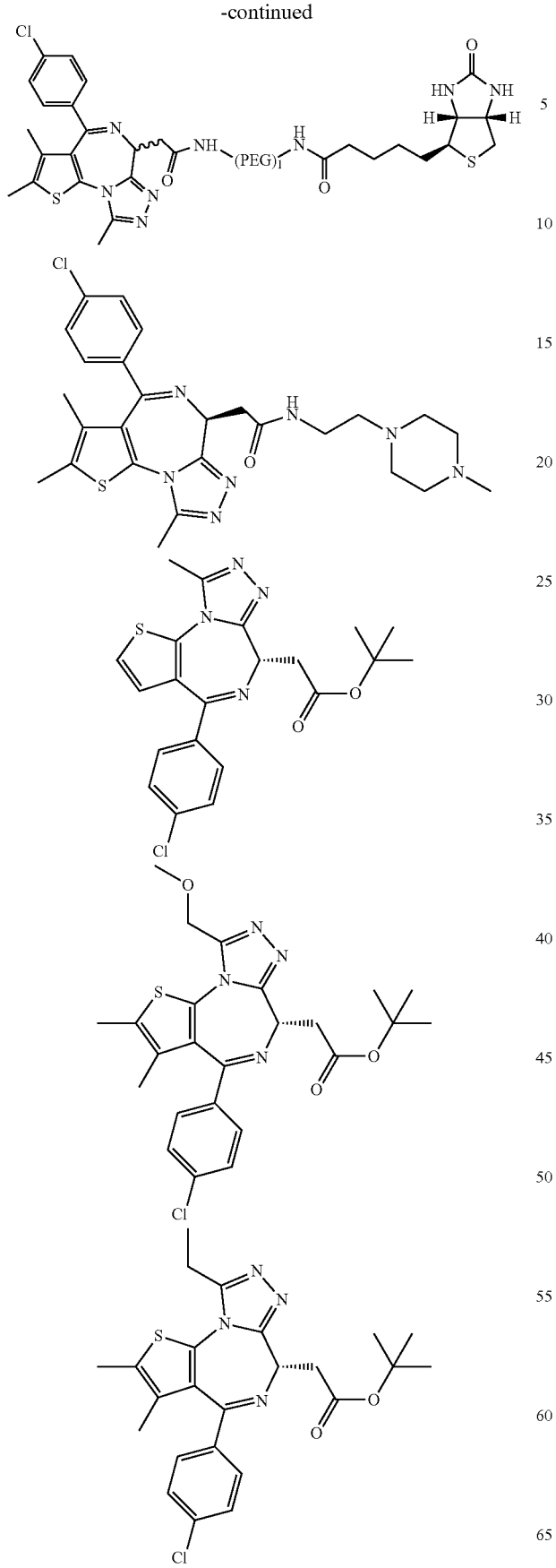
30
-continued
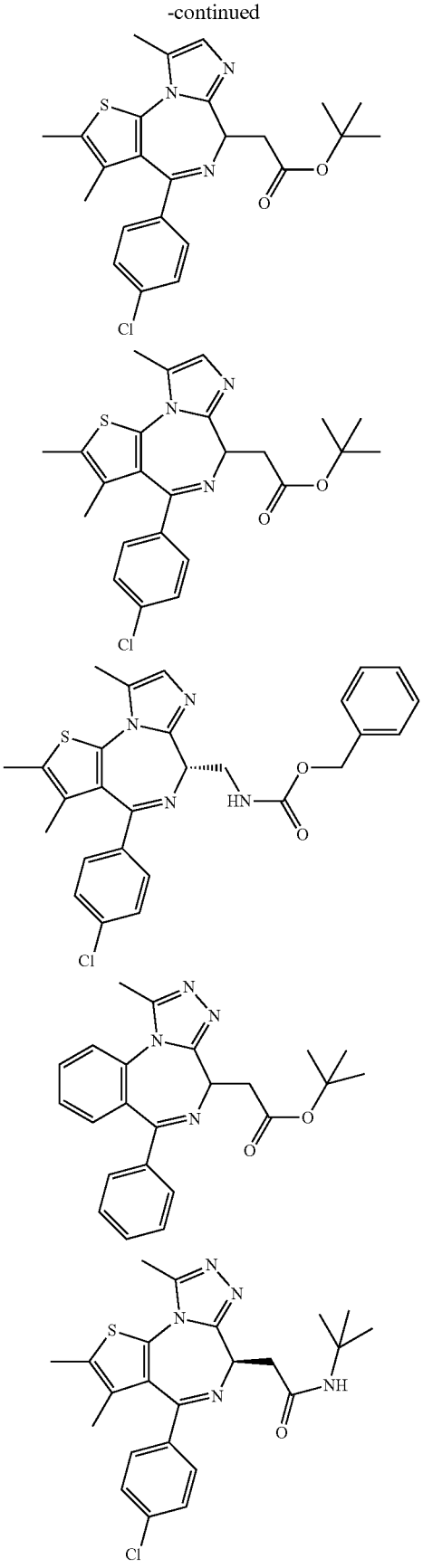

31
-continued
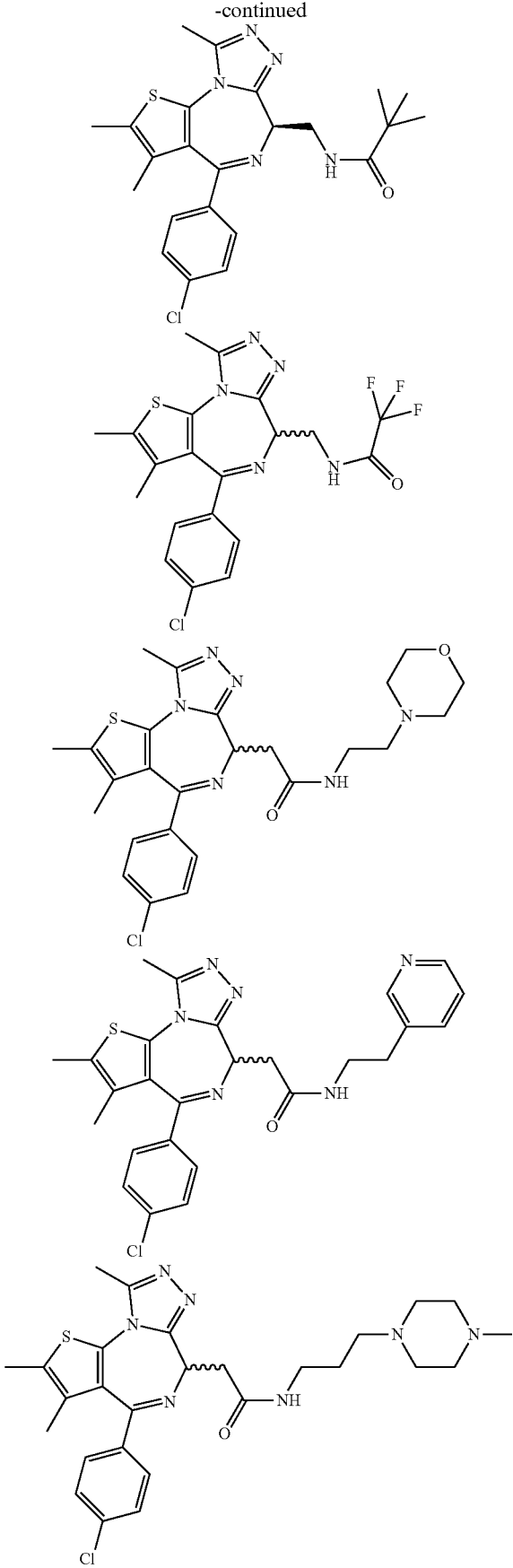
32
-continued
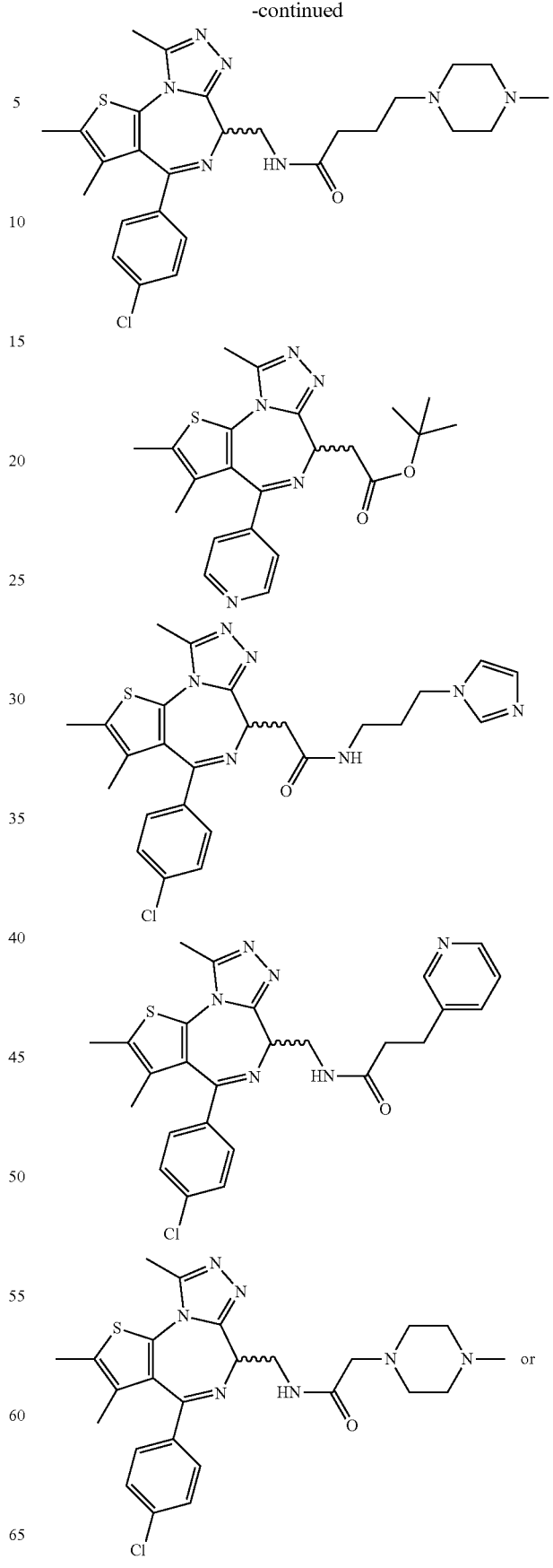
or

33
-continued
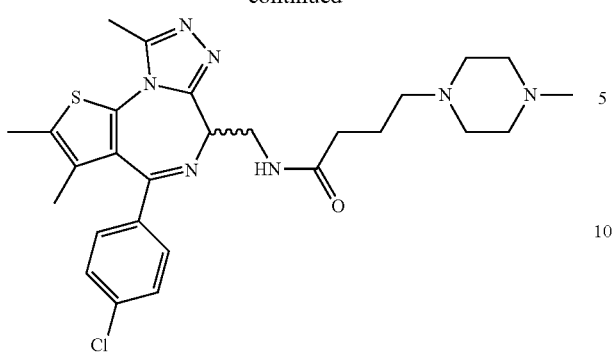
or a salt, solvate or hydrate thereof. In some embodiments, a bromodomain or BET inhibitor can be one of the following structures:
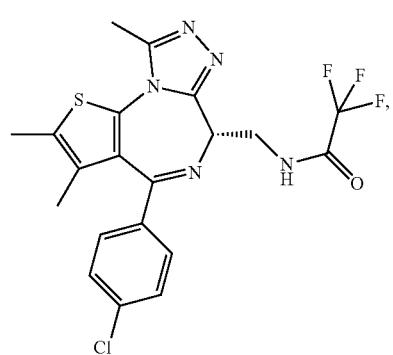
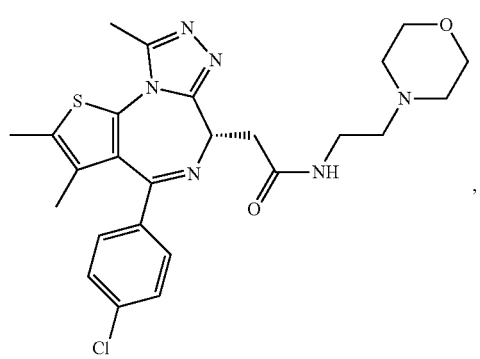 [SMILES: Cc1sc2c(c1C)C(c1ccc(Cl)cc1)=N[C@@H](CC(=O)NCCc1cccnc1)c1nnc(C)n1-2]
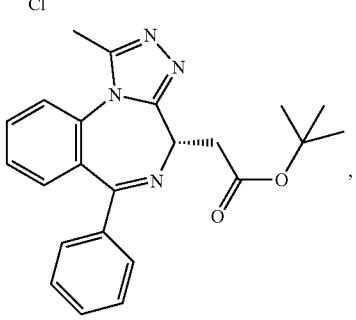
34
-continued
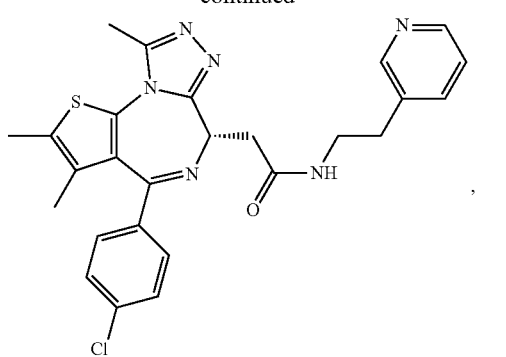
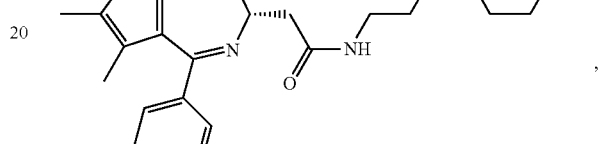
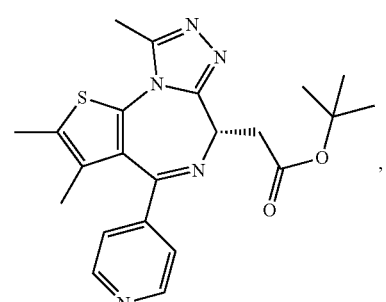
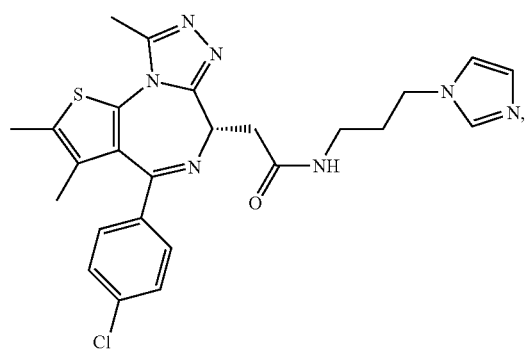

35
-continued
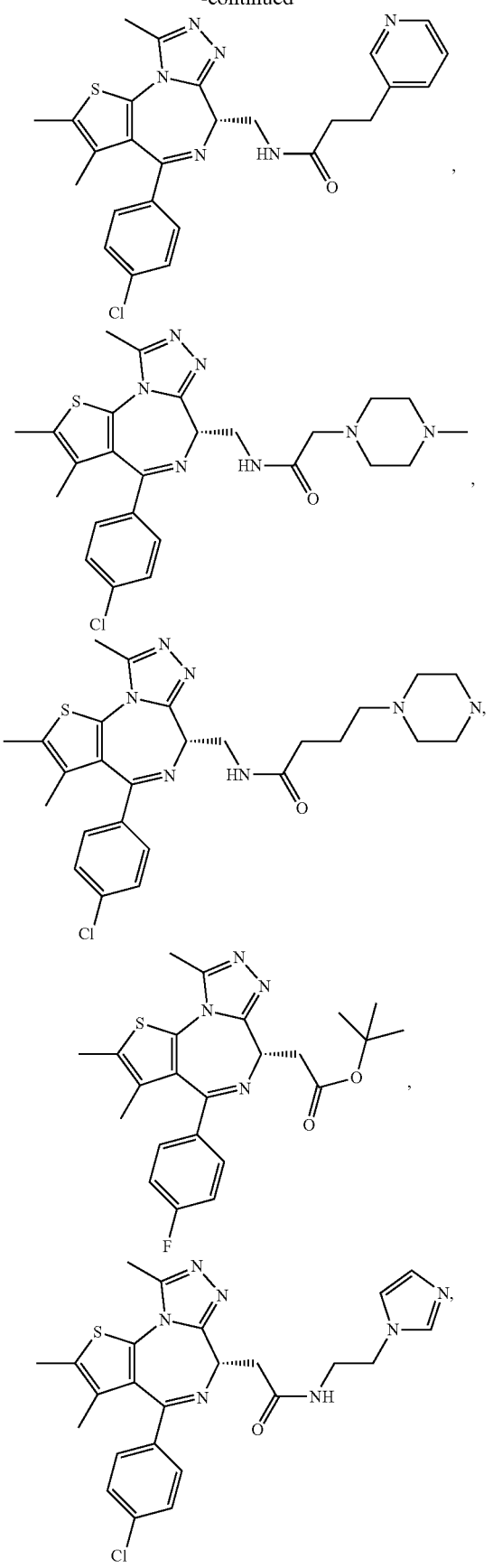
36
-continued
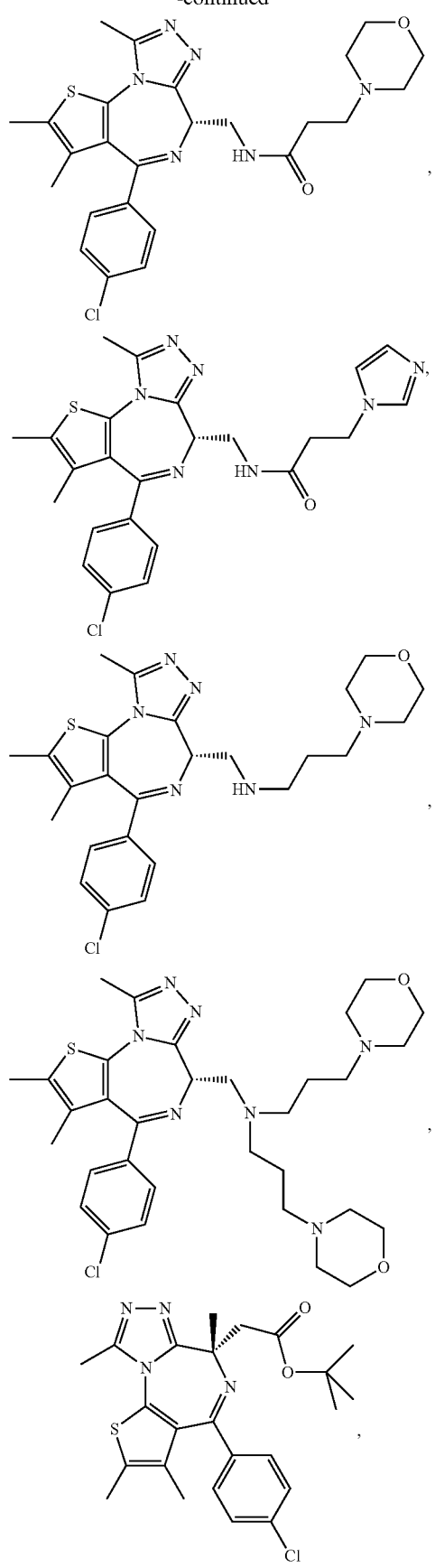

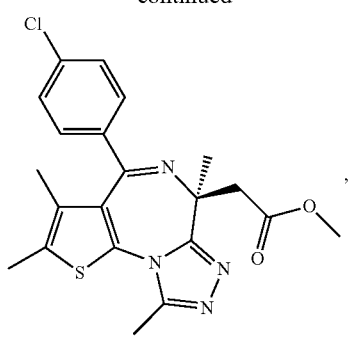

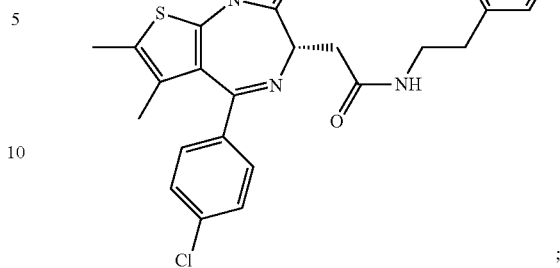

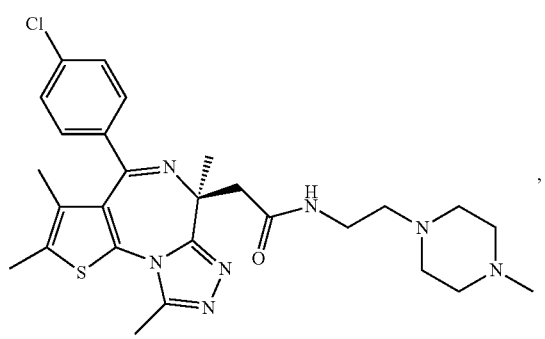

or a salt, solvate or hydrate thereof. In some embodiments, a bromodomain or BET inhibitor is a compound represented by the following structure:

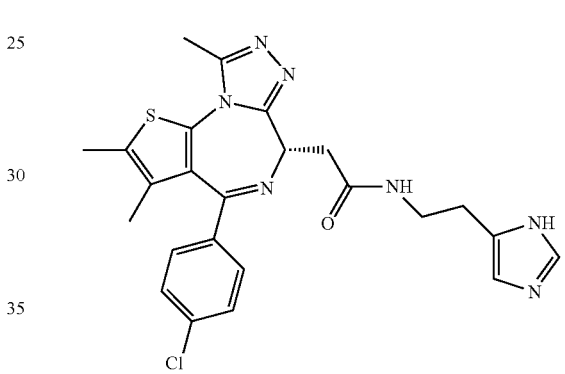

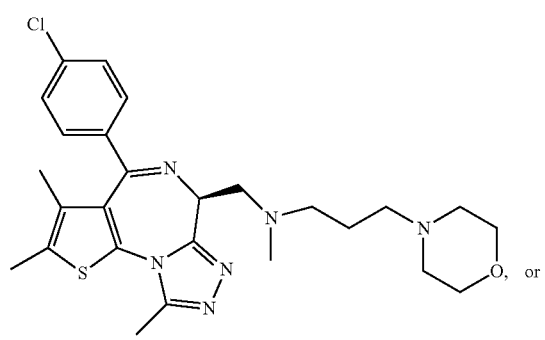

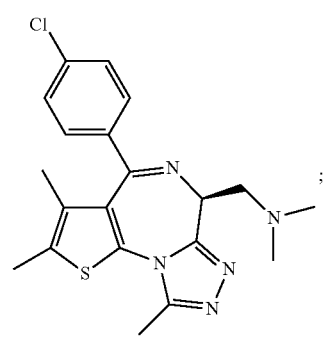

a salt, solvate or hydrate thereof.

In some embodiments, a bromodomain or BET inhibitor is a compound represented by the following structure:

or a salt, solvate or hydrate thereof. In some embodiments, a bromodomain or BET inhibitor is a compound represented by the following structure:

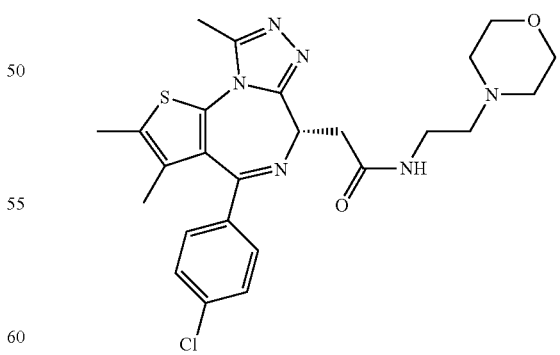

or a salt, solvate or hydrate thereof. In some embodiments, a bromodomain or BET inhibitor is a compound with the opposite chirality of any compound shown herein. In some embodiments, a bromodomain or BET inhibitor is a compound represented by Formula (V), (VI), or (VII):

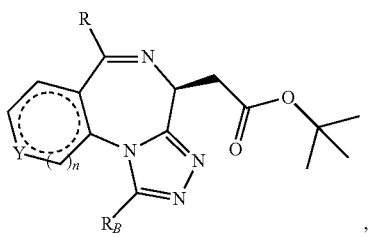

(V)

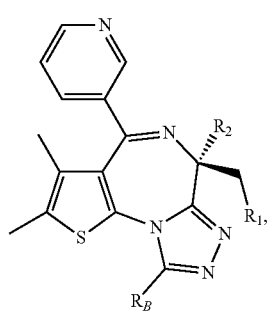

(VI)

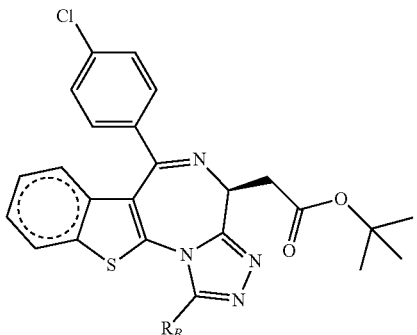

(VII)

in which R, Ri, and $R_2$ and RB have the same meaning as in Formula (I); Y is O, N, S, or $CR_5$, in which R5 has the same meaning as in Formula (I); n is 0 or 1; and the dashed circle in Formula (VII) indicates an aromatic or non-aromatic ring; or a salt, solvate or hydrate thereof.

In certain embodiments of any of the Formulae I-IV and VI (or any formula herein), $R_6$ represents the non-carbonyl portion of an aldehyde shown in Table A, below (i.e., for an aldehyde of formula $R_6CHO$, $R_6$ is the non-carbonyl portion of the aldehyde). In certain embodiments, $R_4$ and $R_6$ together represent the non-carbonyl portion of a ketone shown in Table A (i.e., for a ketone of formula $R_6C(O)R_4$, $R_4$ and $R_6$ are the non-carbonyl portion of the ketone).

TABLE A
(Plates 1 to 4)
Plate 1
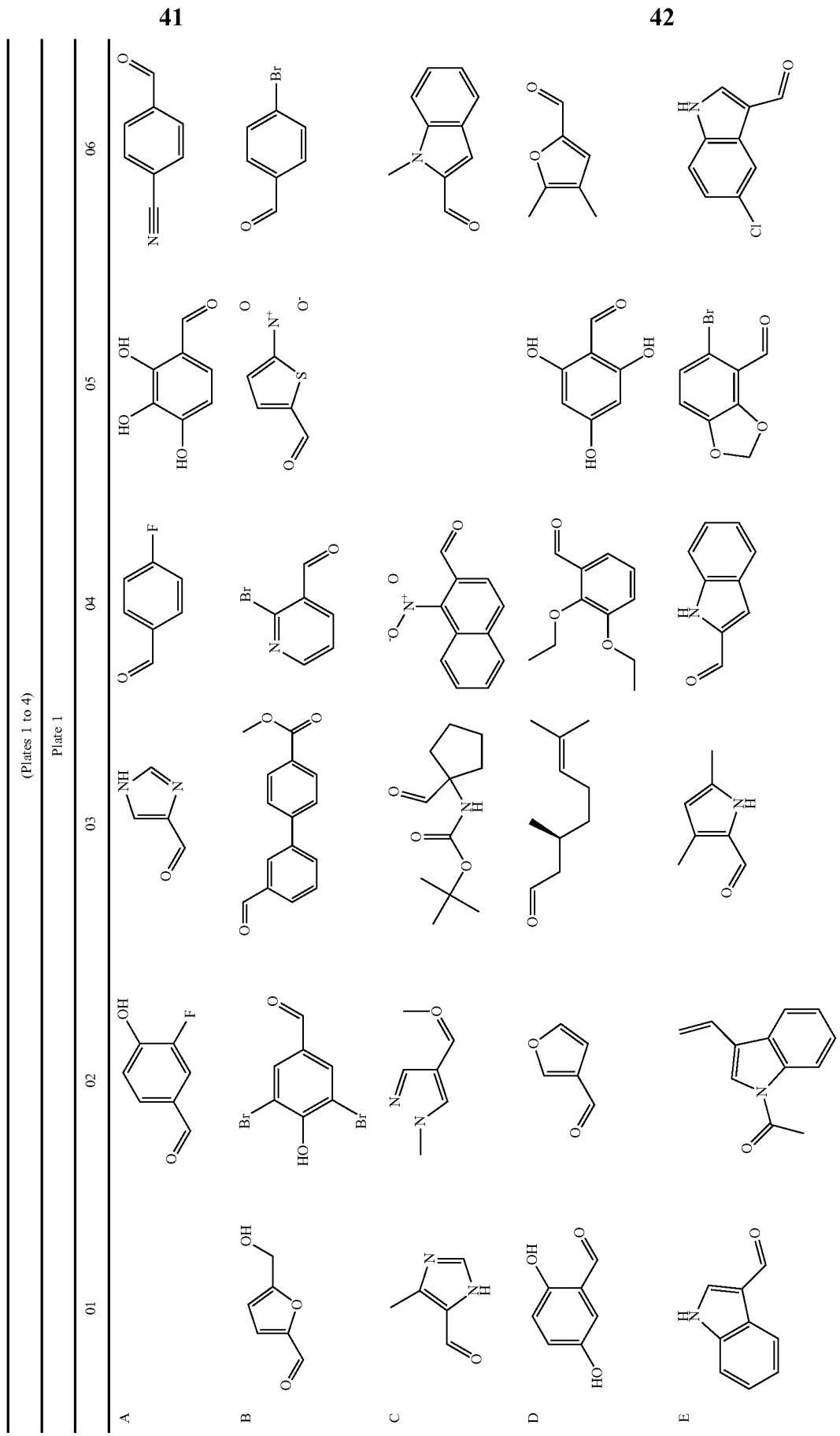

TABLE A-continued
(Plates 1 to 4)

TABLE A-continued
(Plates 1 to 4)
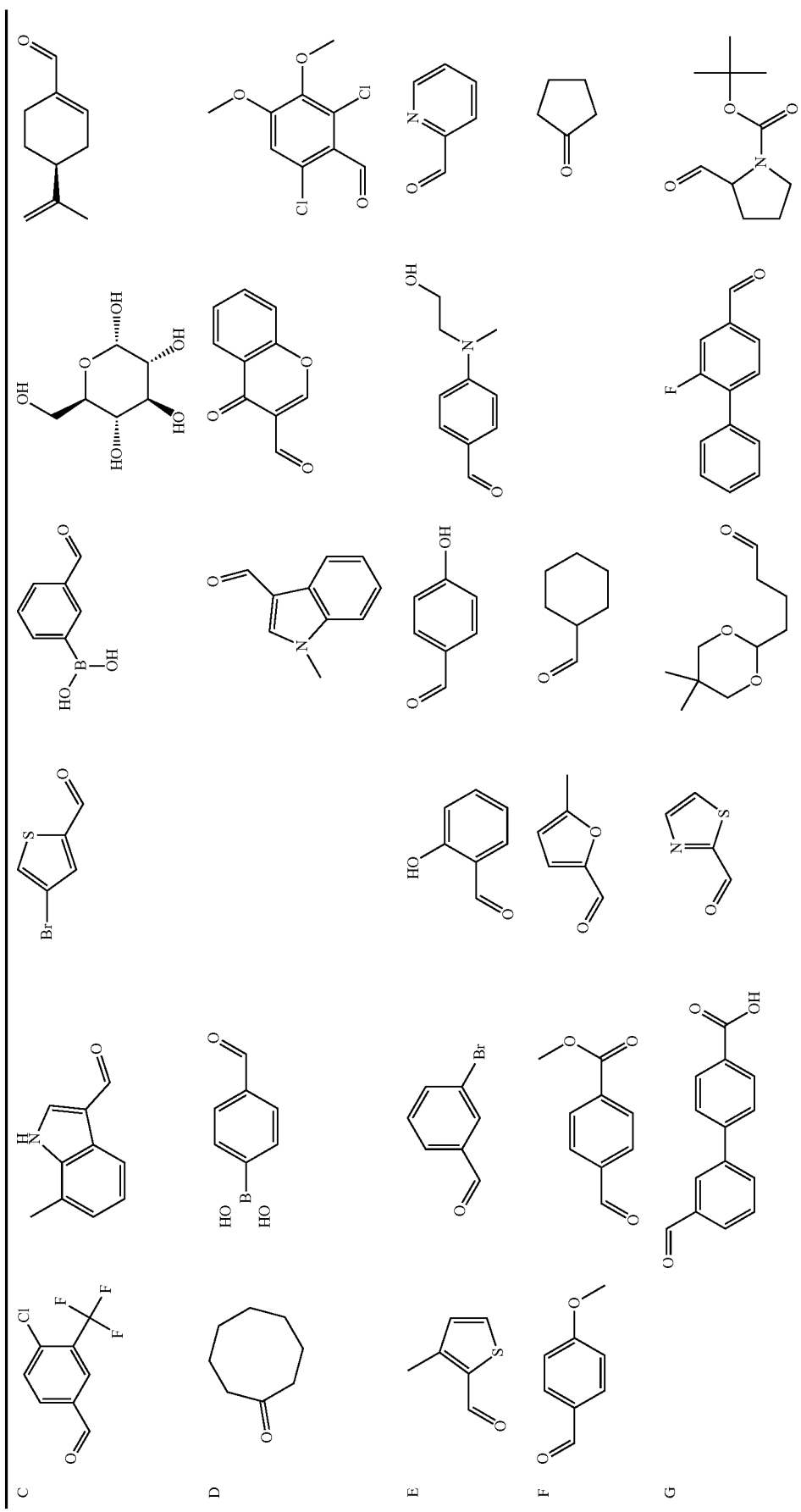

TABLE A-continued
(Plates 1 to 4)
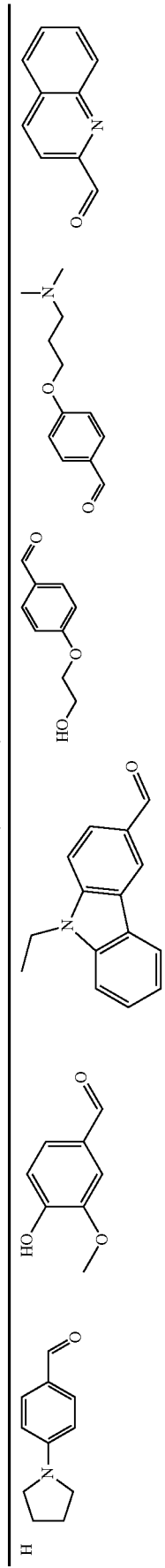
Plate 2
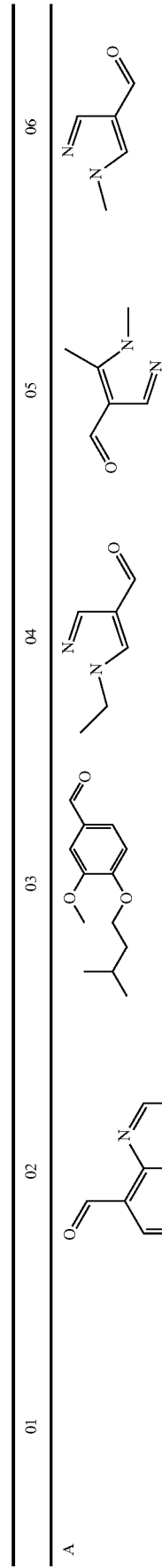
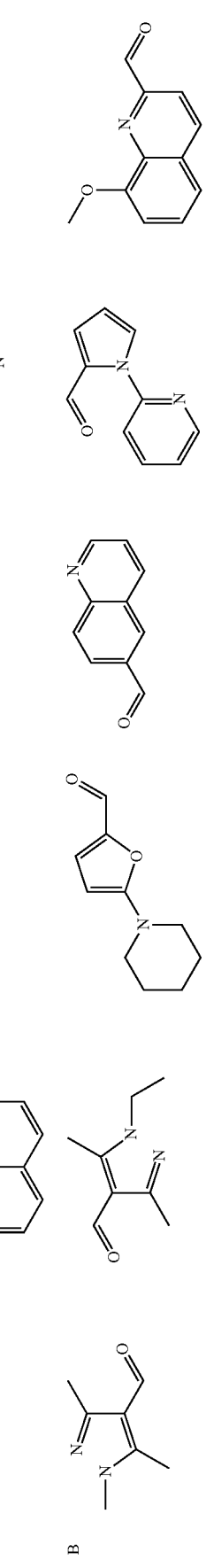
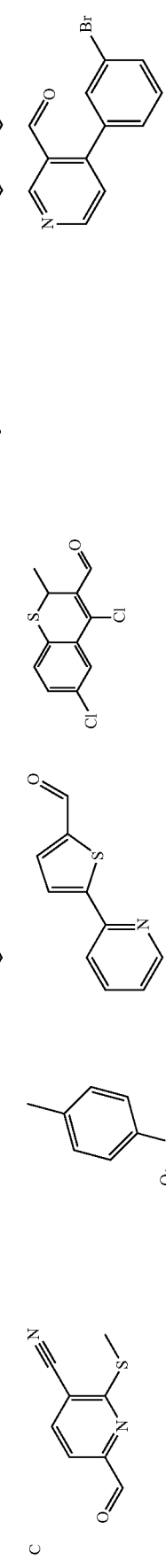
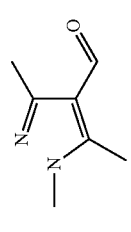
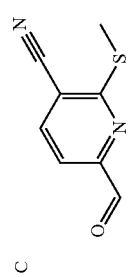

TABLE A-continued (Plates 1 to 4)

TABLE A-continued
(Plates 1 to 4)
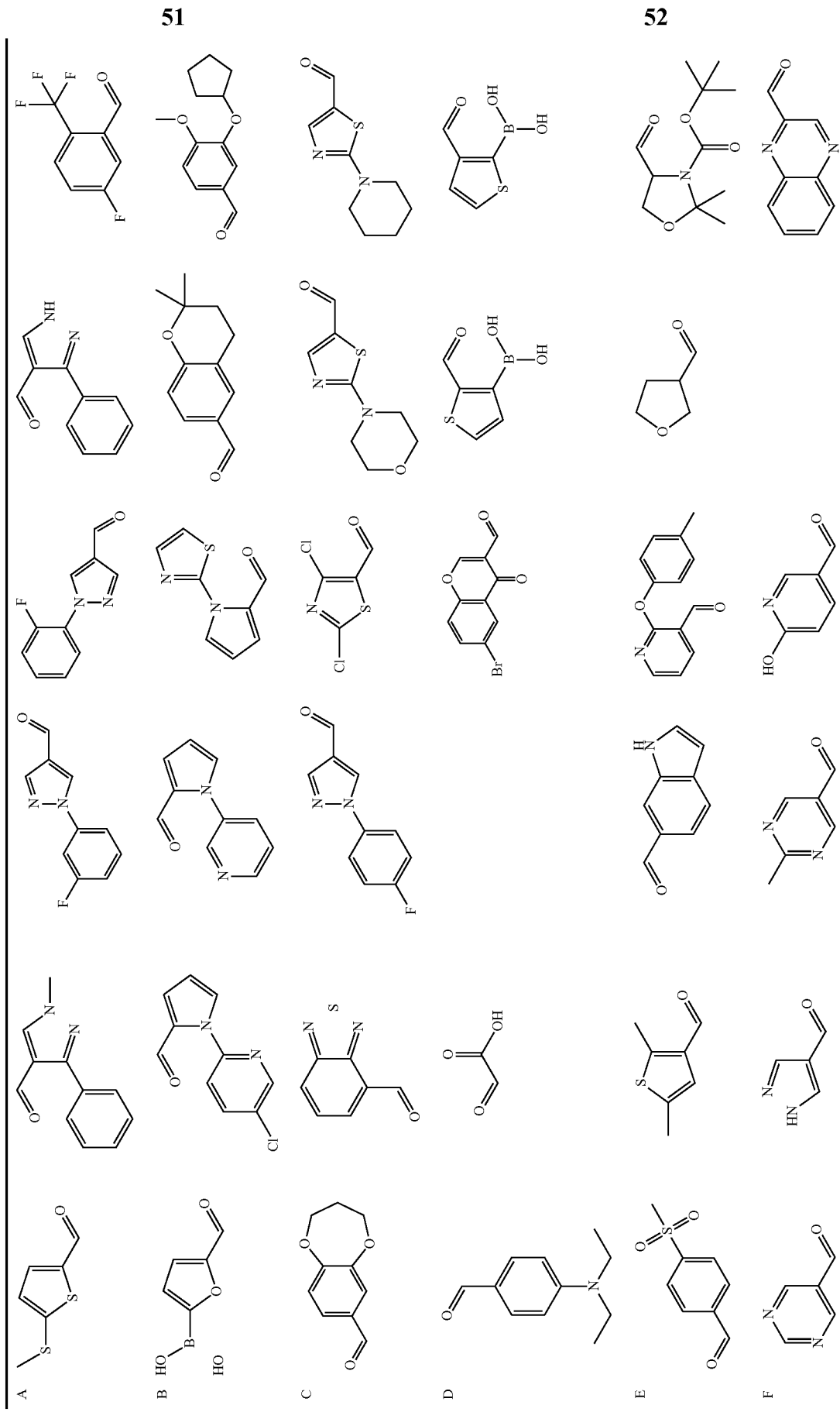

TABLE A-continued
(Plates 1 to 4)
Plate 3
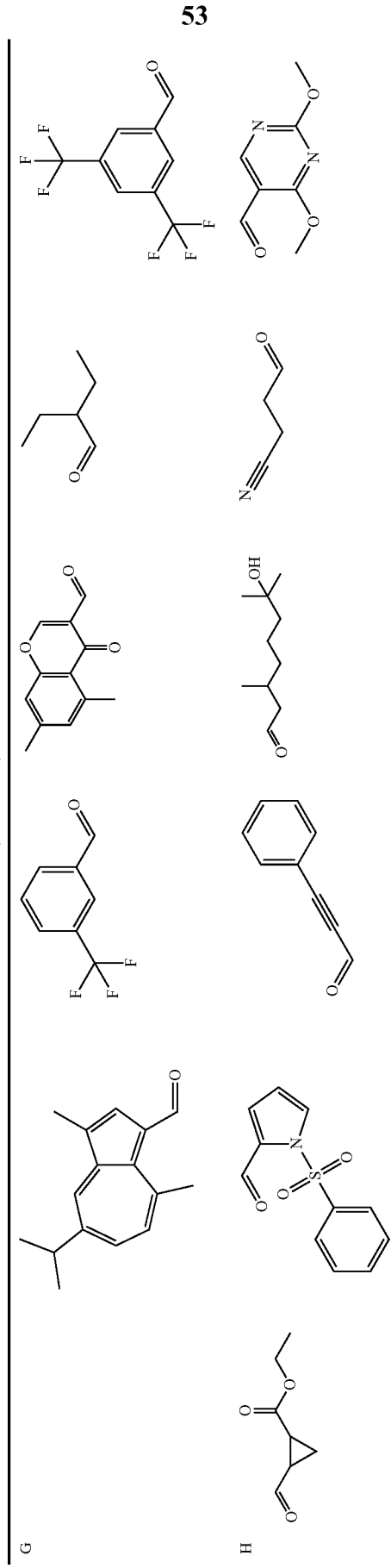
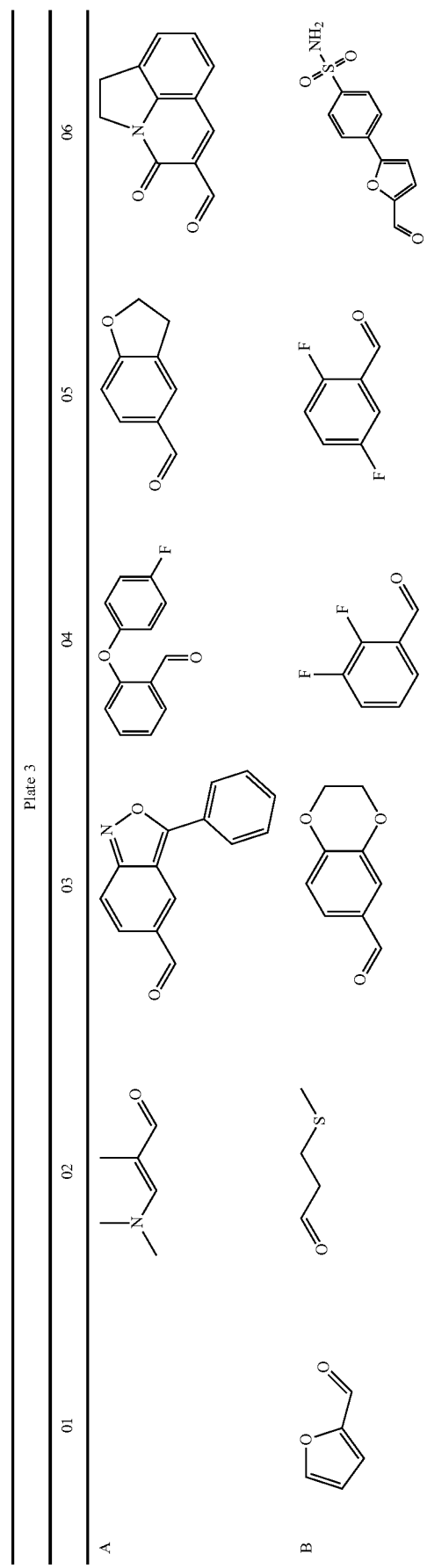

TABLE A-continued
(Plates 1 to 4)
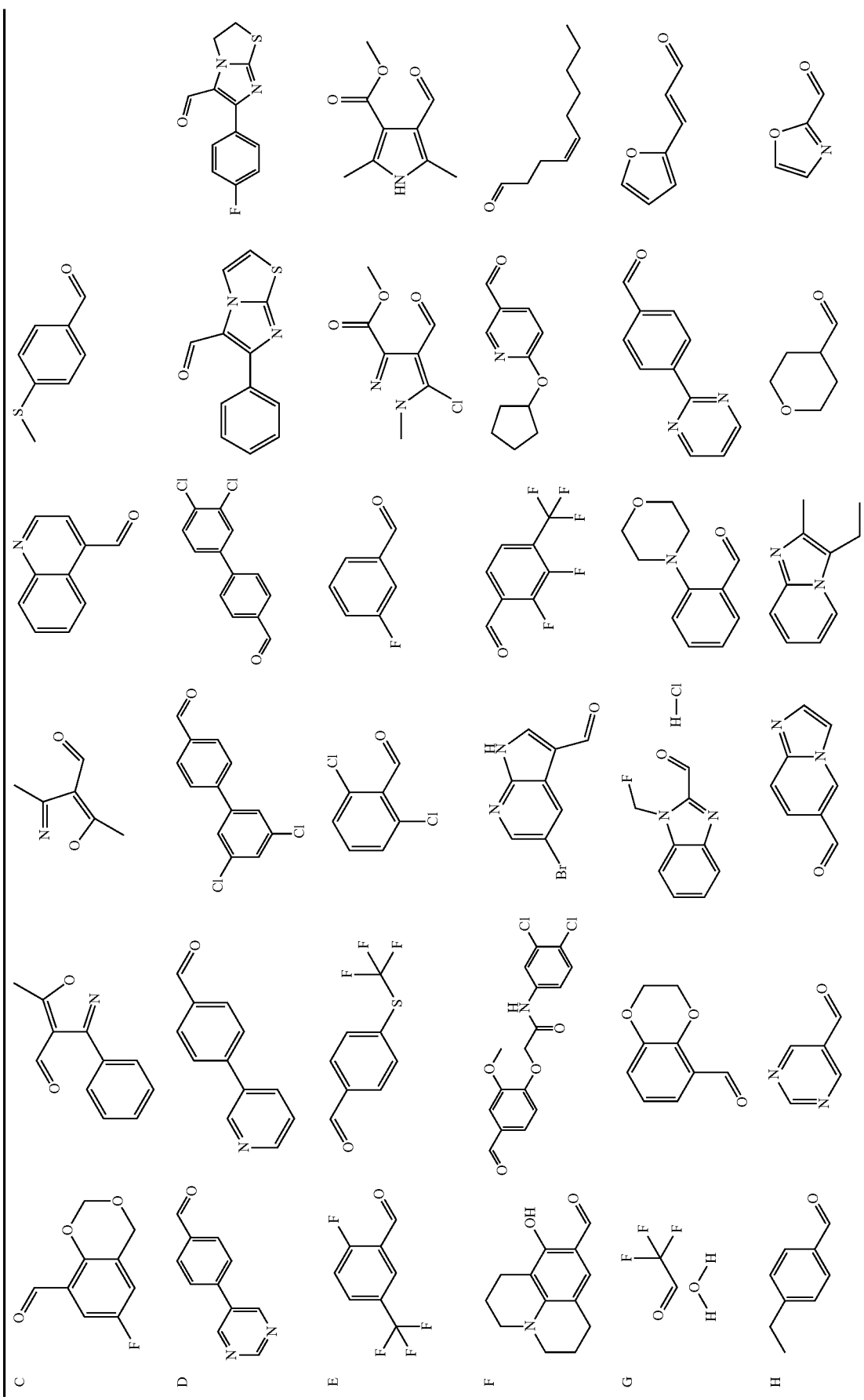

TABLE A-continued
(Plates 1 to 4)
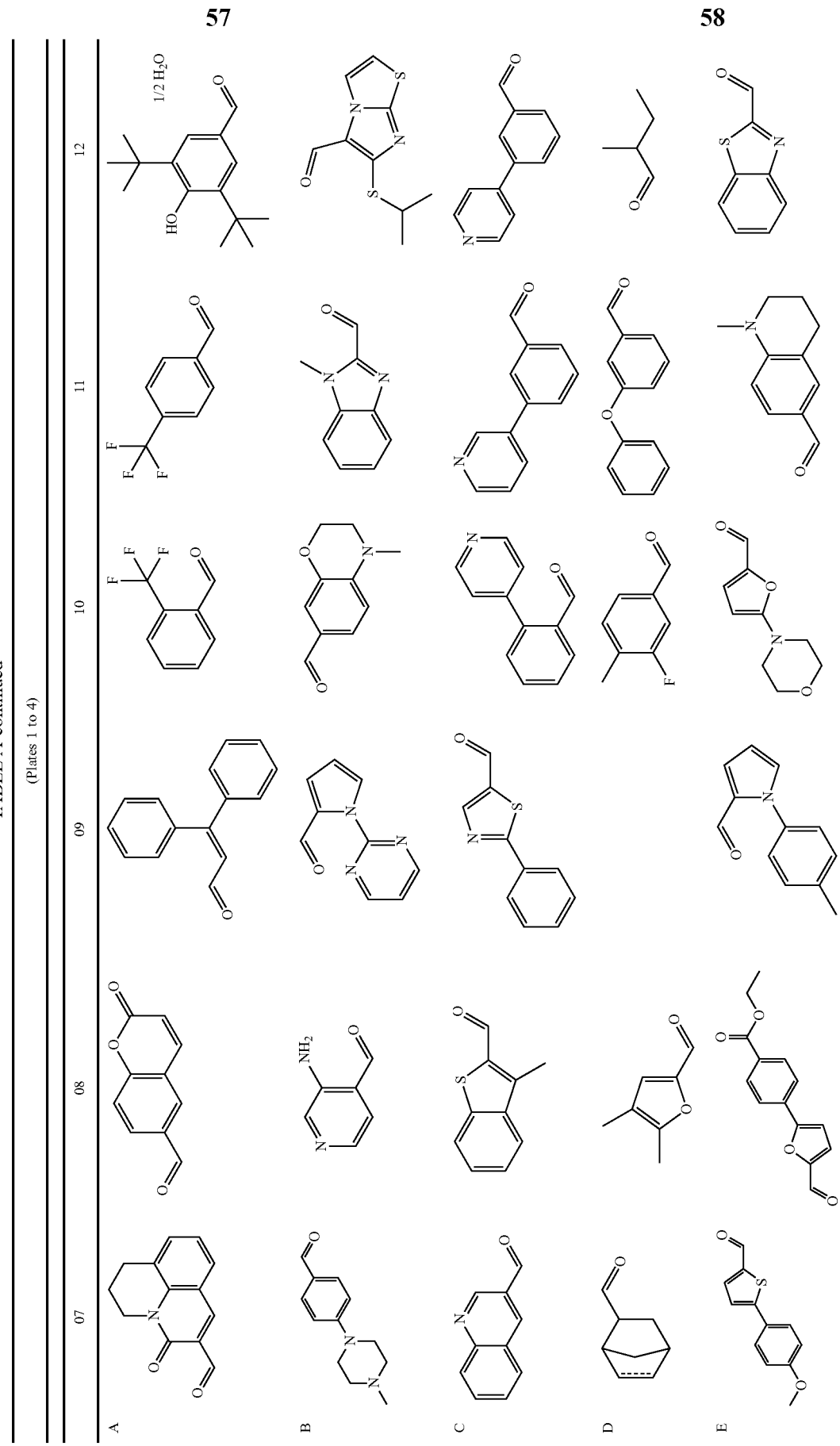

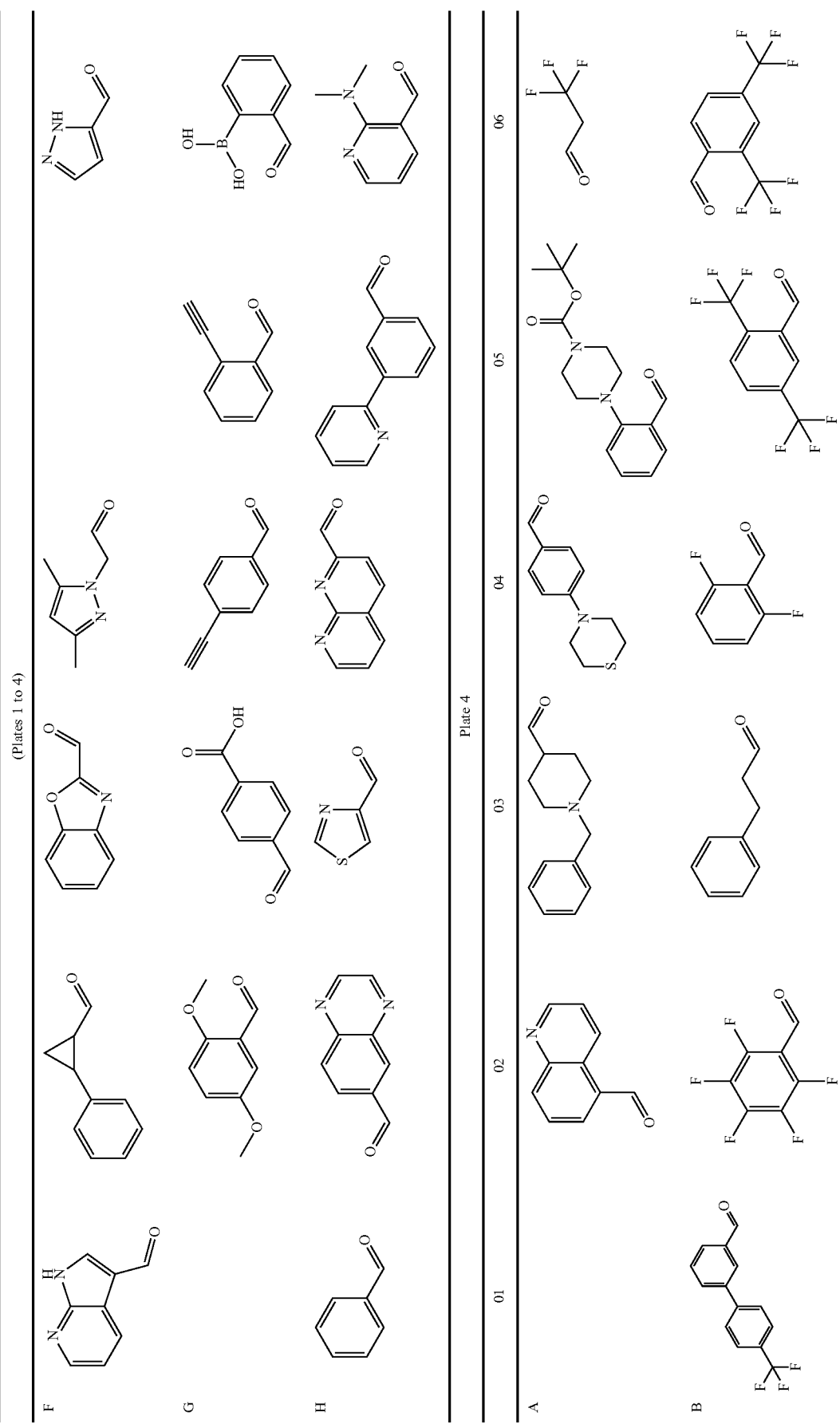

TABLE A-continued
(Plates 1 to 4)
|   | 07 | 08 | 09 | 10 | 11 | 12 |
|---|---|---|---|---|---|---|
| C | | | | | | 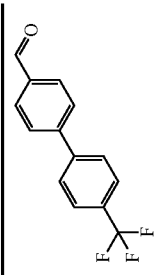 |
| D | | | | | | 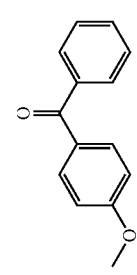 |
| E | | | | | | 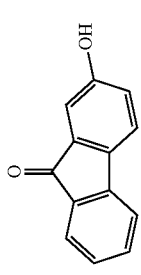 |
| F | | | | | | 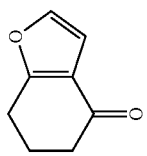 |
| G | | | | | | 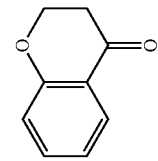 |
| C | | | | | 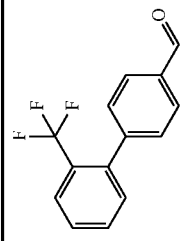 | |
| D | | | | | 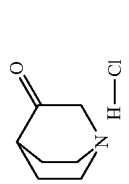 | |
| E | | | | | 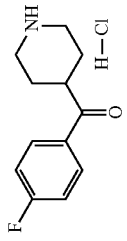 | |
| F | | | | | 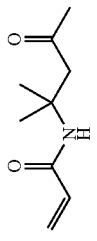 | |
| G | | | | | 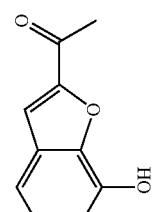 | |
| C | | | | 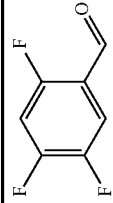 | | |
| D | | | | 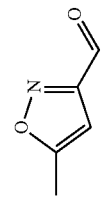 | | |
| E | | | | 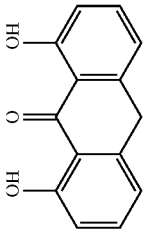 | | |
| F | | | | 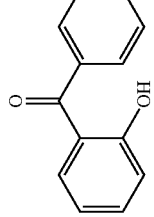 | | |
| C | | | 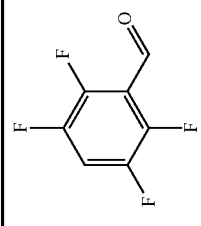 | | | |
| D | | | 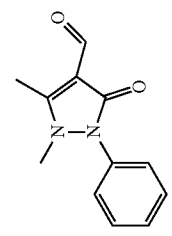 | | | |
| E | | |  | | | |
| F | | | 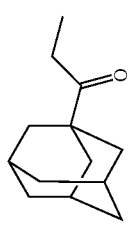 | | | |
| G | | | 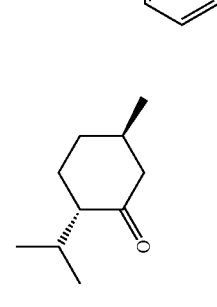 | | | |

TABLE A-continued
(Plates 1 to 4)
| | | | | | |
|---|---|---|---|---|---|
| A | 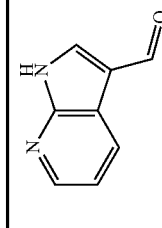 | 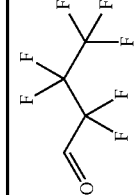 | 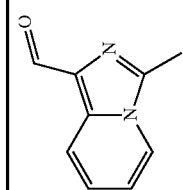 | 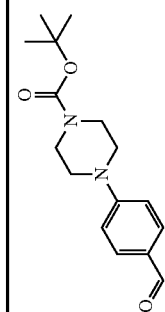 | 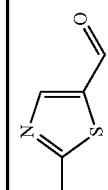 |
| B | 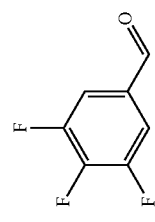 | 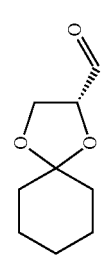 | 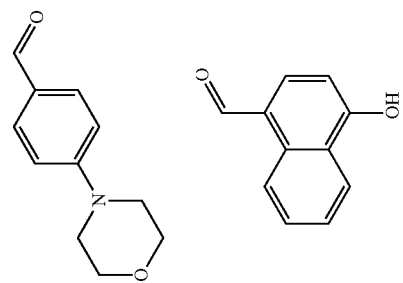 | 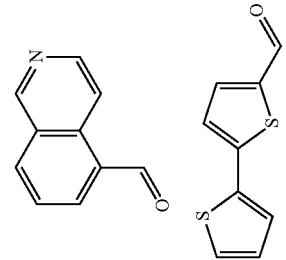 | 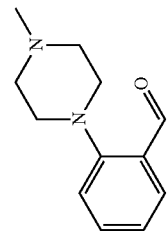 |
| C | 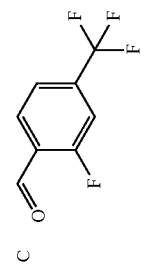 | | | 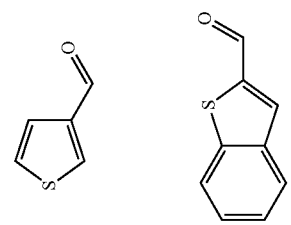 | |
| D | 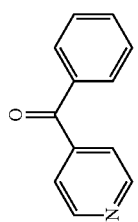 | 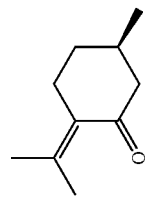 | 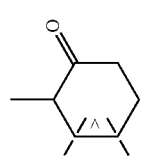 | 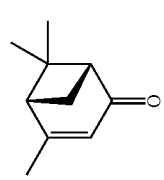 | 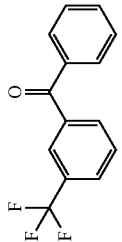 |
| E | 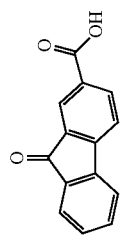 | 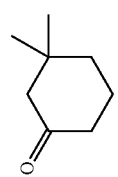 | | 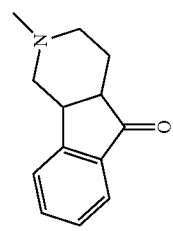 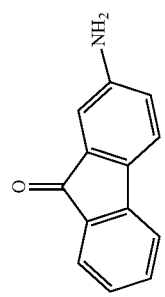 | 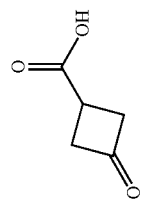 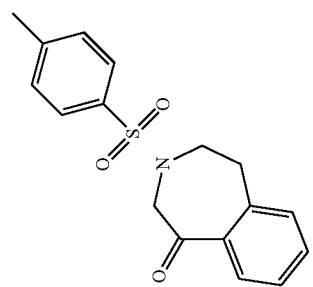 |

TABLE A-continued
(Plates 1 to 4)
| | | | | | |
|---|---|---|---|---|---|
| F |  | 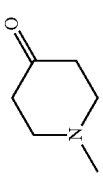 | 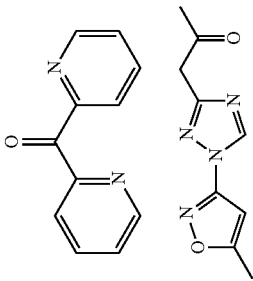 | 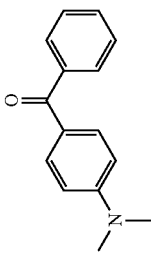 | |
| G | | 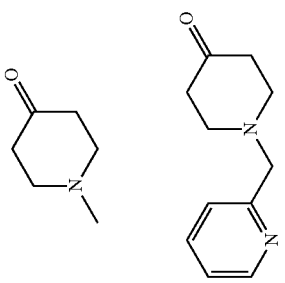 | 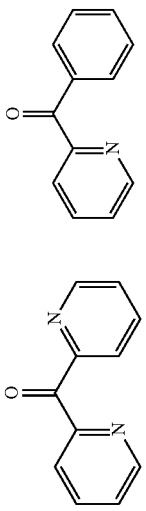 | 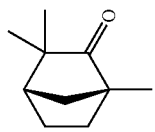 |  |

In some embodiments, a bromodomain or BET inhibitor is a compound represented by the formula:

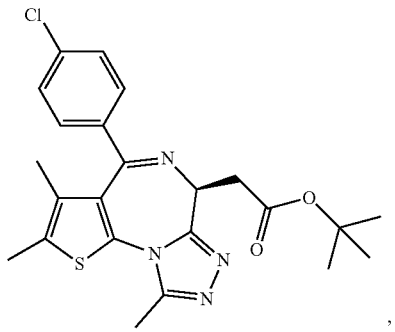 (VIII)

or a salt, solvate, or hydrate thereof. In some embodiments, a bromodomain or BET inhibitor is (racemic) JQ1; in certain embodiments, the compound is (+)-JQ1. In some embodiments, a bromodomain or BET inhibitor is a compound selected from the group consisting of:

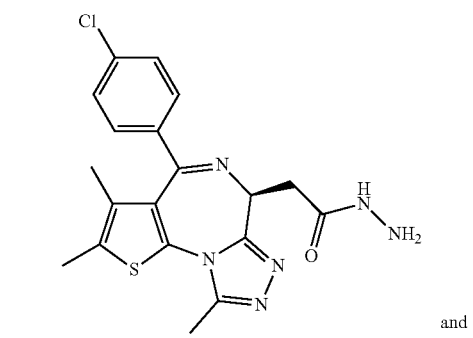 (3)

and

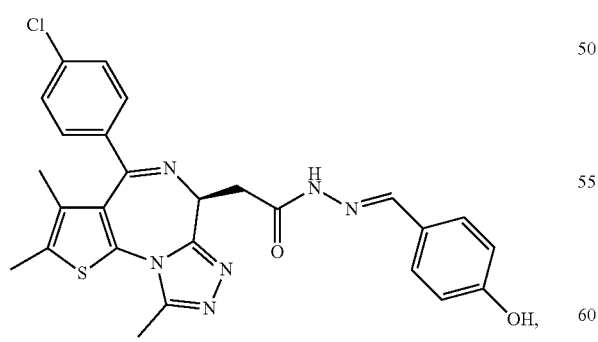 (4)

or a salt, solvate, or hydrate thereof.

Additional examples of compounds include compounds according to any of the following formulae:

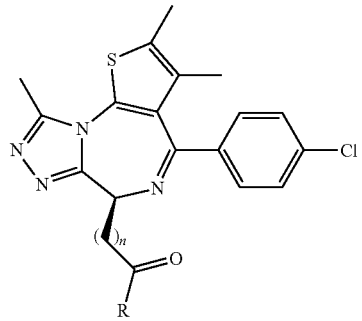 (IX)

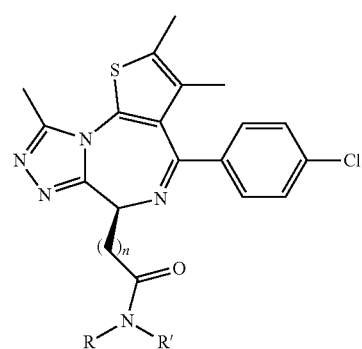 (X)

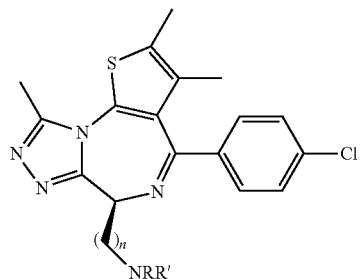 (XI)

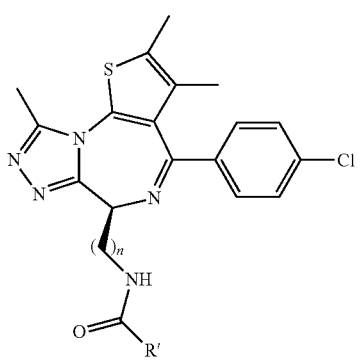 (XII)

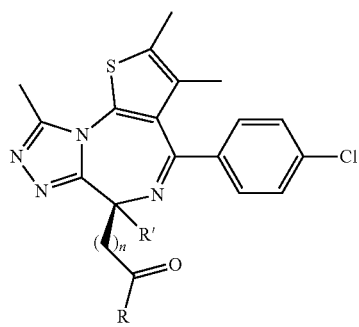
(XIII)
R' = H, D, Me
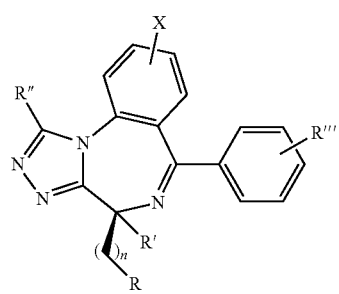
(XIV)
R' = H, D, Me
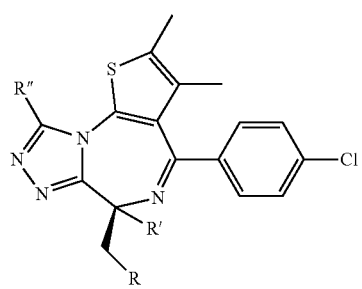
(XV)
R'' = OMe, CH₂OH, CH₂NH₂, CH₂OMe
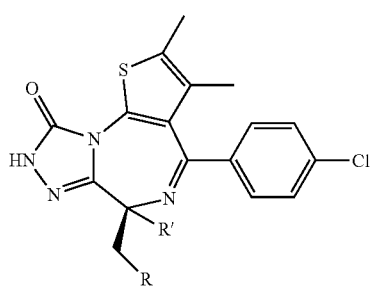
(XVI)
(XVII)
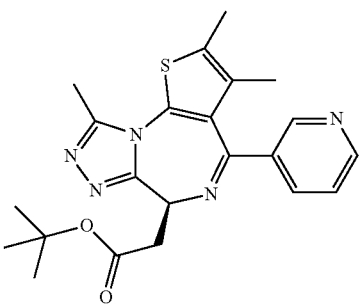
(XVIII)
Also 2- and 4-pyridyl
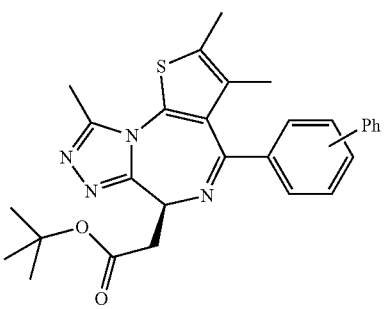
(XIX)
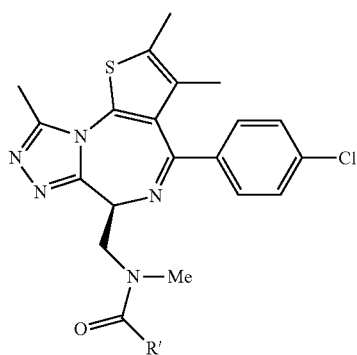
(XX)
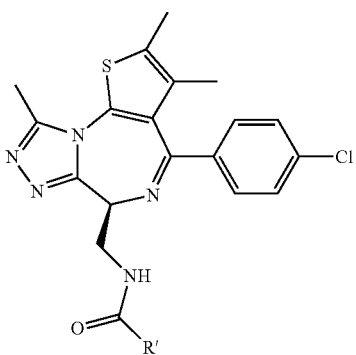
(XXI)

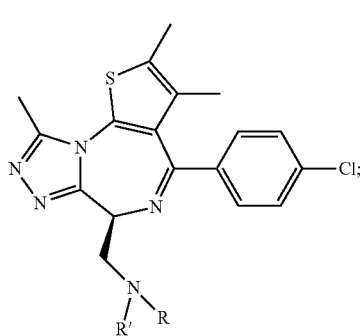

(XXII)

n = 1, 2, 3 or a salt, solvate or hydrate thereof.

In Formulae IX-XXII, R and R' can be, e.g., H, aryl, substituted aryl, heteroaryl, heteroaryl, heterocycloalkyl, —C$_1$-C$_8$ alkyl, —C$_2$-C$_8$ alkenyl, —C$_2$-C$_8$ alkynyl, —C$_3$-Ci$_2$ cycloalkyl, substituted —C$_3$-Ci$_2$ cycloalkyl, —C$_3$-Ci$_2$ cycloalkenyl, or substituted —C$_3$-Ci$_2$ cycloalkenyl, each of which may be optionally substituted. In Formulae XIV, X can be any substituent for an aryl group as described herein.

The compounds described in herein can be prepared using methods well known in the prior art (see, e.g., WO 011143669, the entirety which is incorporated by reference herein).

As used herein, the term an "aromatic ring" or "aryl" means a monocyclic or polycyclic-aromatic ring or ring radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7, 8-tetrahydronaphthyl. An aryl group can be unsubstituted or optionally is substituted with one or more substituents, e.g., substituents as described herein for alkyl groups (including without limitation alkyl (preferably, lower alkyl or alkyl substituted with one or more halo), hydroxy, alkoxy (preferably, lower alkoxy), alkylthio, cyano, halo, amino, boronic acid (—B(OH)2, and nitro). In certain embodiments, the aryl group is a monocyclic ring, wherein the ring comprises 6 carbon atoms.

As used herein, the term "alkyl" means a saturated straight chain or branched non-cyclic hydrocarbon typically having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be unsubstituted, or optionally substituted with one or more substituents, such as amino, alkylamino, arylamino, heteroarylamino, alkoxy, alkylthio, oxo, halo, acyl, nitro, hydroxyl, cyano, aryl, heteroaryl, alkylaryl, alkylheteroaryl, aryloxy, heteroaryloxy, arylthio, heteroarylthio, arylamino, heteroarylamino, carbocyclyl, carbocyclyloxy, carbocyclylthio, carbocyclylamino, heterocyclyl, heterocyclyloxy, heterocyclylamino, heterocyclylthio, and the like. Lower alkyls are typically preferred for the compounds of this invention.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "halogen" designates —F, —Cl, —Br or —I.

The term "haloalkyl" is intended to include alkyl groups as defined above that are mono-, di- or polysubstituted by halogen, e.g., fluoromethyl and trifluoromethyl.

The term "hydroxyl" means —OH.

The term "heteroatom" as used herein means an atom of any element other than carbon or hydrogen. Preferred heteroatoms are nitrogen, oxygen, sulfur and phosphorus.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon. Heteroaryl groups may be optionally substituted with one or more substituents as for aryl groups. Examples of heteroaryl groups include, but are not limited to, pyridyl, furanyl, benzodioxolyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, and indolyl.

The term "heterocyclic" as used herein, refers to organic compounds that contain at least at least one atom other than carbon (e.g., S, O, N) within a ring structure. The ring structure in these organic compounds can be either aromatic or non-aromatic. Some examples of heterocyclic moeities include, are not limited to, pyridine, pyrimidine, pyrrolidine, furan, tetrahydrofuran, tetrahydrothiophene, and dioxane.

The term "isomers" or "stereoisomers" refers to compounds which have identical chemical constitution, but differ with regard to the arrangement of the atoms or groups in space.

The term "isotopic derivatives" includes derivatives of compounds in which one or more atoms in the compounds are replaced with corresponding isotopes of the atoms. For example, an isotopic derivative of a compound containing a carbon atom (C 112") would be one in which the carbon atom of the compound is replaced with the C 13 isotope.

The term "optical isomers" as used herein includes molecules, also known as chiral molecules, that are exact non-superimposable mirror images of one another.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "sulfhydryl" or "thiol" means —SH.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof In some embodiments, the bromodomain inhibitor is any molecule or compound that reduces or prevents expression of BRD-containing proteins. Examples of such inhibitors include siRNA, shRNA, dsRNA, oligomimics, and proteases that target one or more BRD-containing protein.

Methods for producing inhibitors as described above are well known in the art (See e.g., Sambrook, Fritsch and Maniatis, MOLECULAR CLONING: A LABORATORY MANUAL, (Current Edition); CURRENT PROTOCOLS IN MOLECULAR BIOLOGY (F. M. Ausubel et al. eds., (Current Edition)); the series METHODS IN ENZYMOLOGY (Academic Press, Inc.): PCR 2: A PRACTICAL APPROACH (Current Edition) ANTIBODIES, A LABORATORY MANUAL and ANIMAL CELL CULTURE (R. I. Freshney, ed. (1987)). DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); Fundamental Virology, 2nd Edition, vol. I & II (B. N. Fields and D. M. Knipe, eds.).

Examples of bromodomain-containing proteins are shown in Table 2.

TABLE 2

Bromodomain-containing proteins

| Gene | Ensembl gene ID | Ensembl transcript ID | Ensembl protein ID |
|---|---|---|---|
| ASH1L | ENSG00000116539 | ENST00000548830, ENST00000492987, ENST00000392403, ENST00000368346 | ENSP00000449283, ENSP00000448820, ENSP00000376204, ENSP00000357330 |
| ATAD2 | ENSG00000156802 | ENST00000521903, ENST00000519124, ENST00000517666, ENST00000287394 | ENSP00000429213, ENSP00000429617, ENSP00000429331, ENSP00000287394 |
| BAZ1A/B | ENSG00000198604 (A), ENSG00000009954 (B) | ENST00000555331 (A), ENST00000554865 (A), ENST00000553573 (A), ENST00000543083 (A), ENST00000382422 (A), ENST00000360310 (A), ENST00000358716 (A), ENST00000404251 (B), ENST00000339594 (B) | ENSP00000450902 (A), ENSP00000450923 (A), ENSP00000451896 (A), ENSP00000445562 (A), ENSP00000371859 (A), ENSP00000353458 (A), ENSP00000351555 (A), ENSP00000385442 (B), ENSP00000342434 (B) |
| BAZ2A/B | ENSG00000076108 (A), ENSG00000123636 (B) | ENST00000551996 (A), ENST00000551812 (A), ENST00000549884 (A), ENST00000549787 (A), ENST00000549506 (A), ENST00000547650 (A), ENST00000547453 (A), ENST00000546695 (A), ENST00000379441 (A), ENST00000179765 (A), ENST00000546335 (A), ENST00000541068 (B), ENST00000441143 (B), ENST00000437839 (B), ENST00000426648 (B), ENST00000392783 (B), ENST00000392782 (B), ENST00000355831 (B), ENST00000343439 (B), ENST00000294905 (B) | ENSP00000447591 (A), ENSP00000446880 (A), ENSP00000447941 (A), ENSP00000448760 (A), ENSP00000447248 (A), ENSP00000449473 (A), ENSP00000447314 (A), ENSP00000449496 (A), ENSP00000368754 (A), ENSP00000179765 (A), ENSP00000437619 (B), ENSP00000441341 (B), ENSP00000393565 (B), ENSP00000415613 (B), ENSP00000400505 (B), ENSP00000376534 (B), ENSP00000376533 (B), ENSP00000348087 (B), ENSP00000339670 (B), ENSP00000294905 (B) |
| BRD1 | ENSG00000100425 | ENST00000542442, ENST00000457780, ENST00000438393, ENST00000419212, ENST00000404760, ENST00000404034, ENST00000342989, ENST00000216267 | ENSP00000437514, ENSP00000410042, ENSP00000388027, ENSP00000399110, ENSP00000385858, ENSP00000384076, ENSP00000345886, ENSP00000216267 |
| BRD2 | ENSG00000234704, ENSG00000236227, ENSG00000230678, ENSG00000204256, | ENST00000550598, ENST00000547286, ENST00000546777, ENST00000479699, | ENSP00000447012, ENSP00000448429, ENSP00000449979, ENSP00000434155, |

TABLE 2-continued

| Bromodomain-containing proteins | | | |
|---|---|---|---|
| Gene | Ensembl gene ID | Ensembl transcript ID | Ensembl protein ID |
| | ENSG00000234507, ENSG00000235307, ENSG00000215077 | ENST00000450320, ENST00000449118, ENST00000433783, ENST00000427021, ENST00000414731 | ENSP00000413845, ENSP00000399009, ENSP00000416399, ENSP00000400737, ENSP00000391246 |
| BRD3 | ENSG00000169925 | ENST00000540795, ENST00000433041, ENST00000371842, ENST00000371834, ENST00000357885, ENST00000303407 | ENSP00000442302, ENSP00000406749, ENSP00000360908, ENSP00000360900, ENSP00000350557, ENSP00000305918 |
| BRD4 | ENSG00000141867 | ENST00000371835, ENST00000360016, ENST00000263377, | ENSP00000360901, ENSP00000353112, ENSP00000263377 |
| BRDT | ENSG00000137948 | ENST00000552654, ENST00000548992, ENST00000539070, ENST00000457265, ENST00000450792, ENST00000449584, ENST00000448194, ENST00000440509, ENST00000427104, ENST00000426141, ENST00000423434, ENST00000402388, ENST00000399546, ENST00000394530, ENST00000370389, ENST00000362005, ENST00000355011 | ENSP00000446599, ENSP00000447394, ENSP00000441862, ENSP00000408138, ENSP00000414349, ENSP00000408625, ENSP00000410587, ENSP00000416714, ENSP00000400002, ENSP00000404969, ENSP00000396351, ENSP00000384051, ENSP00000387822, ENSP00000378038, ENSP00000359416, ENSP00000354568, ENSP00000400199 |
| BRD7 | ENSG00000166164 | ENST00000569774, ENST00000562383, ENST00000394689, ENST00000394688 | ENSP00000461556, ENSP00000458430, ENSP00000378181, ENSP00000378180 |
| BRD8 | ENSG00000112983 | ENST00000512140, ENST00000511898, ENST00000506167, ENST00000472478, ENST00000455658, ENST00000454473, ENST00000453824, ENST00000450756, ENST00000441656, ENST00000432618, ENST00000430331, ENST00000428808, ENST00000427976, ENST00000418329, ENST00000411594, ENST00000402931, ENST00000254900, ENST00000239899, ENST00000230901 | ENSP00000427475, ENSP00000426385, ENSP00000427126, ENSP00000420884, ENSP00000408396, ENSP00000398067, ENSP00000407129, ENSP00000396487, ENSP00000398084, ENSP00000398676, ENSP00000407414, ENSP00000414625, ENSP00000392646, ENSP00000398873, ENSP00000394330, ENSP00000384845, ENSP00000254900, ENSP00000239899, ENSP00000230901 |
| BRD9 | ENSG00000028310 | ENST00000523139, ENST00000519112, ENST00000518251, ENST00000518250, ENST00000495265, ENST00000490814, ENST00000489816, ENST00000489093, ENST00000487688, ENST00000483173, ENST00000467963, ENST00000466684, ENST00000435709, ENST00000388890, ENST00000323547, ENST00000323510 | ENSP00000430170, ENSP00000429353, ENSP00000428194, ENSP00000430510, ENSP00000420080, ENSP00000417431, ENSP00000419752, ENSP00000420722, ENSP00000420492, ENSP00000419845, ENSP00000419765, ENSP00000420397, ENSP00000402984, ENSP00000373542, ENSP00000325200, ENSP00000323557 |
| BRPF1 | ENSG00000156983 | ENST00000457855, ENST00000433861, ENST00000426583, ENST00000424362, ENST00000420291, | ENSP00000410210, ENSP00000402485, ENSP00000404235, ENSP00000398863, ENSP00000416728, |

TABLE 2-continued

Bromodomain-containing proteins

| Gene | Ensembl gene ID | Ensembl transcript ID | Ensembl protein ID |
|---|---|---|---|
| | | ENST00000383829, | ENSP00000373340, |
| | | ENST00000302054 | ENSP00000306297 |
| BRPF3 | ENSG00000096070 | ENST00000543502, | ENSP00000445352, |
| | | ENST00000534694, | ENSP00000434501, |
| | | ENST00000534400, | ENSP00000436504, |
| | | ENST00000532330, | ENSP00000437087, |
| | | ENST00000527657, | ENSP00000431894, |
| | | ENST00000454960, | ENSP00000413655, |
| | | ENST00000449261, | ENSP00000416842, |
| | | ENST00000446974, | ENSP00000410669, |
| | | ENST00000443324, | ENSP00000387368, |
| | | ENST00000441730, | ENSP00000413022, |
| | | ENST00000441123, | ENSP00000411558, |
| | | ENST00000394572, | ENSP00000378073, |
| | | ENST00000357641, | ENSP00000350267, |
| | | ENST00000339717 | ENSP00000345419 |
| BRWD3 | ENSG00000165288 | ENST00000373275 | ENSP00000362372 |
| CECR2 | ENSG00000099954 | ENST00000400585, | ENSP00000383428, |
| | | ENST00000400573, | ENSP00000383417, |
| | | ENST00000355219, | ENSP00000347357, |
| | | ENST00000342247, | ENSP00000341219, |
| | | ENST00000262608 | ENSP00000262608 |
| CREBBP | ENSG00000005339 | ENST00000573517, | ENSP00000460474, |
| | | ENST00000572134, | ENSP00000458254, |
| | | ENST00000571826, | ENSP00000459490, |
| | | ENST00000570939, | ENSP00000461002, |
| | | ENST00000382070, | ENSP00000371502, |
| | | ENST00000323508, | ENSP00000323550, |
| | | ENST00000262367 | ENSP00000262367 |
| EP300 | ENSG00000100393 | ENST00000263253 | ENSP00000263253 |
| FALZ | aka BPTF: | ENST00000544778, | ENSP00000440854, |
| | ENSG00000262858, | ENST00000544491, | ENSP00000443949, |
| | ENSG00000171634 | ENST00000424123, | ENSP00000388405, |
| | | ENST00000342579, | ENSP00000343837, |
| | | ENST00000335221, | ENSP00000334351, |
| | | ENST00000321892, | ENSP00000315454, |
| | | ENST00000306378, | ENSP00000307208, |
| | | ENST00000576412, | ENSP00000461707, |
| | | ENST00000575874, | ENSP00000459656, |
| | | ENST00000574652, | ENSP00000459309, |
| | | ENST00000574648, | ENSP00000459251, |
| | | ENST00000573838, | ENSP00000458864, |
| | | ENST00000573834, | ENSP00000461014, |
| | | ENST00000571054 | ENSP00000460704 |
| GCN5L2 | aka KAT2A: | ENST00000564173, | ENSP00000456712, |
| | ENSG00000259958, | ENST00000225916 | ENSP00000225916 |
| | ENSG00000108773 | | |
| MLL | ENSG00000118058 | ENST00000534358, | ENSP00000436786, |
| | | ENST00000533790, | ENSP00000436700, |
| | | ENST00000532204, | ENSP00000434618, |
| | | ENST00000531904, | ENSP00000432391, |
| | | ENST00000529852, | ENSP00000436564, |
| | | ENST00000527869, | ENSP00000432652, |
| | | ENST00000392873, | ENSP00000376612, |
| | | ENST00000389507, | ENSP00000374158, |
| | | ENST00000389506, | ENSP00000374157, |
| | | ENST00000359313, | ENSP00000352262, |
| | | ENST00000354520, | ENSP00000346516, |
| | | ENST00000328469 | ENSP00000333556 |
| PB1 | ENSG00000163939 | ENST00000458294, | ENSP00000411895, |
| | | ENST00000450271, | ENSP00000416851, |
| | | ENST00000449505, | ENSP00000412401, |
| | | ENST00000446103, | ENSP00000397662, |
| | | ENST00000439181, | ENSP00000404635, |
| | | ENST00000431678, | ENSP00000409939, |
| | | ENST00000424867, | ENSP00000397399, |
| | | ENST00000423351, | ENSP00000387775, |
| | | ENST00000420148, | ENSP00000389390, |
| | | ENST00000412587, | ENSP00000404579, |
| | | ENST00000410007, | ENSP00000386529, |
| | | ENST00000409767, | ENSP00000386601, |
| | | ENST00000409114, | ENSP00000386643, |
| | | ENST00000409057, | ENSP00000386593, |

TABLE 2-continued

Bromodomain-containing proteins

| Gene | Ensembl gene ID | Ensembl transcript ID | Ensembl protein ID |
| --- | --- | --- | --- |
| | | ENST00000394830, | ENSP00000378307, |
| | | ENST00000356770, | ENSP00000349213, |
| | | ENST00000337303, | ENSP00000338302, |
| | | ENST00000296302 | ENSP00000296302 |
| PCAF | ENSG00000114166 | ENST00000263754 | ENSP00000263754 |
| PHIP | ENSG00000146247 | ENST00000355098, | ENSP00000347215, |
| | | ENST00000275034 | ENSP00000275034 |
| PRKCBP1 | ENSG00000101040 | ENST00000540497, | ENSP00000443086, |
| | | ENST00000536340, | ENSP00000439800, |
| | | ENST00000471951, | ENSP00000420095, |
| | | ENST00000467200, | ENSP00000418495, |
| | | ENST00000461685, | ENSP00000418210, |
| | | ENST00000458360, | ENSP00000392964, |
| | | ENST00000446994, | ENSP00000396725, |
| | | ENST00000446894, | ENSP00000394379, |
| | | ENST00000441977, | ENSP00000393806, |
| | | ENST00000435836, | ENSP00000413727, |
| | | ENST00000396281, | ENSP00000379577, |
| | | ENST00000372023, | ENSP00000361093, |
| | | ENST00000360911, | ENSP00000354166, |
| | | ENST00000355972, | ENSP00000348246, |
| | | ENST00000352431, | ENSP00000335537, |
| | | ENST00000311275, | ENSP00000312237, |
| | | ENST00000262975 | ENSP00000262975 |
| SMARCA2 | ENSG00000080503 | ENST00000457226, | ENSP00000415218, |
| | | ENST00000452193, | ENSP00000401096, |
| | | ENST00000450198, | ENSP00000392081, |
| | | ENST00000439732, | ENSP00000409398, |
| | | ENST00000423555, | ENSP00000413057, |
| | | ENST00000417599, | ENSP00000387486, |
| | | ENST00000416751, | ENSP00000412242, |
| | | ENST00000382203, | ENSP00000371638, |
| | | ENST00000382194, | ENSP00000371629, |
| | | ENST00000382186, | ENSP00000371621, |
| | | ENST00000382185, | ENSP00000371620, |
| | | ENST00000382183, | ENSP00000371618, |
| | | ENST00000382182, | ENSP00000371617, |
| | | ENST00000357248, | ENSP00000349788, |
| | | ENST00000349721, | ENSP00000265773, |
| | | ENST00000324954, | ENSP00000324770, |
| | | ENST00000302401 | ENSP00000305411 |
| SMARCA4 | ENSG00000127616 | ENST00000541122, | ENSP00000445036, |
| | | ENST00000538456, | ENSP00000443848, |
| | | ENST00000450717, | ENSP00000397783, |
| | | ENST00000444061, | ENSP00000392837, |
| | | ENST00000429416, | ENSP00000395654, |
| | | ENST00000421844, | ENSP00000403803, |
| | | ENST00000413806, | ENSP00000414727, |
| | | ENST00000358026, | ENSP00000350720, |
| | | ENST00000344626 | ENSP00000343896 |
| SP100 | ENSG00000067066 | ENST00000452345, | ENSP00000416563, |
| | | ENST00000432979, | ENSP00000391616, |
| | | ENST00000431952, | ENSP00000393679, |
| | | ENST00000427101, | ENSP00000399389, |
| | | ENST00000414648, | ENSP00000412837, |
| | | ENST00000413284, | ENSP00000400277, |
| | | ENST00000409897, | ENSP00000386998, |
| | | ENST00000409824, | ENSP00000387311, |
| | | ENST00000409341, | ENSP00000386404, |
| | | ENST00000409112, | ENSP00000386427, |
| | | ENST00000341950, | ENSP00000342729, |
| | | ENST00000340126, | ENSP00000343023, |
| | | ENST00000264052 | ENSP00000264052 |
| SP110 | ENSG00000135899 | ENST00000540870, | ENSP00000439558, |
| | | ENST00000455674, | ENSP00000393992, |
| | | ENST00000416610, | ENSP00000399978, |
| | | ENST00000409815, | ENSP00000387172, |
| | | ENST00000392048, | ENSP00000375902, |
| | | ENST00000358662, | ENSP00000351488, |
| | | ENST00000338556, | ENSP00000344049, |
| | | ENST00000258382, | ENSP00000258382, |
| | | ENST00000258381 | ENSP00000258381 |
| SP140 | ENSG00000079263 | ENST00000537563, | ENSP00000445084, |
| | | ENST00000486687, | ENSP00000440107, |
| | | ENST00000420434, | ENSP00000398210, |
| | | ENST00000417495, | ENSP00000393618, |

TABLE 2-continued

Bromodomain-containing proteins

| Gene | Ensembl gene ID | Ensembl transcript ID | Ensembl protein ID |
| --- | --- | --- | --- |
| | | ENST00000392045, | ENSP00000375899, |
| | | ENST00000392044, | ENSP00000375898, |
| | | ENST00000373645, | ENSP00000362749, |
| | | ENST00000350136, | ENSP00000345846, |
| | | ENST00000343805 | ENSP00000342096 |
| TAF1 | ENSG00000147133 | ENST00000538124, | ENSP00000441908, |
| | | ENST00000483985, | ENSP00000424526, |
| | | ENST00000463163, | ENSP00000421611, |
| | | ENST00000449580, | ENSP00000389000, |
| | | ENST00000437147, | ENSP00000406517, |
| | | ENST00000423759, | ENSP00000406549, |
| | | ENST00000395779, | ENSP00000379125, |
| | | ENST00000373790, | ENSP00000362895, |
| | | ENST00000373775, | ENSP00000362880, |
| | | ENST00000276072 | ENSP00000276072 |
| TAF1L | ENSG00000122728 | ENST00000242310 | ENSP00000418379 |
| TRIM24 | ENSG00000122779 | ENST00000536822, | ENSP00000440535, |
| | | ENST00000452999, | ENSP00000402079, |
| | | ENST00000439939, | ENSP00000403347, |
| | | ENST00000415680, | ENSP00000390829, |
| | | ENST00000378381, | ENSP00000367632, |
| | | ENST00000343526 | ENSP00000340507 |
| TRIM28 | ENSG00000130726 | ENST00000341753, | ENSP00000342232, |
| | | ENST00000253024 | ENSP00000253024 |
| TRIM33 | ENSG00000197323 | ENST00000450349, | ENSP00000412077, |
| | | ENST00000448034, | ENSP00000402333, |
| | | ENST00000369543, | ENSP00000358556, |
| | | ENST00000358465 | ENSP00000351250 |
| TRIM66 | ENSG00000166436 | ENST00000530502, | ENSP00000437234, |
| | | ENST00000402157, | ENSP00000384876, |
| | | ENST00000299550 | ENSP00000299550 |
| WDR9 | ENSG00000185658 | ENST00000455867, | ENSP00000389882, |
| | | ENST00000446924, | ENSP00000391014, |
| | | ENST00000445668, | ENSP00000395575, |
| | | ENST00000445245, | ENSP00000390684, |
| | | ENST00000430093, | ENSP00000393702, |
| | | ENST00000424441, | ENSP00000415066, |
| | | ENST00000412604, | ENSP00000398900, |
| | | ENST00000380800, | ENSP00000370178, |
| | | ENST00000380783, | ENSP00000370160, |
| | | ENST00000342449, | ENSP00000344333, |
| | | ENST00000341322, | ENSP00000342106, |
| | | ENST00000333229 | ENSP00000330753 |
| ZMYND11 | ENSG00000015171, | ENST00000545619, | ENSP00000438461, |
| | ENSG00000260150 | ENST00000535374, | ENSP00000439587, |
| | | ENST00000509513, | ENSP00000424205, |
| | | ENST00000439456, | ENSP00000397072, |
| | | ENST00000403354, | ENSP00000385484, |
| | | ENST00000402736, | ENSP00000386010, |
| | | ENST00000397962, | ENSP00000381053, |
| | | ENST00000397959, | ENSP00000381050, |
| | | ENST00000397955, | ENSP00000381046, |
| | | ENST00000381607, | ENSP00000371020, |
| | | ENST00000381604, | ENSP00000371017, |
| | | ENST00000381602, | ENSP00000371015, |
| | | ENST00000381591, | ENSP00000371003, |
| | | ENST00000381584, | ENSP00000370996, |
| | | ENST00000309776, | ENSP00000309992, |
| | | ENST00000568927, | ENSP00000458138, |
| | | ENST00000568174, | ENSP00000457204, |
| | | ENST00000565311, | ENSP00000457248, |
| | | ENST00000564303, | ENSP00000456325, |
| | | ENST00000563851, | ENSP00000456634, |
| | | ENST00000562898, | ENSP00000454775, |
| | | ENST00000562457 | ENSP00000455330 |

In some embodiments, "inhibit", "block", "suppress" or "prevent" means that the activity being inhibited, blocked, suppressed, or prevented is reduced by at least 5%, 10%, 15%, 20%, 25%, 30%, 35%, 40%, 45%, 50%, 55%, 60%, 65%, 70%, 75%, 80%, 85%, 90%, 95%, or 100% as compared to the activity of a control (e.g., activity in the absence of the inhibitor). In some embodiments, "inhibit", "block", "suppress" or "prevent" means that the expression of the target of the inhibitor (e.g. a bromodomain-containing protein) is reduced by at least 5%, 10%, 15%, 20%, 25%, 30%, 35%, 40%, 45%, 50%, 55%, 60%, 65%, 70%, 75%, 80%, 85%, 90%, 95%, 100% as compared to a control (e.g., the expression in the absence of the inhibitor).

Notch Pathway Inhibitors

A Notch pathway inhibitor prevents or inhibits, in part or in whole, the activity of components of the Notch pathway. It is to be understood that the activity of components of the Notch pathway may include one or more activities, such as cell fate specification, differentiation, proliferation, apoptosis, adhesion, epithelial-mesenchymal transition, migration, or angiogenesis. In some embodiments, a Notch pathway inhibitor suppresses or inhibits a Notch pathway activation mutation. Examples of Notch pathway activation mutations are described below. Notch pathway inhibitors are known in the art. In some embodiments, a Notch pathway inhibitor is a gamma secretase inhibitor (GSI). Gamma secretase is a multi-subunit protease complex that cleaves Notch. This cleavage releases Notch from the cell membrane, allowing Notch to enter the nucleus and modify gene expression.

Examples of gamma secretase inhibitors include, but are not limited to, DBZ (Axon Medchem, Cat. No. 1488), BMS-906024 (Bristol-Myers Squibb), RO4929097 (Roche/Genentech), LY450139 (Eli Lilly), BMS-708163 (Bristol-Myers Squibb), MK-0752 (University of Michigan), PF-03084014 (Pfizer), IL-X (also referred to as cbz-IL-CHO, Calbiochem), z-Leu-leu-Nle-CHO (EMD Millipore), N—[N-(3,5-difluorophenacetyl)-L-alanyl]-Sphenylglycine t-butyl ester (DAPT), BH589 (Panobinostat, Novartis), MEDI0639 (MedImmune LLC), Choline magnesium trisalicylate (e.g., Trilisate), and Curcumin (a curcuminoid of turmeric).

Other Notch pathway inhibitors include antibodies and antibody fragments. Examples include monoclonal antibodies against extracellular Notch receptors (developed by Genentech and described by Wu et al. Nature 2010). Another example is a stapled peptide inhibitor of the intracellular Notch transcriptional complex (SAHM1) described by Moellering et al. Nature, 2009 (being developed by Aileron Therapeutics).

In some embodiments, a Notch pathway inhibitor is any molecule or compound that reduces or prevents (mRNA or protein) expression of any component of the Notch pathway (e.g. Notch, Notch ligands, downstream effectors, and the like). Examples of such inhibitors include siRNA, shRNA, dsRNA, oligomimics, and proteases that target one or more components of the Notch pathway. Components of the Notch pathway include, but are not limited to, those in Table 3.

TABLE 3

| Notch pathway components | | | |
|---|---|---|---|
| Gene | Ensembl gene ID | Ensembl transcript ID | Ensembl protein ID |
| ADAM17 | ENSG00000151694 | ENST00000310823, ENST00000497134, ENST00000538558, ENST00000478059 | ENSP00000309968, ENSP00000418728, ENSP00000439780 |
| AKT1 | ENSG00000142208 | ENST00000349310,ENST00000407796,ENST00000402615,ENST00000554848,ENST00000554581,ENST00000555528,ENST00000544168,ENST00000554192,ENST00000555380,ENST00000555926,ENST00000555458 | ENSP00000270202,ENSP00000384293,ENSP00000385326,ENSP00000451166,ENSP00000451828,ENSP0000450688,ENSP00000443897,ENSP00000450681,ENSP00000451290,ENSP00000451824,ENSP00000451470 |
| APH1A | ENSG00000117362 | ENST00000360244,ENST00000369109,ENST00000236017,ENST00000414276 | ENSP00000353380,ENSP00000358105,ENSP00000236017,ENSP00000397473 |
| APH1B | ENSG00000138613 | ENST00000261879,ENST00000380343,ENST00000560353,ENST00000560890,ENST00000380340,ENST00000559971 | ENSP00000261879,ENSP00000369700,ENSP00000453327,ENSP00000453002,ENSP00000369697,ENSP00000453516 |
| CDKN1A | ENSG00000124762 | ENST00000244741,ENST00000373711,ENST00000405375,ENST00000448526 | ENSP00000244741,ENSP00000362815,ENSP00000384849,ENSP00000409259 |
| CIR1 | ENSG00000138433 | ENST00000342016,ENST00000377973,ENST00000414336,ENST00000362053,ENST00000425101 | ENSP00000339723,ENSP00000367211,ENSP00000395036,ENSP00000355034,ENSP00000405693 |
| CUL1 | ENSG00000055130 | ENST00000409469,ENST00000325222,ENST00000433865,ENST00000543583 | ENSP00000387160,ENSP00000326804,ENSP00000396011,ENSP00000441340 |

TABLE 3-continued

| Notch pathway components | | | |
|---|---|---|---|
| Gene | Ensembl gene ID | Ensembl transcript ID | Ensembl protein ID |
| DLL1 | ENSG00000198719 | ENST00000366756 | ENSP00000355718 |
| DLL3 | ENSG00000090932 | ENST00000205143, ENST00000356433 | ENSP00000205143, ENSP00000348810 |
| DLL4 | ENSG00000128917 | ENST00000249749 | ENSP00000249749 |
| DTX1 | ENSG00000135144 | ENST00000257600 | ENSP00000257600 |
| EP300 | ENSG00000100393 | ENST00000263253 | ENSP00000263253 |
| FBXW7 | ENSG00000109670 | ENST00000263981,ENST00000281708,ENST00000296555,ENST00000393956 | ENSP00000263981,ENSP00000281708,ENSP00000296555,ENSP00000377528 |
| FHL1 | ENSG00000022267 | ENST00000370690,ENST00000345434,ENST00000370676,ENST00000370683,ENST00000420362,ENST00000370674,ENST00000452016,ENST00000434885,ENST00000458357,ENST00000456445,ENST00000449474,ENST00000394153, ENST00000394155,ENST00000456218,ENST00000535737,ENST00000536581,ENST00000539015,ENST00000542704,ENST00000543669 | ENSP00000359724,ENSP00000071281,ENSP00000359710,ENSP00000359717,ENSP00000391779,ENSP00000359708,ENSP00000408038,ENSP00000413798,ENSP00000389920,ENSP00000412642,ENSP00000414604,ENSP00000377709,ENSP00000377710,ENSP00000392813,ENSP00000444815, ENSP00000445335, ENSP00000437673,ENSP00000446441,ENSP00000443333 |
| GATA3 | ENSG00000107485 | ENST00000379328,ENST00000346208,ENST00000544011 | ENSP00000368632,ENSP00000341619,ENSP00000439641 |
| GSK3B | ENSG00000082701 | ENST00000264235,ENST00000316626,ENST00000539838 | ENSP00000264235,ENSP00000324806,ENSP00000437981 |
| HAT1 | ENSG00000128708 | ENST00000264108,ENST00000392584,ENST00000412731,ENST00000457761 | ENSP00000264108,ENSP00000376363,ENSP00000407921,ENSP00000403466 |
| HDAC1 | ENSG00000116478 | ENST00000373548, ENST00000428704, ENST00000373541 | ENSP00000362649, ENSP00000407859, ENSP00000362642 |
| HDAC10 | ENSG00000100429 | ENST00000216271,ENST00000448072,ENST00000349505,ENST00000415993,ENST00000429374,ENST00000454936 | ENSP00000216271,ENSP00000397542,ENSP00000343540,ENSP00000397517,ENSP00000407640,ENSP00000406150 |
| HDAC11 | ENSG00000163517 | ENST00000295757,ENST00000433119,ENST00000402259,ENST00000402271,ENST00000404040,ENST00000404548,ENST00000405025,ENST00000405478,ENST00000458642,ENST00000418189,ENST00000434848,ENST00000416248, ENST00000455904,ENST00000437379,ENST00000522202,ENST00000446613,ENST00000425430 | ENSP00000295757,ENSP00000412514,ENSP00000384706,ENSP00000384123,ENSP00000385475,ENSP00000385528,ENSP00000384019,ENSP00000385252,ENSP00000405403,ENSP00000411792,ENSP00000398651,ENSP00000402298,ENSP00000396122,ENSP00000395188,ENSP00000429794,ENSP00000401487,ENSP00000399792 |
| HDAC2 | ENSG00000196591 | ENST00000519065,ENST00000425835,ENST00000368632,ENST00000519108,ENST00000518690,ENST00000523240,ENST00000521610,ENST00000524334,ENST00000520895,ENST00000523628,ENST00000522371,ENST00000521163, ENST00000398283 | ENSP00000430432,ENSP00000417026,ENSP00000357621,ENSP00000430008,ENSP00000428653,ENSP00000429236,ENSP00000429901,ENSP00000428989,ENSP00000428861,ENSP00000427861,ENSP00000428599,ENSP00000428024,ENSP00000381331 |

TABLE 3-continued

Notch pathway components

| Gene | Ensembl gene ID | Ensembl transcript ID | Ensembl protein ID |
| --- | --- | --- | --- |
| HDAC3 | ENSG00000171720 | ENST00000305264,ENST00000523088,ENST00000523353,ENST00000519474 | ENSP00000302967,ENSP00000429099,ENSP00000430667,ENSP00000430782 |
| HDAC4 | ENSG00000068024 | ENST00000345617,ENST00000446876,ENST00000454542,ENST00000445704,ENST00000430200,ENST00000544989,ENST00000393621,ENST00000456922,ENST00000541256,ENST00000543185 | ENSP00000264606,ENSP00000392912,ENSP00000405226,ENSP00000391226,ENSP00000410551,ENSP00000438111,ENSP00000377243,ENSP00000406618,ENSP00000443057,ENSP00000440481 |
| HDAC5 | ENSG00000108840 | ENST00000225983,ENST00000336057,ENST00000393622 | ENSP00000225983,ENSP00000337290,ENSP00000377244 |
| HDAC6 | ENSG00000094631 | ENST00000334136,ENST00000376643,ENST00000426196,ENST00000430858,ENST00000376619,ENST00000423941,ENST00000438518,ENST00000376610,ENST00000441703,ENST00000443563,ENST00000440653,ENST00000413163, ENST00000436813,ENST00000444343 | ENSP00000334061,ENSP00000365831,ENSP00000402189,ENSP00000397697,ENSP00000365804,ENSP00000392815,ENSP00000403370,ENSP00000365795,ENSP00000393916,ENSP00000402751,ENSP00000394377,ENSP00000398801,ENSP00000405449,ENSP00000398566 |
| HDAC7 | ENSG00000061273 | ENST00000080059,ENST00000354334,ENST00000417107,ENST00000450805,ENST00000433685,ENST00000447463,ENST00000427332,ENST00000434070,ENST00000445237,ENST00000421231,ENST00000417902,ENST00000430670, ENST00000440293,ENST00000422254,ENST00000552960,ENST00000380610,ENST00000548080,ENST00000548938,ENST00000547259,ENST00000425451,ENST00000485796,ENST00000551602,ENST00000477203 | ENSP00000080059,ENSP00000351326,ENSP00000387792,ENSP00000397236,ENSP00000403149,ENSP00000389501,ENSP00000404394,ENSP00000388561,ENSP00000390415,ENSP00000412155,ENSP00000400811,ENSP00000396159,ENSP00000411058,ENSP00000410068,ENSP00000448532,ENSP00000369984,ENSP00000446538,ENSP00000448305,ENSP00000447191,ENSP00000401872,ENSP00000448448,ENSP00000449193,ENSP00000449171 |
| HDAC8 | ENSG00000147099 | ENST00000373573,ENST00000439122,ENST00000373556,ENST00000373571,ENST00000373554,ENST00000373568,ENST00000373560,ENST00000373559,ENST00000421523,ENST00000373583,ENST00000415409,ENST00000373561, ENST00000373589,ENST00000429103,ENST00000412342,ENST00000444609,ENST00000436675 | ENSP00000362674,ENSP00000414486,ENSP00000362657,ENSP00000362672,ENSP00000362655,ENSP00000362669,ENSP00000362661,ENSP00000362660,ENSP00000398997,ENSP00000362685,ENSP00000396424,ENSP00000362662,ENSP00000362691,ENSP00000388459,ENSP00000400180,ENSP00000409778,ENSP00000416489 |
| HDAC9 | ENSG00000048052 | ENST00000406451,ENST00000405010,ENST00000406072,ENST00000417496,ENST00000433709,ENST00000413509,ENST00000430454,ENST00000413380,ENST0 | ENSP00000384657,ENSP00000384382,ENSP00000384017,ENSP00000401669,ENSP00000409003,ENSP00000412497,ENSP00000411422,ENSP000 |

TABLE 3-continued

Notch pathway components

| Gene | Ensembl gene ID | Ensembl transcript ID | Ensembl protein ID |
|---|---|---|---|
| | | 0000441986,ENST0000 0456174,ENST0000040 1921,ENST0000044154 2,ENST00000524023,E NST00000432645,ENST 00000428307,ENST000 00262069,ENST000003 41009,ENST000004466 46 | 00392564,ENSP0000 0404763,ENSP00000 388568,ENSP000003 83912,ENSP0000040 8617,ENSP00000430 036,ENSP000004103 37,ENSP0000039565 5,EN5P00000262069, ENSP00000339165,E NSP00000415095 |
| HES1 | ENSG00000114315 | ENST00000232424 | ENSP00000232424 |
| HES5 | ENSG00000197921 | ENST00000378453 | ENSP00000367714 |
| HES6 | ENSG00000144485 | ENST00000272937,ENS T00000409002,ENST00 000409160,ENST00000 436051,ENST00000409 574,ENST00000409182, ENST00000409356,EN ST00000450098,ENST0 0000417803 | ENSP00000272937,E NSP00000387155,EN SP00000387215,ENS P00000392596,ENSP 00000387008,ENSP0 0000387343,ENSP00 000387107,ENSP000 00390870,ENSP0000 0401797 |
| HEY1 | ENSG00000164683 | ENST00000354724,ENS T00000523976,ENST00 000518733,ENST00000 337919,ENST00000542 205 | ENSP00000346761,E NSP00000429792,EN SP00000429705,ENS P00000338272,ENSP 00000445025 |
| HEY2 | ENSG00000135547 | ENST00000368364, ENST00000368365 | ENSP00000357348, ENSP00000357349 |
| HIF1A | ENSG00000100644 | ENST00000337138,ENS T00000323441,ENST00 000394997,ENST00000 557538,ENST00000394 988,ENST00000539097, ENST00000539494 | ENSP00000338018,E NSP00000323326,EN SP00000378446,ENS P00000451696,ENSP 00000378439,ENSP0 0000437955,ENSP00 000446436 |
| ITCH | ENSG00000078747 | ENST00000374864,ENS T00000262650,ENST00 000535650 | ENSP00000363998,E NSP00000262650,EN SP00000445608 |
| JAG1 | ENSG00000101384 | ENST00000254958, ENST00000423891 | ENSP00000254958, ENSP00000389519 |
| JAG2 | ENSG00000184916 | ENST00000331782, ENST00000347004 | ENSP00000328169, ENSP00000328566 |
| JAK2 | ENSG00000096968 | ENST00000381652,ENS T00000539801,ENST00 000544510 | ENSP00000371067,E NSP00000440387,EN SP00000443103 |
| LCK | ENSG00000182866 | ENST00000336890,ENS T00000482949,ENST00 000333070,ENST00000 495610,ENST00000373 557,ENST00000477031, ENST00000461712,EN ST00000373562,ENST0 0000373564,ENST0000 0398345,ENST0000043 6824 | ENSP00000337825,E NSP00000431517,EN SP00000328213,ENS P00000435605,ENSP 00000362658,ENSP0 0000436554,ENSP00 000434525,ENSP000 00362663,ENSP0000 0362665,ENSP00000 381387,ENSP000004 00092 |
| LFNG | ENSG00000106003 | ENST00000222725,ENS T00000359574,ENST00 000402506,ENST00000 402045,ENST00000338 732 | ENSP00000222725,E NSP00000352579,EN SP00000385764,ENS P00000384786,ENSP 00000343095 |
| MAGEA1 | ENSG00000198681 | ENST00000356661 | ENSP00000349085 |
| MAML1 | ENSG00000161021 | ENST00000292599, ENST00000376951 | ENSP00000292599, ENSP00000366150 |
| MAML2 | ENSG00000184384 | ENST00000524717, ENST00000440572 | ENSP00000434552, ENSP00000412394 |
| MAML3 | ENSG00000196782 | ENST00000509479,ENS T00000502696,ENST00 000327122,ENST00000 398940,ENST00000538 400 | ENSP00000421180,E NSP00000422783,EN SP00000313316,ENS P00000381913,ENSP 00000444397 |
| MFNG | ENSG00000100060 | ENST00000356998,ENS T00000442496,ENST00 000436341,ENST00000 424765,ENST00000454 291,ENST00000416983, | ENSP00000349490,E NSP00000389274,EN SP00000394081,ENS P00000407110,ENSP 00000407094,ENSP0 |

TABLE 3-continued

Notch pathway components

| Gene | Ensembl gene ID | Ensembl transcript ID | Ensembl protein ID |
|---|---|---|---|
| | | ENST00000450946,ENST00000430411,ENST00000438891 | 0000413855,ENSP00000396605,ENSP00000414342,ENSP00000414222 |
| MTOR | ENSG00000198793 | ENST00000361445,ENST00000376838,ENST00000455339,ENST00000539766 | ENSP00000354558,ENSP00000366034,ENSP00000398745,ENSP00000440730 |
| MYC | ENSG00000136997 | ENST00000377970,ENST00000259523,ENST00000517291,ENST00000524013,ENST00000520751,ENST00000454617 | ENSP00000367207,ENSP00000259523,ENSP00000429441,ENSP00000430235,ENSP00000430226,ENSP0000405312 |
| NCOR1 | ENSG00000141027 | ENST00000268712,ENST00000436828,ENST00000395851,ENST00000395849,ENST00000436068,ENST00000395848,ENST00000411510,ENST00000430577,ENST00000395857,ENST00000458113 | ENSP00000268712,ENSP00000387727,ENSP00000379192,ENSP00000379190,ENSP00000389839,ENSP0000379189,ENSP00000407998,ENSP00000410784,ENSP00000379198,ENSP00000395091 |
| NCOR2 | ENSG00000196498 | ENST00000429285,ENST00000404621,ENST00000458234,ENST00000420698,ENST00000405201,ENST00000448614,ENST00000453428,ENST00000440187,ENST00000440337,ENST00000418829,ENST00000413172,ENST00000448008,ENST00000443451,ENST00000542927,ENST00000356219,ENST00000397355,ENST00000404121,ENST00000447011,ENST00000447675 | ENSP00000400281,ENSP00000384202,ENSP00000402808,ENSP00000405367,ENSP00000384018,ENSP0000408247,ENSP00000400687,ENSP00000396044,ENSP00000398963,ENSP00000391389,ENSP00000407357,ENSP00000403034,ENSP00000405246,ENSP00000443689,ENSP00000348551, ENSP00000380513, ENSP00000385618,ENSP00000396746,ENSP00000401058 |
| NCSTN | ENSG00000162736 | ENST00000294785,ENST00000368063,ENST00000438008,ENST00000421914,ENST00000437169,ENST00000424645,ENST00000435149,ENST00000424754,ENST00000368065,ENST00000368067,ENST00000392212,ENST00000535857 | ENSP00000294785,ENSP00000357042,ENSP00000389370,ENSP00000390409,ENSP00000415442,ENSP0000388118,ENSP00000407849,ENSP00000410124,ENSP00000357044,ENSP00000357046,ENSP00000376047,ENSP00000442605 |
| NFKB1 | ENSG00000109320 | ENST00000226574,ENST00000394820,ENST00000505458,ENST00000507079,ENST00000511926,ENST00000509165,ENST00000508584 | ENSP00000226574,ENSP00000378297,ENSP00000424790,ENSP00000426147,ENSP00000420904,ENSP00000423877,ENSP00000424815 |
| NOTCH1 | ENSG00000148400 | ENST00000277541 | ENSP00000277541 |
| NOTCH2 | ENSG00000134250 | ENST00000256646,ENST00000369342,ENST00000401649,ENST00000538680,ENST00000539617 | ENSP00000256646,ENSP00000358348,ENSP00000384752,ENSP00000439516,ENSP00000438937 |
| NOTCH3 | ENSG00000074181 | ENST00000263388, ENST00000539383 | ENSP00000263388, ENSP00000446150 |
| NOTCH4 | ENSG00000204301 | ENST00000375023, ENST00000443903 | ENSP00000364163, ENSP00000398123 |
| NUMB | ENSG00000133961 | ENST00000554546,ENST00000555394,ENST00000557597,ENST00000555238,ENST00000356296,ENST00000556772, | ENSP00000452416,ENSP00000451625,ENSP00000451117,ENSP00000451300,ENSP00000348644,ENSP0 |

TABLE 3-continued

Notch pathway components

| Gene | Ensembl gene ID | Ensembl transcript ID | Ensembl protein ID |
|------|-----------------|----------------------|---------------------|
| | | ENST00000559312,ENST00000554521,ENST00000560335,ENST00000555738,ENST00000554818,ENST00000555307,ENST00000555987,ENST00000555859,ENST00000554394,ENST00000326018,ENST00000355058,ENST00000359560,ENST00000454166,ENST00000535282,ENST00000544991 | 0000451513,ENSP00000452888,ENSP00000450817,ENSP00000453209,ENSP00000452069,ENSP00000451959,ENSP00000452357,ENSP00000451559,ENSP00000451326,ENSP00000451374, ENSP00000315193, ENSP00000347169,ENSP00000352563,ENSP00000394025,ENSP00000441258,ENSP00000446001 |
| NUMBL | ENSG00000105245 | ENST00000252891, ENST00000540131 | ENSP00000252891, ENSP00000442759 |
| PSENEN | ENSG00000205155 | ENST00000222266 | ENSP00000222266 |
| PSEN1 | ENSG00000080815 | ENST00000324501,ENST00000357710,ENST00000394164,ENST00000394157,ENST00000406768,ENST00000556864,ENST00000557037,ENST00000556533,ENST00000556066,ENST00000553599,ENST00000557356,ENST00000556951,ENST00000557293,ENST00000553719,ENST00000554131,ENST00000555254,ENST00000556011,ENST00000557511,ENST00000560005,ENST00000261970,ENST00000344094,ENST00000555386,ENST00000553855,ENST00000559361 | ENSP00000326366,ENSP00000350342,ENSP00000377719,ENSP00000377712,ENSP00000385948,ENSP00000451588,ENSP00000451347,ENSP00000452128,ENSP00000452267,ENSP00000452477,ENSP00000451498,ENSP00000450551,ENSP00000451880,ENSP00000451674,ENSP00000451915,ENSP00000450652, ENSP00000451662,ENSP00000451429,ENSP00000453466,ENSP00000261970,ENSP00000339523,ENSP00000450845,ENSP00000452242,ENSP00000454156 |
| PSEN2 | ENSG00000143801 | ENST00000366783,ENST00000366782,ENST00000495488,ENST00000460775,ENST00000472139,ENST00000422240,ENST00000524196,ENST00000340188,ENST00000391872,ENST00000496965 | ENSP00000355747,ENSP00000355746,ENSP00000429682,ENSP00000427912,ENSP00000427806,ENSP00000403737,ENSP00000429036,ENSP00000339860,ENSP00000375745,ENSP00000430647 |
| PTCRA | ENSG00000171611 | ENST00000304672,ENST00000418903,ENST00000441198,ENST00000446507 | ENSP00000304447,ENSP00000407061,ENSP00000409550,ENSP00000392288 |
| RBPJ | ENSG00000168214 | ENST00000345843,ENST00000361572,ENST00000342320,ENST00000512351,ENST00000512671,ENST00000505958,ENST00000507561,ENST00000504907,ENST00000506956,ENST00000514807,ENST00000509158,ENST00000514730,ENST00000507574,ENST00000514675,ENST00000515573,ENST00000511546,ENST00000504938,ENST00000504423,ENST00000510778,ENST00000348160,ENST00000342295,ENST00000355476,ENST00000513182,,ENST00000510778,ENST00000348160, | ENSP00000305815,ENSP00000354528,ENSP00000340124,ENSP00000424789,ENSP00000423644,ENSP00000426872,ENSP00000423907,ENSP00000423703,ENSP00000425750,ENSP00000424989,ENSP00000424804,ENSP00000425061,ENSP00000422617,ENSP00000423575,ENSP00000423406,ENSP00000422838, ENSP00000424459,ENSP00000421804,ENSP00000427170,ENSP00000339699,ENSP00000345206,ENSP00000347659,ENSP00 |

TABLE 3-continued

Notch pathway components

| Gene | Ensembl gene ID | Ensembl transcript ID | Ensembl protein ID |
|---|---|---|---|
| | | ENST00000342295,ENST00000355476,ENST00000513182 | 000427344,ENSP00000427170,ENSP00000339699,ENSP00000345206,ENSP00000347659,ENSP00000427344 |
| RFNG | ENSG00000169733 | ENST00000310496, ENST00000429557 | ENSP00000307971, ENSP00000402931 |
| RING1 | ENSG00000204227 | ENST00000374656 | ENSP00000363787 |
| SKP1 | ENSG00000113558 | ENST00000353411,ENST00000522552,ENST00000519321,ENST00000517625,ENST00000522855,ENST00000520417,ENST00000523359,ENST00000328392,ENST00000521216,ENST00000519718,ENST00000523966,ENST00000519054 | ENSP00000231487,ENSP00000429472,ENSP00000429415,ENSP00000429961,ENSP00000429686,ENSP00000429996,ENSP00000428962,ENSP00000331708,ENSP00000431067,ENSP00000430774,ENSP00000429995,ENSP00000430885 |
| SNW1 | ENSG00000100603 | ENST00000261531,ENST00000555761,ENST00000554775,ENST00000554324,ENST00000416259,ENST00000556428 | ENSP00000261531,ENSP00000451129,ENSP00000452059,ENSP00000452473,ENSP00000387847,ENSP00000451741 |
| STAT3 | ENSG00000168610 | ENST00000264657,ENST00000404395,ENST00000389272 | ENSP00000264657,ENSP00000384943,ENSP00000373923 |
| TLE1 | ENSG00000196781 | ENST00000376499,ENST00000418319,ENST00000376484,ENST00000376463,ENST00000355002,ENST00000376472 | ENSP00000365682,ENSP00000391347,ENSP00000365667,ENSP00000365646,ENSP00000347102,ENSP00000365655 |

Bcl-2 Inhibitors

As shown in the Examples, Bcl-2 expression is inhibited in the presence of the bromodomain inhibitor (JQ1). Accordingly, certain aspects of the invention contemplate treatment using Bcl-2 inhibitors alone or in combination with Notch pathway inhibitors to treat certain cancers.

Members of the Bcl-2 family control the integrity of the outer mitochondrial membrane (OMM) and thus are involved in determining the susceptibility of cells to apoptosis induced by the intrinsic pathway. The Bcl-2 family comprises anti-apoptotic members, such as Bcl-2, Mcl-1, Bcl-XL, Bcl-w and Bcl-2A1 (Bfl-1/A1), multidomain proapoptotic members, such as Bax and Bak, and proapoptotic BH3-only proteins, including Bad, Bim, Puma, Bid, Bik, Noxa and Bmf.

A Bcl-2 inhibitor is any molecule or compound that can prevent or inhibit the activity, in part or in whole, of Bcl-2 family members (e.g., Bcl-2, Bcl-X, Bcl-w, Mcl-1 or Bcl-2A1). It is to be understood that the activity of Bcl-2 family members may include one or more activities, such as cell survival or apoptosis. Inhibitors of Bcl-2 family members are known in the art. Examples of Bcl-2 inhibitors include, but are not limited to, HA14-1(Tocris Bioscience), BH3I-1 (Sigma-Aldrich), antimycin A (Sigma-Aldrich), chelerythrine (Fermentek), gossypol (NSC19048, NCI—Developmental Therapeutics Program), apogossypol (NSC736630, NCI—Developmental Therapeutics Program), TW-37 (Selleckchem), 4-(3-methoxy-phenylsulfonyl)-7-nitro-benzofurazan-3-oxide (MNB), TM12-06, obatoclax (GX15-070, Cephalon), ABT-737 (Selleckchem) and a related orally-active derivative, ABT-263 (Navitoclax, Genentech), AT-101 (Ascenta Therapeutics), pyrogallol-based molecules (Tang et al. J Med Chem. 2007, 50(8):1723-6), and ABT-199 (Abbott and Genentech).

In some embodiments, a Bcl-2 inhibitor is any molecule or compound that reduces or prevents expression of Bcl-2 family members. Examples of such inhibitors include siRNA, shRNA, dsRNA, oligomimics, and proteases that target one or more Bcl-2 family members. In some embodiments, the Bcl-2 inhibitor is the antisense oligonucleotide drug Genasense (G3139, Genta).

Examples of Bcl-2 family members are shown in Table 4.

TABLE 4

Examples of Bcl-2 family members

| Gene | Ensembl gene ID | Ensembl transcript ID | Ensembl protein ID |
|---|---|---|---|
| Bcl-2 | ENSG00000171791 | ENST00000444484, ENST00000398117, ENST00000333681 | ENSP00000404214, ENSP00000381185, ENSP00000329623 |
| Bcl-X | ENSG00000171552 | ENST00000456404, ENST00000450273, ENST00000439267, ENST00000434194, ENST00000422920, ENST00000420653, ENST00000420488, ENST00000376062, ENST00000376055, ENST00000307677 | ENSP00000395545, ENSP00000406203, ENSP00000389688, ENSP00000401173, ENSP00000411252, ENSP00000405563, ENSP00000390760, ENSP00000365230, ENSP00000365223, ENSP00000302564 |

TABLE 4-continued

Examples of Bcl-2 family members

| Gene | Ensembl gene ID | Ensembl transcript ID | Ensembl protein ID |
|---|---|---|---|
| Bcl-w | ENSG00000129473 | ENST00000557579, ENST00000557236, ENST00000556599, ENST00000554635, ENST00000553824, ENST00000250405 | ENSP00000452265, ENSP00000451701, ENSP00000451197, ENSP00000451234, ENSP00000451148, ENSP00000250405 |
| Mcl-1 | ENSG00000143384 | ENST00000439749, ENST00000369026, ENST00000307940 | ENSP00000411395, ENSP00000358022, ENSP00000309973 |
| Bcl-2A1 | ENSG00000140379 | ENST00000335661, ENST00000267953 | ENSP00000335250, ENSP00000267953 |

AKT and mTOR Inhibitors

As shown in the Examples, persister cells were found to be sensitive to treatment with an AKT inhibitor or treatment with a mammalian target of rapamycin (mTOR) inhibitor. Accordingly, certain aspects of the invention contemplate treatment using mTOR or AKT inhibitors alone or in combination with Notch pathway inhibitors to treat certain cancers.

An mTOR inhibitor is any molecule or compound that can prevent or inhibit, in part or in whole, the activity of mTOR. It is to be understood that the activity of mTOR may include one or more activities, such as cell growth, cell proliferation, cell motility, cell survival, protein synthesis, or transcription. mTOR gene, mRNA, and protein sequence identifiers are provided in Table 5. Inhibitors of mTOR are known in the art. Examples of mTOR inhibitors include, but are not limited to, rapamycin (sirolimus, Pfizer), temsirolimus (CCI-779, Wyeth), everolimus (Novartis), deforolimus (AP23573, MK-8669, Merck and ARIAD Pharmaceuticals), NVP-BEZ235 (Novartis), BGT226 (Novartis), SF1126 (Semafore Pharmaceuticals), PKI-587 (Selleckchem), PF-04691502 (Selleckchem), INK128 (Intellikine), AZD8055 (Selleckchem), and AZD2014 (AstraZeneca).

In some embodiments, an mTOR inhibitor is any molecule or compound that reduces or prevents expression of mTOR. Examples of such inhibitors include siRNA, shRNA, dsRNA, and oligomimics with complementarity to mTOR mRNA, and proteases that target mTOR protein.

An AKT inhibitor is any molecule or compound that can prevent or inhibit, in part or in whole, the activity of an AKT family member (AKT1, AKT2, or AKT3). It is to be understood that the activity of AKT may include one or more activities, such as glucose metabolism, apoptosis, cell proliferation, transcription and cell migration. AKT family member gene, mRNA, and protein sequence identifiers are provided in Table 5. Inhibitors of AKT are known in the art. Examples of AKT inhibitors include, but are not limited to, MK-2206 (Selleckchem), GDC-0068 (Genetech), Perifosine (Selleckchem), GSK690693 (Selleckchem), AT7867 (Selleckchem), CCT128930 (Selleckchem), PF-04691502 (Selleckchem), INK128 (Selleckchem), RX-0201 (Rexahn Pharmaceuticals), PBI-05204 (Phoenix Biotechnology, Inc.), GSK2141795 (GlaxoSmithKline), Erucylphosphocholine (ErPC, AEterna Zentaris Inc.), and XL-418 (Exelixis).

In some embodiments, an AKT inhibitor is any molecule or compound that reduces or prevents expression of an AKT family member (AKT1, AKT2, or AKT3). Examples of such inhibitors include siRNA, shRNA, dsRNA, oligomimics, and proteases that target AKT.

TABLE 5 mTOR and AKT family members

| Gene | Ensembl gene ID | Ensembl transcript ID | Ensembl protein ID |
|---|---|---|---|
| FRAP1/ mTOR | ENSG00000198793 | ENST00000361445, ENST00000376838, ENST00000455339, ENST00000495435, ENST00000476768, ENST00000490931, ENST00000473471 | ENSP00000354558, ENSP00000366034, ENSP00000398745 |
| AKT1 | ENSG00000142208 | ENST00000349310, ENST00000407796, ENST00000402615, ENST00000554848, ENST00000554581, ENST00000555528, ENST00000544168, ENST00000554192, ENST00000555380, ENST00000555926, ENST00000555458, ENST00000553797, ENST00000557494, ENST00000554585, ENST00000557552, ENST00000553506, ENST00000556836, ENST00000554826 | ENSP00000270202, ENSP00000384293, ENSP00000385326, ENSP00000451166, ENSP00000451828, ENSP00000450688, ENSP00000443897, ENSP00000450681, ENSP00000451290, ENSP00000451824, ENSP00000451470 |
| AKT2 | ENSG00000105221 | ENST00000392038, ENST00000452077, ENST00000456441, ENST00000423127, ENST00000416994, ENST00000416362, ENST00000427375, ENST00000441941, ENST00000392037, ENST00000497948, ENST00000579047, ENST00000311278, ENST00000578123, ENST00000583859, ENST00000580747, ENST00000486368, ENST00000578615, ENST00000578310, ENST00000476247, ENST00000358335, ENST00000596634, ENST00000424901, ENST00000492463, ENST00000489375, ENST00000584288, ENST00000391844, ENST00000491778, ENST00000601166, ENST00000498350, ENST00000391845, ENST00000486647, ENST00000581582, ENST00000480878, ENST00000476266, ENST00000483166, ENST00000487537, ENST00000537834, ENST00000496089, ENST00000580878, ENST00000579345, ENST00000578282, ENST00000578975 | ENSP00000375892, ENSP00000404083, ENSP00000396532, ENSP00000403842, ENSP00000392458, ENSP00000407999, ENSP00000403890, ENSP00000396968, ENSP00000375891, ENSP00000472382, ENSP00000471369, ENSP00000309428, ENSP00000462022, ENSP00000462715, ENSP00000463806, ENSP00000463686, ENSP00000463262, ENSP00000462919, ENSP00000463368, ENSP00000351095, ENSP00000470604, ENSP00000399532, ENSP00000462776, ENSP00000470822, ENSP00000462469, ENSP00000375719, ENSP00000463086, ENSP00000472371 |
| AKT3 | ENSG00000117020 | ENST00000366539, ENST00000336199, ENST00000366540, ENST00000552631, ENST00000263826, ENST00000463991, ENST00000490018, ENST00000491219, | ENSP00000355497, ENSP00000336943, ENSP00000355498, ENSP00000447820, ENSP00000263826 |

TABLE 5-continued mTOR and AKT family members

| Gene | Ensembl gene ID | Ensembl transcript ID | Ensembl protein ID |
|---|---|---|---|
| | | ENST00000492957, ENST00000550388 | |

Treatment Methods

The invention provides methods of treatment of a patient having cancer. In some embodiments, the patient is identified as one who has cancer associated with or characterized by a Notch pathway activation mutation. The methods may comprise administration of one or more BRD inhibitors in the absence of a second therapy.

Other methods of the invention comprise administration of a first inhibitor and a second inhibitor. The designation of "first" and "second" inhibitors is used to distinguish between the two and is not intended to refer to a temporal order of administration of the inhibitors.

The first inhibitor may be a bromodomain inhibitor. The bromodomain inhibitor may target the gene, mRNA expression, protein expression, and/or activity of any member of the bromodomain family, in all instances reducing the level and/or activity of one or more bromodomain-containing proteins (e.g., Brd1, Brd2, Brd3, Brd4, Brd7, or BrdT). Inhibitors may be nucleic acids such as DNA and RNA aptamers, antisense oligonucleotides, siRNA and shRNA, small peptides, antibodies or antibody fragments, and small molecules such as small chemical compounds. The bromodomain inhibitor may be a pan-bromodomain inhibitor or a selective bromodomain inhibitor.

In some embodiments, the first inhibitor may be a BET inhibitor. The BET inhibitor may target the gene, mRNA expression, protein expression, and/or activity of any member of the BET family, in all instances reducing the level and/or activity of one or more BET (e.g., Brd1, Brd2, Brd3, Brd4, Brd7, or BrdT). Inhibitors may be nucleic acids such as DNA and RNA aptamers, antisense oligonucleotides, siRNA and shRNA, small peptides, antibodies or antibody fragments, and small molecules such as small chemical compounds.

The BET inhibitor may be a pan-BET inhibitor or a selective BET inhibitor. BET inhibitors include but are not limited to, RVX-208, PFI-1, OTX015, GSK525762A, JQ1 and Formulas I-XXII and any other compounds as outlined in herein. In some embodiments, the BET inhibitor is JQ1.

The first inhibitor may be a Bcl-2 inhibitor. The Bcl-2 inhibitor may target the gene, mRNA expression, protein expression, and/or activity of any member of the Bcl-2 family, in all instances reducing the level and/or activity of one or more Bcl-2 family member (e.g. Bcl-2, Bcl-X, Bcl-w, Mcl-1 or Bcl-2A1). Inhibitors may be nucleic acids such as DNA and RNA aptamers, antisense oligonucleotides, siRNA and shRNA, small peptides, antibodies or antibody fragments, and small molecules such as small chemical compounds.

The Bcl-2 inhibitor may be a pan-Bcl-2 inhibitor or a selective Bcl-2 inhibitor. In some embodiments, the Bcl-2 inhibitor selectively inhibits one or more of: Bcl-2, Bcl-X, Bcl-w, Mcl-1 or Bcl-2A1. Examples of pan- and selective-Bcl-2 inhibitors include but are not limited to HA14-1, BH3I-1, antimycin A, chelerythrine, gossypol (NSC19048), apogossypol (NSC736630), TW-37, 4-(3-methoxy-phenylsulfonyl)-7-nitro-benzofurazan-3-oxide (MNB), TM12-06, obatoclax (GX15-070), ABT-737, ABT-263, AT-101, pyrogallol-based molecules, ABT-199, and Genasense (G3139).

In some embodiments, the first inhibitor may be an AKT or mTOR inhibitor. In some embodiments, an AKT inhibitor and mTOR inhibitor may be administered together.

The second inhibitor may be an inhibitor of the Notch signaling pathway. It is to be understood that the inhibitor can act on any part of the Notch signaling pathway as described herein. The Notch pathway inhibitor may target a gene, mRNA expression, protein expression, and/or activity in the Notch pathway or associated with the Notch pathway, in all instances reducing the level and/or activity of the Notch signaling pathway. Inhibitors may be nucleic acids such as DNA and RNA aptamers, antisense oligonucleotides, siRNA and shRNA, small peptides, antibodies or antibody fragments, and small molecules such as small chemical compounds.

In some embodiments, the Notch pathway inhibitor is a gamma secretase inhibitor (GSI). In some embodiments the GSI is DBZ, BMS-906024, RO4929097, LY450139, BMS-708163, MK-0752, PF-03084014, IL-X, z-Leu-leu-Nle-CHO, or N—[N-(3,5-difluorophenacetyl)-L-alanyl]-Sphenylglycine t-butyl ester (DAPT). Other Notch pathway inhibitors are provided herein such as in but not limited to LBH589 (Panobinostat), MEDI0639, Choline magnesium trisalicylate (e.g., Trilisate), or Curcumin (a curcuminoid of turmeric).

In some embodiments, the invention contemplates the use of a BRD inhibitor, a Notch pathway inhibitor, and a Bcl-2 inhibitor.

Other aspects of the invention provide methods for treating subjects with cancer with an inhibitor of one or more chromatin regulatory proteins selected from ARID3B, EZH2, PRMT2, SND1, BRD1, SUV39H1, PRMT5, SS18, BRD4, KDM5D, PRMT7, STAG3L1, CD2BP2, MLL5, SUDS3, CHD1, MINA, CHD8, MORF4L1, or CHRAC1. In some embodiments, the one or more chromatin regulatory proteins are selected from BRD4 or PRMT7.

When two or more inhibitors or agents are administered to a subject, these can be administered simultaneously (e.g., where they are pre-mixed and administered together), substantially simultaneously (e.g., where they are administered one after another in the time it would take a medical practitioner to administer two agents to a subject), or sequentially with a period of time lapsing between the inhibitor administrations. The two or more inhibitors can also be administered by the same route or by a different route. For example, the inhibitors may be all administered by injection (e.g., intravenous injection) or orally. As another example, one inhibitor may be administered by injection and another may be administered orally.

The term "treat", "treated," "treating" or "treatment" is used herein to mean to relieve, reduce or alleviate at least one symptom of a disease such as cancer in a subject. For example, treatment can be diminishment of one or several symptoms of a disorder or complete eradication of a disorder, such as cancer. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject. Within the meaning of the present invention, the disease is typically a cancer.

The term "effective amount" is used herein to mean the amount of an agent or inhibitor required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

Where two or more inhibitors are administered to the subject, the effective amount may be a combined effective amount. The effective amount of a first inhibitor may be different when it is used with a second and optionally a third inhibitor. When two more inhibitors are used together, the effective amounts of each may be the same as when they are used alone. Alternatively, the effective amounts of each may be less than the effective amounts when they are used alone because the desired effect is achieved at lower doses. Alternatively, again, the effective amount of each may be greater than the effective amounts when they are used alone because the subject is better able to tolerate one or more of the inhibitors which can then be administered at a higher dose provided such higher dose provides more therapeutic benefit.

Subjects

The term "subject" or "patient" is intended to include humans and animals that are capable of suffering from or afflicted with a cancer or any disorder involving, directly or indirectly, a cancer. Examples of subjects include mammals, e.g., humans, dogs, cows, horses, pigs, sheep, goats, cats, mice, rabbits, rats, and transgenic non-human animals. In some embodiments, subjects include companion animals, e.g. dogs, cats, rabbits, and rats. In some embodiments, subjects include livestock, e.g., cows, pigs, sheep, goats, and rabbits. In some embodiments, subjects include Thoroughbred or show animals, e.g. horses, pigs, cows, and rabbits. In important embodiments, the subject is a human, e.g., a human having, at risk of having, or potentially capable of having cancer.

Cancer

The term "cancer" is used herein to mean malignant solid tumors as well as hematological malignancies. Examples of cancer include but are not limited to leukemias, lymphomas, myelomas, carcinomas, metastatic carcinomas, sarcomas, adenomas, nervous system cancers and genito-urinary cancers. In certain embodiments, the cancer is acute lymphoblastic leukemia. In other embodiments, the foregoing methods are useful in treating adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, osteosarcoma, fibrous histiocytoma, brain cancer, brain stem glioma, cerebellar astrocytoma, malignant glioma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinema, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, and Wilms tumor.

In some embodiments, the cancer is a resistant to a Notch pathway inhibitor. A cancer that is resistant to a Notch pathway inhibitor means that the cancer does not respond to such inhibitor, for example as evidenced by continued proliferation and increasing tumor growth and burden. In some instances, the cancer may have initially responded to treatment with such inhibitor (referred to herein as a previously administered therapy) but may have grown resistant after a time. In some instances, the cancer may have never responded to treatment with such inhibitor at all.

Notch Pathway Activation Mutations

In some embodiments, the cancer is associated with or is characterized by a Notch pathway activation mutation. A cancer that is associated with or is characterized by a Notch pathway activation mutation is a cancer that carries such a mutation, as detected by any number of diagnostic assays and methods including fluorescence in situ hybridization (FISH), genomic sequencing, whole exome sequencing, whole genome sequencing, and the like. For example, a mutation in the Notch1 gene can be detected by Notch1 exon sequencing which can be done using a variety of methods as described above including, for example Sanger sequencing. In some embodiments, tumorigenesis, tumor progression, and/or metastasis is increased or enhanced by a Notch pathway activation mutation. Such tumorigenesis, tumor progression and/or metastasis processes that may be increased or enhanced by a Notch pathway activation mutation include, but is not limited to: the epithelial-to-mesenchymal transition (EMT), angiogenesis, and bone metastasis (Sethi et al. British Journal of Cancer, 105; 1805-1810, 2011). In some embodiments, the cancer is sensitive to a Notch pathway inhibitor.

The term "Notch pathway" as used herein encompasses Notch, Notch ligands, and upstream and downstream effectors of the Notch signaling pathway. The term "activation mutation" as used herein refers to mutations (e.g. a mutation in the coding region of a downstream effector of the Notch pathway or chromosomal translocation, point mutations, and chromosomal amplification at the Notch receptor loci) or epigenetic modifications within Notch, Notch ligands, upstream and/or downstream effectors of the Notch pathway.

Examples of cancers that are associated with a Notch pathway activation mutation, are characterized by a Notch pathway activation mutation, or are sensitive to a Notch pathway inhibitor include, but are not limited to: hematological tumors, T-cell acute lymphoblastic leukemia, B-cell malignancies, breast cancer, gut cancer, skin cancer, keratinocyte-derived carcinoma, melanocyte-derived carcinoma, primary melanoma, basal cell carcinoma, squamous cell carcinoma, cervical cancer, prostate cancer, non-small cell lung adenocarcinoma, ovarian carcinoma, medulloblastoma, Kaposi's sarcoma, pancreatic cancer, colorectal cancer, and glioma (see, e.g., Bolós et. al., Notch Signaling in Development and Cancer, Endocrine Reviews, 28(3):339-363, 2007; Sethi et al., British Journal of Cancer, 105; 1805-1810, 2011). In some embodiments, the cancer that has or is characterized by a Notch pathway activation mutation is acute lymphoblastic leukemia. In certain embodiments, the cancer that has or is characterized by a Notch pathway activation mutation is T-cell acute lymphoblastic leukemia.

Other cancers associated with or are characterized by a Notch pathway activation mutation may be identified by detecting mutations or epigenetic modifications within Notch, Notch ligands, upstream and/or downstream effectors of the Notch pathway using methods well known in the art (e.g., genomic and/or proteomic means to identify regions or factors that affect the expression of any gene within the Notch pathway).

Pharmaceutical Formulations, Administration and Dosages

Provided herein are pharmaceutical formulations comprising single agents, such as bromodomain inhibitors and/or pharmacologically active metabolites, salts, solvates and racemates thereof, or a combination of agents which can be, for example, a combination of two types of agents comprising: (1) a bromodomain inhibitor and/or pharmacologically active metabolites, salts, solvates and racemates thereof and (2) Notch pathway inhibitor and/or pharmacologically active metabolites, salts, solvates and racemates thereof.

In another embodiment, the combination of agents comprises (1) a Bcl-2 inhibitor and/or pharmacologically active metabolites, salts, solvates and racemates thereof and (2) Notch pathway inhibitor and/or pharmacologically active metabolites, salts, solvates and racemates thereof. In still another embodiment, the combination of agents comprises (1) a bromodomain inhibitor and/or pharmacologically active metabolites, salts, solvates and racemates thereof, (2) a Bcl-2 inhibitor and/or pharmacologically active metabolites, salts, solvates and racemates thereof and (3) Notch pathway inhibitor and/or pharmacologically active metabolites, salts, solvates and racemates thereof.

In another embodiment, the combination of agents comprises (1) an MTOR inhibitor and/or pharmacologically active metabolites, salts, solvates and racemates thereof and (2) a Notch pathway inhibitor and/or pharmacologically active metabolites, salts, solvates and racemates thereof.

In another embodiment, the combination of agents comprises (1) an AKT inhibitor and/or pharmacologically active metabolites, salts, solvates and racemates thereof and (2) Notch pathway inhibitor and/or pharmacologically active metabolites, salts, solvates and racemates thereof.

For therapeutic uses, the inhibitors described herein may be administered systemically, for example, formulated in a pharmaceutically-acceptable buffer such as physiological saline. Preferable routes of administration include, for example, subcutaneous, intravenous, intraperitoneally, intramuscular, or intradermal injections that provide continuous, sustained levels of the drug in the subject.

Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the cancer. Generally, amounts will be in the range of those used for other agents used in the treatment of other diseases associated with such diseases or states, although in certain instances lower amounts will be needed because of the increased specificity of the compound. A compound is administered at a dosage that is cytotoxic to a neoplastic cell, that reduces the biological activity of a bromodomain, Notch pathway, or Bcl-2 family member, or that reduces the proliferation, survival, or invasiveness of a neoplastic cell as determined by a method known to one skilled in the art Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 µg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other embodiments, it is envisaged that doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

The formulation of a compound for the treatment of a cancer may be by any suitable means that results in a concentration of the therapeutic that, combined with other components, is effective in ameliorating, reducing, or stabilizing cancer. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a neoplasia or inflammatory disease by using carriers or chemical derivatives to deliver the therapeutic agent to a particular cell type (e.g., neoplastic cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra. Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates cancer, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active anticancer therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices.

Materials for use in the preparation of microspheres and/or microcapsules are, e.g., biodegradable/bioerodible polymers such as polygalactia poly-(isobutyl cyanoacrylate), poly(2-hydroxyethyl-L-glutaminine) and, poly(lactic acid).

Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Solid Dosage Forms for Oral Use

Formulations for oral use include tablets containing the active ingredient(s) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

The solid tablet compositions may include a coating adapted to protect the composition from unwanted chemical changes, (e.g., chemical degradation prior to the release of the active therapeutic substance). The coating may be applied on the solid dosage form in a similar manner as that described in Encyclopedia of Pharmaceutical Technology, supra.

At least two therapeutics may be mixed together in the tablet, or may be partitioned. In one example, the first active anti-neoplasia therapeutic is contained on the inside of the tablet, and the second active therapeutic is on the outside, such that a substantial portion of the second therapeutic is released prior to the release of the first therapeutic.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may, e.g., be constructed to release the active anti-neoplasia or anti-inflammatory therapeutic by controlling the dissolution and/or the diffusion of the active substance. Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more therapeutic compounds may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the compound(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Combination Therapies

Optionally, one or more inhibitors of the invention may be administered in combination with any other standard anti-cancer therapy known in the art; such methods are known to the skilled artisan and described in Remington's Pharmaceutical Sciences by E. W. Martin. If desired, agents of the invention (e.g., bromodomain inhibitors, Notch pathway inhibitors, and Bcl-2 inhibitors) are administered in combination with any conventional cancer therapy, including but not limited to, surgery, radiation therapy, or chemotherapy.

In preferred embodiments, a compound of the invention is administered in combination with an epigenetic or transcriptional modulator (e.g., DNA methyltransferase inhibitor, histone deacetylase inhibitor (HDAC inhibitor), lysine methyltransferase inhibitor), with antimitotic drugs (e.g., taxanes, vinca alkaloids), hormone receptor modulators (e.g., estrogen receptor modulators, androgen receptor modulators), cell signaling pathway inhibitors (e.g., tyrosine kinase inhibitors), modulators of protein stability (proteasome inhibitors), hsp90 inhibitors, conventional chemotherapeutics, glucocorticoids, all-trans retinoic acid or other agents that promote differentiation.

Diagnostic/Prognostic Methods

In one aspect, the invention provides methods of detecting the presence of one or more predictive, diagnostic or prognostic markers in a sample (e.g., a biological sample from a cancer patient). A variety of screening methods known to one of skill in the art may be used to detect the presence and the level of the marker in the sample including DNA, RNA and protein detection. The techniques described herein can be used to determine the presence or absence of a target in a sample obtained from a patient.

Identification of one or more markers (including identification of elevated levels of one or more markers) in a patient assists a physician or other medical professional in determining a treatment protocol for the patient. For example, in a patient having one or more markers, the physician may treat the patient with a combination therapy as described in more detail above.

Detection Methods

The methods invention may be protein or mRNA based. Examples of protein-based assays include immunoassays (also referred to herein as immune-based assays), Western blots, Western immunoblotting, multiplex bead-based assays, and assays involving aptamers (such as SOMAmer™ technology) and related affinity agents. Examples of mRNA-based assays include Northern analysis, quantitative RT-PCR, microarray hybridization, RNA sequencing, and multiplex bead-based assays. These assays are well known in the art and generally and commonly detect and measure the level of the marker of interest. The level of the marker may then be compared to a control level. The control level may be a level of the same marker in a control tissue, control subject, or a population of control subjects. The "control" may be (or may be derived from) a normal subject (or normal subjects). Normal may refer to a subject that is apparently cancer-free. It is to be understood however that the methods provided herein do not require that a control level be measured every time a subject is tested. Rather, it is contemplated that control levels of markers are obtained and recorded and that any test level is compared to such a pre-determined level. Such pre-determined control levels may also be referred to herein as pre-determined threshold levels.

Chromatin Compaction

In some aspects, the invention relates to methods for diagnosing a subject in need of treatment with a bromodomain inhibitor or a combination of agents as described herein, including, but not limited to, a bromodomain inhibitor and/or a Bcl-2 inhibitor. In some embodiments, the method comprises measuring the global level of chromatin compaction. Chromatin compaction can be measured, for example, (a) by partial micrococcal nuclease (MNase) or DNase digestion, (b) by increased expression of heterochromatin associated proteins, such as HP1 alpha, beta and/or gamma, (c) by measuring nucleus size, (d) by decreased expression of DTX1, HES4, and/or CD1d and/or by increased expression of ETS1, ETV6, Runx1, CD52, MYC or Bcl-2, and/or (d) by measuring increased levels of repressive chromatin markers such as H3K27me3, H3K9me2/3 and/or decreased levels of other chromatin markers such as H3K27Ac.

In some embodiments, the method comprises measuring nucleus size, nucleosomal repeat length, or cell size in a sample. The nucleus or cell size may be the nucleus or cell diameter or the nucleus or cell volume. Methods for measuring nucleus size are known in the art and may involve staining nuclei (e.g. with DAPI), fluorescently labeling nuclei (e.g. with green fluorescent protein), or May-Grunwald giemsa staining (particularly for hematopoietic cells). Methods for measuring cell size are known in the art and may involve forward and side scatter analysis using fluorescent activated cell sorting (FACS). Methods for measuring nucleosomal repeat length are known in the art and may involve a micrococcal nuclease (MNase) digestion assay. In some embodiments, a decreased nucleus size or cell size, or an increased nucleosomal repeat length, in a tumor sample compared to a control identifies a subject to be treated with a bromodomain inhibitor or a combination of agents as described herein, including, but not limited to, a bromodomain inhibitor and/or a Bcl-2 inhibitor.

In some embodiments the methods for diagnosing comprise measuring the expression level of HPI-alpha, beta, or gamma. The expression level may be an mRNA level or a protein level. Methods for measuring mRNA and protein levels in a cell population are known in the art. In some embodiments, an increased HPI level in a tumor sample compared to a control identifies a subject to be treated with a bromodomain inhibitor or a combination of agents as described herein, including, but not limited to, a bromodomain inhibitor and/or a Bcl-2 inhibitor.

In some embodiments, the methods for diagnosing comprise measuring expression levels of at least one chromatin state biomarker (CSB). The CSB may be selected from NPM1, NARG1, RCC1, SSRP1, PRMT3, SAP30, CBX6, CHMP2B, UBE2M, WDR77, HMGB1, CARM1, USP13, HDAC4, COQ3, SET, GATAD2A, PRMT6, HMG20B, DNMT1, ADA, SS18, UBE3A, ZMYND11, NOC2LL, UTX, SIN3A, SAP30L, FLJ20309, RCOR2, ARID5A, UBE2Q2, TRIM24, BAZ2B, SMYD3, EZH2, PHF1, PHF2, BCR, SMARCD3, BMI1, CHD6, FBXL11, SIRT7, ASF1A, RCOR3, CBX4, EPC1, BRD1, and BNF11.

In some embodiments, decreased levels in a tumor sample of a CSB from the group consisting of NPM1, NARG1, RCC1, SSRP1, PRMT3, SAP30, CBX6, CHMP2B, UBE2M, WDR77, HMGB1, CARM1, USP13, HDAC4, COQ3, SET, GATAD2A, PRMT6, HMG20B, DNMT1, ADA, SS18, UBE3A, ZMYND11, and/or NOC2LL ("Group I CSB") compared to a control identifies a subject to be treated with a bromodomain inhibitor or a combination of agents as described herein, including, but not limited to, a bromodomain inhibitor and/or a Bcl-2 inhibitor.

In some embodiments, increased levels in a tumor sample of a CSB from the group consisting of UTX, SIN3A, SAP30L, FLJ20309, RCOR2, ARID5A, UBE2Q2, TRIM24, BAZ2B, SMYD3, EZH2, PHF1, PHF2, BCR, SMARCD3, BMI1, CHD6, FBXL11, SIRT7, ASF1A, RCOR3, CBX4, EPC1, BRD1, and/or BNF11 ("Group II CSB") compared to a control identifies a subject to be treated with a bromodomain inhibitor or a combination of agents as described herein, including, but not limited to, a bromodomain inhibitor and/or a Bcl-2 inhibitor.

In some embodiments, more than one CSB expression level is measured. The more than one CSB may be chosen from Group I, Group II, or both Group I and Group II.

Chromatin state biomarkers of the invention include those in Table 6.

TABLE 6

Chromatin state biomarkers

| Gene | Ensembl gene ID | Ensembl transcript ID | Ensembl protein ID |
| --- | --- | --- | --- |
| NPM1 | ENSG00000181163 | ENST00000523622, | ENSP00000428647, |
| | | ENST00000521672, | ENSP00000429485, |
| | | ENST00000517671, | ENSP00000428755, |
| | | ENST00000393820, | ENSP00000377408, |
| | | ENST00000351986, | ENSP00000341168, |
| | | ENST00000296930 | ENSP00000296930 |
| NARG1 | ENSG00000164134 | ENST00000544077, | ENSP00000443524, |
| | | ENST00000515576, | ENSP00000421839, |
| | | ENST00000398947, | ENSP00000381920, |
| | | ENST00000296543 | ENSP00000296543 |
| RCC1 | ENSG00000180198 | ENST00000434290, | ENSP00000405258, |
| | | ENST00000430407, | ENSP00000394650, |
| | | ENST00000429051, | ENSP00000416220, |
| | | ENST00000427469, | ENSP00000402740, |
| | | ENST00000419074, | ENSP00000402260, |
| | | ENST00000411533, | ENSP00000413644, |
| | | ENST00000398958, | ENSP00000381931, |
| | | ENST00000373833, | ENSP00000362939, |
| | | ENST00000373832, | ENSP00000362938, |
| | | ENST00000373831 | ENSP00000362937 |
| SSRP1 | ENSG00000149136 | ENST00000529002, | ENSP00000434546, |
| | | ENST00000526696, | ENSP00000431154, |
| | | ENST00000278412 | ENSP00000278412 |

TABLE 6-continued

Chromatin state biomarkers

| Gene | Ensembl gene ID | Ensembl transcript ID | Ensembl protein ID |
|---|---|---|---|
| PRMT3 | ENSG00000185238 | ENST00000541255, | ENSP00000440367, |
| | | ENST00000526583, | ENSP00000434260, |
| | | ENST00000525188, | ENSP00000435151, |
| | | ENST00000437750, | ENSP00000397766, |
| | | ENST00000331079, | ENSP00000331879, |
| | | ENST00000330796 | ENSP00000329586 |
| SAP30 | ENSG00000164105 | ENST00000296504 | ENSP00000296504 |
| CBX6 | ENSG00000183741 | ENST00000407418, | ENSP00000384490, |
| | | ENST00000216083 | ENSP00000216083 |
| CHMP2B | ENSG00000083937 | ENST00000494980, | ENSP00000418920, |
| | | ENST00000471660, | ENSP00000419998, |
| | | ENST00000263780 | ENSP00000263780 |
| UBE2M | ENSG00000130725 | ENST00000253023 | ENSP00000253023 |
| WDR77 | ENSG00000116455 | ENST00000449340, | ENSP00000409300, |
| | | ENST00000411751, | ENSP00000400321, |
| | | ENST00000235090 | ENSP00000235090 |
| HMGB1 | ENSG00000189403 | ENST00000426225, | ENSP00000411269, |
| | | ENST00000405805, | ENSP00000384678, |
| | | ENST00000399494, | ENSP00000382417, |
| | | ENST00000399489, | ENSP00000382412, |
| | | ENST00000398908, | ENSP00000410465, |
| | | ENST00000341423, | ENSP00000345347, |
| | | ENST00000339872, | ENSP00000343040, |
| | | ENST00000326004 | ENSP00000369904 |
| CARM1 | ENSG00000142453 | ENST00000344150, | ENSP00000340934, |
| | | ENST00000327064 | ENSP00000325690 |
| USP13 | ENSG00000058056 | ENST00000497380, | ENSP00000418651, |
| | | ENST00000497155, | ENSP00000420057, |
| | | ENST00000496897, | ENSP00000417146, |
| | | ENST00000263966 | ENSP00000263966 |
| HDAC4 | ENSG00000068024 | ENST00000544989, | ENSP00000438111, |
| | | ENST00000543185, | ENSP00000440481, |
| | | ENST00000541256, | ENSP00000443057, |
| | | ENST00000456922, | ENSP00000406618, |
| | | ENST00000454542, | ENSP00000405226, |
| | | ENST00000446876, | ENSP00000392912, |
| | | ENST00000445704, | ENSP00000391226, |
| | | ENST00000430200, | ENSP00000410551, |
| | | ENST00000393621, | ENSP00000377243, |
| | | ENST00000345617 | ENSP00000264606 |
| COQ3 | ENSG00000132423 | ENST00000369242, | ENSP00000358245, |
| | | ENST00000369240, | ENSP00000358243, |
| | | ENST00000254759 | ENSP00000254759 |
| SET | ENSG00000119335 | ENST00000454747, | ENSP00000410806, |
| | | ENST00000409104, | ENSP00000387321, |
| | | ENST00000372692, | ENSP00000361777, |
| | | ENST00000372688, | ENSP00000361773, |
| | | ENST00000372686, | ENSP00000361771, |
| | | ENST00000322030 | ENSP00000318012 |
| GATAD2A | ENSG00000167491 | ENST00000537887, | ENSP00000442588, |
| | | ENST00000457895, | ENSP00000404212, |
| | | ENST00000448576, | ENSP00000416452, |
| | | ENST00000444839, | ENSP00000407293, |
| | | ENST00000432704, | ENSP00000390495, |
| | | ENST00000429563, | ENSP00000388416, |
| | | ENST00000429242, | ENSP00000414252, |
| | | ENST00000418032, | ENSP00000411869, |
| | | ENST00000417582, | ENSP00000403703, |
| | | ENST00000404158, | ENSP00000384899, |
| | | ENST00000360315, | ENSP00000353463, |
| | | ENST00000358713, | ENSP00000351552, |
| | | ENST00000252577 | ENSP00000252577 |
| PRMT6 | ENSG00000198890 | ENST00000540389, | ENSP00000440829, |
| | | ENST00000370078, | ENSP00000359095, |
| | | ENST00000361318 | ENSP00000355145 |
| HMG20B | ENSG00000064961 | ENST00000453933, | ENSP00000402877, |
| | | ENST00000435022, | ENSP00000393481, |
| | | ENST00000417382, | ENSP00000393904, |
| | | ENST00000416526, | ENSP00000410924, |
| | | ENST00000402569, | ENSP00000385987, |
| | | ENST00000333651, | ENSP00000328269, |
| | | ENST00000262949 | ENSP00000262949 |
| DNMT1 | ENSG00000130816 | ENST00000541266, | ENSP00000437951, |
| | | ENST00000540357, | ENSP00000440457, |
| | | ENST00000359526, | ENSP00000352516, |
| | | ENST00000340748 | ENSP00000345739 |

TABLE 6-continued

| Chromatin state biomarkers | | | |
|---|---|---|---|
| Gene | Ensembl gene ID | Ensembl transcript ID | Ensembl protein ID |
| ADA | ENSG00000196839 | ENST00000539235, | ENSP00000446464, |
| | | ENST00000537820, | ENSP00000441818, |
| | | ENST00000536532, | ENSP00000440946, |
| | | ENST00000372874 | ENSP00000361965 |
| SS18 | ENSG00000141380 | ENST00000545952, | ENSP00000443097, |
| | | ENST00000542743, | ENSP00000444551, |
| | | ENST00000542420, | ENSP00000438066, |
| | | ENST00000539849, | ENSP00000444647, |
| | | ENST00000539244, | ENSP00000441760, |
| | | ENST00000415083, | ENSP00000414516, |
| | | ENST00000269138, | ENSP00000269138, |
| | | ENST00000269137 | ENSP00000269137 |
| UBE3A | ENSG00000114062 | ENST00000566215, | ENSP00000457771, |
| | | ENST00000438097, | ENSP00000411258, |
| | | ENST00000428984, | ENSP00000401265, |
| | | ENST00000397954, | ENSP00000381045, |
| | | ENST00000356465, | ENSP00000348850, |
| | | ENST00000232165 | ENSP00000232165 |
| NOC2L | ENSG00000188976 | ENST00000327044 | ENSP00000317992 |
| UTX | ENSG00000147050 | ENST00000543216, | ENSP00000443078, |
| | | ENST00000542299, | ENSP00000444873, |
| | | ENST00000536777, | ENSP00000437405, |
| | | ENST00000535688, | ENSP00000444629, |
| | | ENST00000451692, | ENSP00000399980, |
| | | ENST00000433797, | ENSP00000398929, |
| | | ENST00000431196, | ENSP00000408230, |
| | | ENST00000414389, | ENSP00000405910, |
| | | ENST00000382899, | ENSP00000372355, |
| | | ENST00000377967, | ENSP00000367203, |
| | | ENST00000334516 | ENSP00000334340 |
| SIN3A | ENSG00000169375 | ENST00000570115, | ENSP00000455662, |
| | | ENST00000568431, | ENSP00000454750, |
| | | ENST00000568309, | ENSP00000455644, |
| | | ENST00000568190, | ENSP00000456997, |
| | | ENST00000567289, | ENSP00000455834, |
| | | ENST00000565264, | ENSP00000454296, |
| | | ENST00000564778, | ENSP00000455204, |
| | | ENST00000562776, | ENSP00000455072, |
| | | ENST00000394949, | ENSP00000378403, |
| | | ENST00000394947, | ENSP00000378402, |
| | | ENST00000360439 | ENSP00000353622 |
| SAP3OL | ENSG00000164576 | ENST00000440364, | ENSP00000390927, |
| | | ENST00000426761, | ENSP00000416393, |
| | | ENST00000297109 | ENSP00000297109 |
| FU20309 | ENSG00000114933 | ENST00000424117, | ENSP00000402369, |
| | | ENST00000414320, | ENSP00000409031, |
| | | ENST00000403263, | ENSP00000384198, |
| | | ENST00000233270 | ENSP00000233270 |
| RCOR2 | ENSG00000167771 | ENST00000301459 | ENSP00000301459 |
| ARID5A | ENSG00000196843 | ENST00000454558, | ENSP00000400785, |
| | | ENST00000412735, | ENSP00000397286, |
| | | ENST00000359765, | ENSP00000352808, |
| | | ENST00000357485 | ENSP00000350078 |
| UBE2Q2 | ENSG00000140367 | ENST00000569423, | ENSP00000456324, |
| | | ENST00000567921, | ENSP00000454742, |
| | | ENST00000561851, | ENSP00000456229, |
| | | ENST00000561723, | ENSP00000458006, |
| | | ENST00000426727, | ENSP00000400960, |
| | | ENST00000338677, | ENSP00000340187, |
| | | ENST00000267938 | ENSP00000267938 |
| TRIM24 | ENSG00000122779 | ENST00000536822, | ENSP00000440535, |
| | | ENST00000452999, | ENSP00000402079, |
| | | ENST00000439939, | ENSP00000403347, |
| | | ENST00000415680, | ENSP00000390829, |
| | | ENST00000378381, | ENSP00000367632, |
| | | ENST00000343526 | ENSP00000340507 |
| BAZ2B | ENSG00000123636 | ENST00000546335, | ENSP00000437619, |
| | | ENST00000541068, | ENSP00000441341, |
| | | ENST00000441143, | ENSP00000393565, |
| | | ENST00000437839, | ENSP00000415613, |
| | | ENST00000426648, | ENSP00000400505, |
| | | ENST00000392783, | ENSP00000376534, |
| | | ENST00000392782, | ENSP00000376533, |
| | | ENST00000355831, | ENSP00000348087, |
| | | ENST00000343439, | ENSP00000339670, |
| | | ENST00000294905 | ENSP00000294905 |

TABLE 6-continued

Chromatin state biomarkers

| Gene | Ensembl gene ID | Ensembl transcript ID | Ensembl protein ID |
|---|---|---|---|
| SMYD3 | ENSG00000185420 | ENST00000544586, | ENSP00000443400, |
| | | ENST00000541742, | ENSP00000444184, |
| | | ENST00000490107, | ENSP00000419184, |
| | | ENST00000455277, | ENSP00000394281, |
| | | ENST00000453676, | ENSP00000408122, |
| | | ENST00000403792, | ENSP00000385380, |
| | | ENST00000391836, | ENSP00000375712, |
| | | ENST00000388985 | ENSP00000373637 |
| EZH2 | ENSG00000106462 | ENST00000541220, | ENSP00000443219, |
| | | ENST00000536783, | ENSP00000439305, |
| | | ENST00000492143, | ENSP00000417377, |
| | | ENST00000483967, | ENSP00000419856, |
| | | ENST00000483012, | ENSP00000417704, |
| | | ENST00000478654, | ENSP00000417062, |
| | | ENST00000476773, | ENSP00000419050, |
| | | ENST00000460911, | ENSP00000419711, |
| | | ENST00000350995, | ENSP00000223193, |
| | | ENST00000320356 | ENSP00000320147 |
| PHF1 | ENSG00000239756, | ENST00000495185, | ENSP00000433516, |
| | ENSG00000225553, | ENST00000475137, | ENSP00000434774, |
| | ENSG00000112511 | ENST00000454914, | ENSP00000407295, |
| | | ENST00000447305, | ENSP00000396023, |
| | | ENST00000427869, | ENSP00000391901, |
| | | ENST00000423868, | ENSP00000399226, |
| | | ENST00000421466, | ENSP00000395839, |
| | | ENST00000419154, | ENSP00000413510, |
| | | ENST00000495509, | ENSP00000434347, |
| | | ENST00000487667, | ENSP00000432419, |
| | | ENST00000428274, | ENSP00000392697, |
| | | ENST00000427826, | ENSP00000404788, |
| | | ENST00000427004, | ENSP00000410494, |
| | | ENST00000374516, | ENSP00000363640, |
| | | ENST00000374512 | ENSP00000363636 |
| PHF2 | ENSG00000197724 | ENST00000375376, | ENSP00000364525, |
| | | ENST00000359246 | ENSP00000352185 |
| BCR | ENSG00000186716 | ENST00000427791, | ENSP00000396531, |
| | | ENST00000420248, | ENSP00000445910, |
| | | ENST00000398512, | ENSP00000381524, |
| | | ENST00000359540, | ENSP00000352535, |
| | | ENST00000334149, | ENSP00000335450, |
| | | ENST00000305877, | ENSP00000303507, |
| | | ENST00000292697, | ENSP00000292697, |
| | | ENST00000290956 | ENSP00000290956 |
| SMARCD3 | ENSG00000082014 | ENST00000491651, | ENSP00000419886, |
| | | ENST00000485592, | ENSP00000417145, |
| | | ENST00000469154, | ENSP00000417908, |
| | | ENST00000392811, | ENSP00000376558, |
| | | ENST00000356800, | ENSP00000349254, |
| | | ENST00000347683, | ENSP00000173385, |
| | | ENST00000262188 | ENSP00000262188 |
| BMI1 | ENSG00000168283 | ENST00000456675, | ENSP00000401773, |
| | | ENST00000443519, | ENSP00000390768, |
| | | ENST00000442508, | ENSP00000397912, |
| | | ENST00000417470, | ENSP00000398759, |
| | | ENST00000416820, | ENSP00000399220, |
| | | ENST00000376691, | ENSP00000365881, |
| | | ENST00000376663 | ENSP00000365851 |
| CHD6 | ENSG00000124177 | ENST00000440697, | ENSP00000404637, |
| | | ENST00000440647, | ENSP00000392503, |
| | | ENST00000373233, | ENSP00000362330, |
| | | ENST00000373222, | ENSP00000362319, |
| | | ENST00000309279 | ENSP00000308684 |
| FBXL11 | ENSG00000173120 | ENST00000530342, | ENSP00000435776, |
| | | ENST00000529006, | ENSP00000432786, |
| | | ENST00000446134, | ENSP00000392902, |
| | | ENST00000398645, | ENSP00000381640, |
| | | ENST00000308783 | ENSP00000309302 |
| SIRT7 | ENSG00000187531 | ENST00000576971, | ENSP00000458897, |
| | | ENST00000576004, | ENSP00000458737, |
| | | ENST00000575360, | ENSP00000459524, |
| | | ENST00000572902, | ENSP00000461044, |
| | | ENST00000328666 | ENSP00000329466 |
| ASF1A | ENSG00000111875 | ENST00000229595 | ENSP00000229595 |
| RCOR3 | ENSG00000117625 | ENST00000534478, | ENSP00000436057, |
| | | ENST00000534460, | ENSP00000433441, |
| | | ENST00000533469, | ENSP00000436838, |

TABLE 6-continued

Chromatin state biomarkers

| Gene | Ensembl gene ID | Ensembl transcript ID | Ensembl protein ID |
|---|---|---|---|
| | | ENST00000529763, | ENSP00000437048, |
| | | ENST00000529572, | ENSP00000434605, |
| | | ENST00000528926, | ENSP00000432779, |
| | | ENST00000485186, | ENSP00000434181, |
| | | ENST00000452621, | ENSP00000398558, |
| | | ENST00000419091, | ENSP00000413929, |
| | | ENST00000367006, | ENSP00000355973, |
| | | ENST00000367005 | ENSP00000355972 |
| CBX4 | ENSG00000141582 | ENST00000495122, | ENSP00000461198, |
| | | ENST00000448310, | ENSP00000415348, |
| | | ENST00000343048, | ENSP00000345967, |
| | | ENST00000269397 | ENSP00000269397 |
| EPC1 | ENSG00000120616 | ENST00000375110, | ENSP00000364251, |
| | | ENST00000319778, | ENSP00000318559, |
| | | ENST00000263062 | ENSP00000263062 |
| BRD1 | ENSG00000100425 | ENST00000542442, | ENSP00000437514, |
| | | ENST00000457780, | ENSP00000410042, |
| | | ENST00000438393, | ENSP00000388027, |
| | | ENST00000419212, | ENSP00000399110, |
| | | ENST00000404760, | ENSP00000385858, |
| | | ENST00000404034, | ENSP00000384076, |
| | | ENST00000342989, | ENSP00000345886, |
| | | ENST00000216267 | ENSP00000216267 |
| BNF11 | ENSG00000054938 | ENST00000534276, | ENSP00000432055, |
| | | ENST00000529912, | ENSP00000432345, |
| | | ENST00000528789, | ENSP00000431380, |
| | | ENST00000528471, | ENSP00000434589, |
| | | ENST00000525413, | ENSP00000434257, |
| | | ENST00000393519, | ENSP00000377154, |
| | | ENST00000376332, | ENSP00000365510, |
| | | ENST00000376324, | ENSP00000365502, |
| | | ENST00000376323, | ENSP00000365501, |
| | | ENST00000263671 | ENSP00000263671 |
| HP1A (CBX5) | ENSG00000094916 | ENST00000550489, | ENSP00000448452, |
| | | ENST00000209875, | ENSP00000209875, |
| | | ENST00000550411, | ENSP00000449207, |
| | | ENST00000439541, | ENSP00000401009, |
| | | ENST00000552562 | ENSP00000450190 |
| HP1B (CBX1) | ENSG00000108468 | ENST00000225603, | ENSP00000225603, |
| | | ENST00000393408, | ENSP00000377060, |
| | | ENST00000444685, | ENSP00000393179, |
| | | ENST00000402583 | ENSP00000385413 |
| HP1G (CBX3) | ENSG00000122565 | ENST00000337620, | ENSP00000336687, |
| | | ENST00000396386, | ENSP00000379670, |
| | | ENST00000409747, | ENSP00000387348, |
| | | ENST00000456948 | ENSP00000408672 |

In some embodiments, the methods for diagnosing comprise measuring expression levels of at least one biomarker selected from DTX1, HES4, CD1d, ETS1, ETV6, Runx1, Bcl-2, MYC and CD52. In some embodiments, decreased levels in a tumor sample of DTX1, HES4, and/or CD1d compared to a control identifies a subject to be treated with a bromodomain inhibitor or a combination of agents as described herein, including, but not limited to, a bromodomain inhibitor and/or a Bcl-2 inhibitor. In some embodiments, increased levels in a tumor sample of a biomarker selected from the group consisting of ETS1, ETV6, Runx1, CD52, MYC or Bcl-2 compared to a control identifies a subject to be treated with a bromodomain inhibitor or a combination of agents as described herein, including, but not limited to, a bromodomain inhibitor and/or a Bcl-2 inhibitor. Expression levels of biomarkers could be, for example, mRNA and/or protein levels.

In some embodiments, more than one biomarker selected from DTX1, HES4, CD1d, ETS1, ETV6, Runx1, Bcl-2, MYC and CD52 is measured and the diagnosis or identification of a subject is made based on 2 or more biomarkers. These biomarkers are found in Table 7.

TABLE 7

DTX1, HES4, CD1d, ETS1, ETV6, Runx1, Bcl-2, MYC and CD52 Biomarkers

| Gene | Ensembl gene ID | Ensembl transcript ID | Ensembl protein ID |
|---|---|---|---|
| DTX1 | ENSG00000135144 | ENST00000257600, | ENSP00000257600 |
| | | ENST00000547974, | |
| | | ENST00000553140, | |
| | | ENST00000547730, | |
| | | ENST00000548759 | |

TABLE 7-continued

DTX1, HES4, CD1d, ETS1, ETV6, Runx1, Bcl-2, MYC and CD52 Biomarkers

| Gene | Ensembl gene ID | Ensembl transcript ID | Ensembl protein ID |
|---|---|---|---|
| HES4 | ENSG00000188290 | ENST00000304952, ENST00000428771, ENST00000484667, ENST00000481869 | ENSP00000304595, ENSP00000393198, ENSP00000425085 |
| CD1d | ENSG00000158473 | ENST00000368171 | ENSP00000357153 |
| ETS1 | ENSG00000134954 | ENST00000392668, ENST00000319397, ENST00000531611, ENST00000526145, ENST00000345075, ENST00000535549, ENST00000525404, ENST00000527676, ENST00000530924 | ENSP00000376436, ENSP00000324578, ENSP00000435666, ENSP00000433500, ENSP00000340485, ENSP00000441430 |
| ETV6 | ENSG00000139083 | ENST00000396373, ENST00000545027, ENST00000266427, ENST00000544715, ENST00000541426 | ENSP00000379658, ENSP00000441463, ENSP00000266427 |
| Runx1 | ENSG00000159216 | ENST00000344691, ENST00000300305, ENST00000416754, ENST00000358356, ENST00000399240, ENST00000455571, ENST00000399237, ENST00000325074, ENST00000437180, ENST00000486278, ENST00000482318, ENST00000479325, ENST00000467577, ENST00000475045, ENST00000468726, ENST00000494829, ENST00000467692, ENST00000460207, ENST00000469087 | ENSP00000340690, ENSP00000300305, ENSP00000405158, ENSP00000351123, ENSP00000382184, ENSP00000388189, ENSP00000382182, ENSP00000319459, ENSP00000409227, ENSP00000438019 |
| Bcl-2 | ENSG00000171791 | ENST00000398117, ENST00000333681, ENST00000589955, ENST00000444484, ENST00000590515 | ENSP00000381185, ENSP00000329623, ENSP00000466417, ENSP00000404214 |
| MYC | ENSG00000136997 | ENST00000377970, ENST00000259523, ENST00000517291, ENST00000524013, ENST00000520751 | ENSP00000367207, ENSP00000259523, ENSP00000429441, ENSP00000430235, ENSP00000430226 |
| CD52 | ENSG00000169442 | ENST00000374213, ENST00000470468, ENST00000492808 | ENSP00000363330 |

In some embodiments, the methods for diagnosing comprise measuring a level of histone modification. Histone modifications can be detected, e.g., using chromatin immunoprecipitation sequencing (ChIP-Seq). In some embodiments, the histone modification is selected from H3K27me3, H3K9me3, and H3K27Ac. In some embodiments, decreased levels in a tumor sample of H3K27Ac histone modification compared to a control identifies a subject to be treated with a bromodomain inhibitor or a combination of agents as described herein, including, but not limited to, a bromodomain inhibitor and/or a Bcl-2 inhibitor. In some embodiments, increased levels in a tumor sample of a histone modification from the group consisting of H3K27me3 and H3K9me3 compared to a control identifies a subject to be treated with a bromodomain inhibitor and or a combination of agents as described herein, including, but not limited to, a bromodomain inhibitor or a combination of agents as described herein, including, but not limited to, a bromodomain inhibitor and/or a Bcl-2 inhibitor.

In some embodiments, the histone modification is H3K4me1. In some embodiments, elevated levels of H3K4me1 histone modification at a site of elevated H3K27Ac histone modification in the tumor sample compared to the control identifies a subject to be treated with a bromodomain inhibitor or a combination of agents as described herein, including, but not limited to, a bromodomain inhibitor and/or a Bcl-2 inhibitor.

EXAMPLES

Example 1

Modeling and Characterization of Drug Resistance in T-ALL

Methods:

Notch inhibitor sensitive T-ALL cell lines were cultured in the presence of 1 µM GSI in vitro. Cells were plated at 0.25×10⁶/ml in 20 mL and split every 3-4 days. Cell viability, cell size and cell cycle were measured every 3-4 days. GSI treated cells demonstrated decreased proliferation as measured by decreased fold expansion after 7 to 14 days. GSI-treated cells stopped proliferating between day 14 to 30 of culture, but eventually started proliferating again despite the presence of GSI with subsequent growth rates being equal or similar to untreated cells.

For RNA expression profiles, cells were washed once in PBS and then snap frozen. RNA was isolated using the Qiagen RNeasy kit. Expression profiles were obtained with the Affymetrix HU133+2 array.

To measure metabolites, cell culture supernatant was taken on day 1, 2, 3, 4, 5 of culture and frozen. Metabolites were measured by mass spectrometry and results were adjusted to input metabolites in media and fold expansion over time.

Cell size was determined by measuring the forward/side scatter on a FACS Calibur (BD Biosciences). To determine nuclear size, cells were spun on slides using a Cytospin centrifuge, then fixed and permeabilized prior to staining with DAPI or anti-Actin antibody. Staining intensity was measured by fluorescent microscopy.

HP1 protein expression was measured by performing Western Blot analysis using the iblot® system (Invitrogen) and enhanced chemiluminescence (ECL) for visualization.

To measure chromatin compaction, naïve or resistant cells were washed once in PBS, lysed and nuclei were isolated using a sucrose gradient. Samples were adjusted for equal nuclear size prior to digestion with MNase. Digests were done for increasing time intervals. DNA was isolated by phenol/chloroform extraction and nucleosomes run on a gel and visualized by SYBR® Safe DNA gel stain (Invitrogen).

Global histone levels were measured by enzyme-linked immunosorbent assay (ELISA) after acid extraction of histones.

For ChIP-Seq, cells were crosslinked in 1% formaldehyde for 15 minutes. Cells were lysed and sonicated with a Branson 250 to a size range of 200 to 700 bp. Chromatin was immunoprecipitated with antibody against K4me1, H3K27ac or BRD4.

Libraries were prepared from ~5 nanograms of ChIP DNA, loaded onto flow cells and sequenced on the Illumina HiSeq Genome Analyzer by standard procedures. Reads were aligned to the reference (hg19) human genome. For data analysis, enrichment profiles were generated for each histone modification. Briefly, aligned reads were extended to 300 bases to approximate the average ChIP fragment. Signal was then estimated at any given position (25 bp resolution) as the number of sequenced ChIP fragments that overlap that position. A sliding window approach was used to identify significantly enriched intervals or 'peaks' from each dataset.

Results:

A gamma secretase inhibitor (GSI)-resistant leukemia cell population was produced using the methods above. Several biological parameters were compared between the GSI-resistant leukemia cells and naïve leukemia cells (those not treated with a GSI).

Firstly, RNA expression profiles of naïve cells and resistant cells were compared using the methods described above. Gene set enrichment analysis (GSEA) was performed and revealed a shift from Myc-dependent signaling to JNK/Map kinase dependent signaling (FIG. 1).

Figure 2:
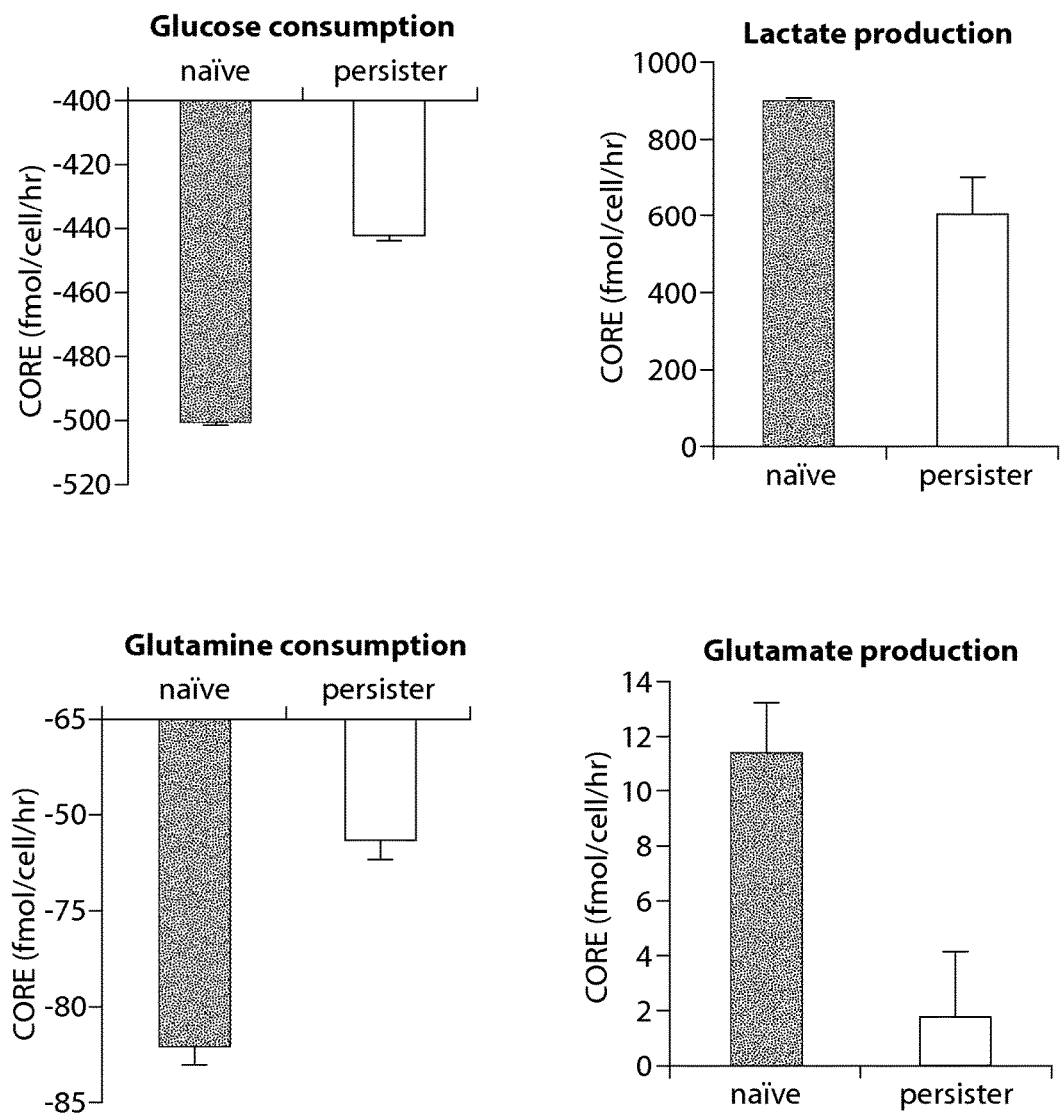
FIG. 2 is a bar graph depicting the ratio of lactate production to glucose consumption and the ratio of glutamate production to glutamine consumption in resistant leukemia cells versus naïve leukemia cells.

Secondly, the metabolic state of resistant versus naïve cells was compared as described above. The ratio of lactate production to glucose consumption was found to be higher in naïve cells than in resistant cells whereas the ratio of glutamate production to glutamine consumption was found to be lower in naïve cells than in resistant cells (FIG. 2).

Figure 3A:
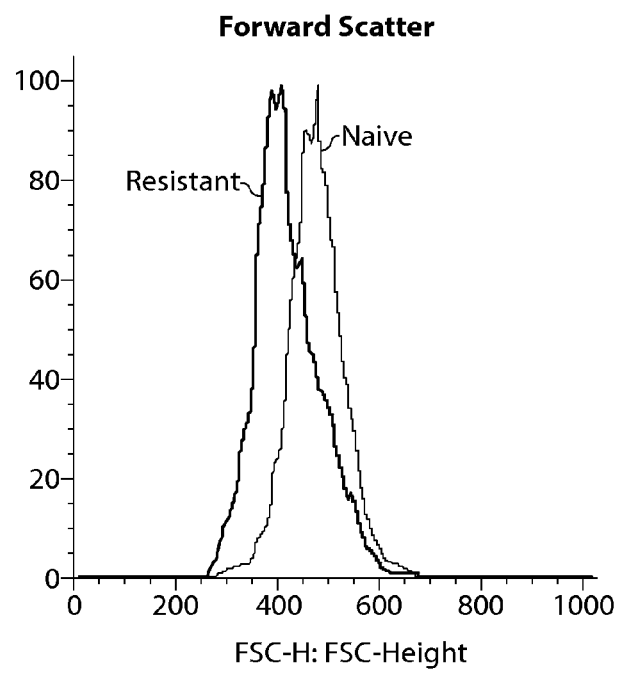
FIG. 3A is a line graph depicting the forward scatter of naïve leukemia cells and resistant leukemia cells.
Figure 3B:
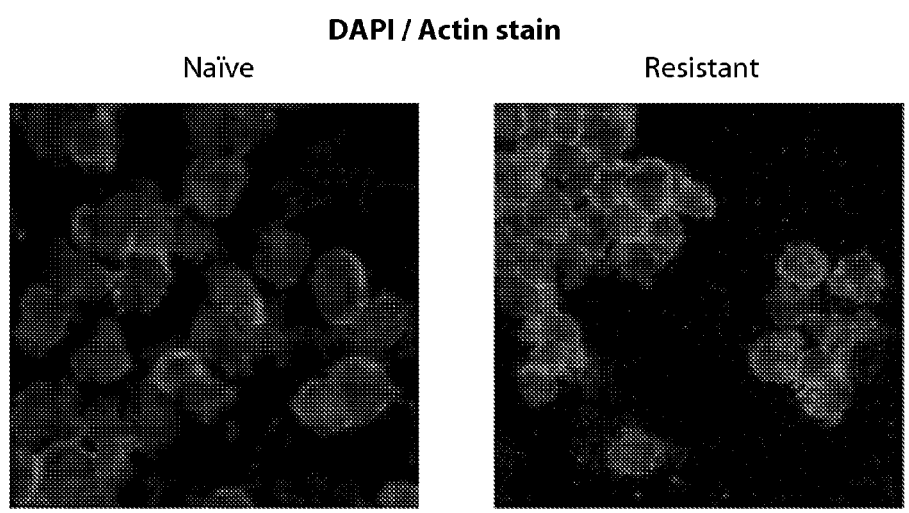
FIG. 3B is a photograph of a nuclear stain (DAPI) and a cytoplasmic stain (Actin) in naïve leukemia cells and resistant leukemia cells.

Thirdly, the nuclear and cellular morphology of resistant versus naïve cells was compared as described above. Forward-scatter FACS analysis revealed that resistant cells were smaller than naïve cells (FIG. 3A). DAPI staining showed that resistant cells contained smaller nuclei than naïve cells (FIG. 3B).

Figure 4A:
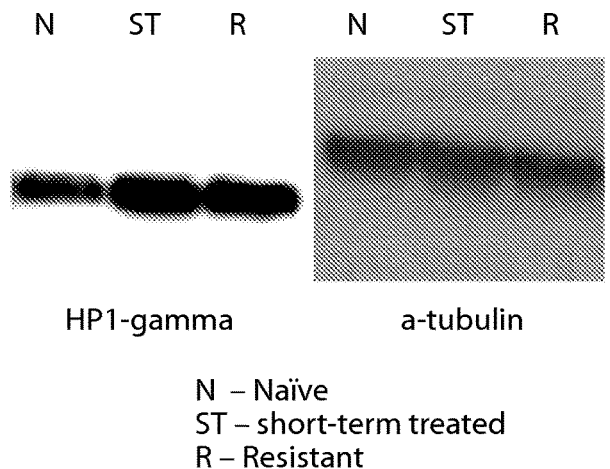
FIG. 4A is a Western blot showing the levels of HP1-gamma in naïve, short-term GSI treated, and resistant leukemia cells.
Figure 4B:
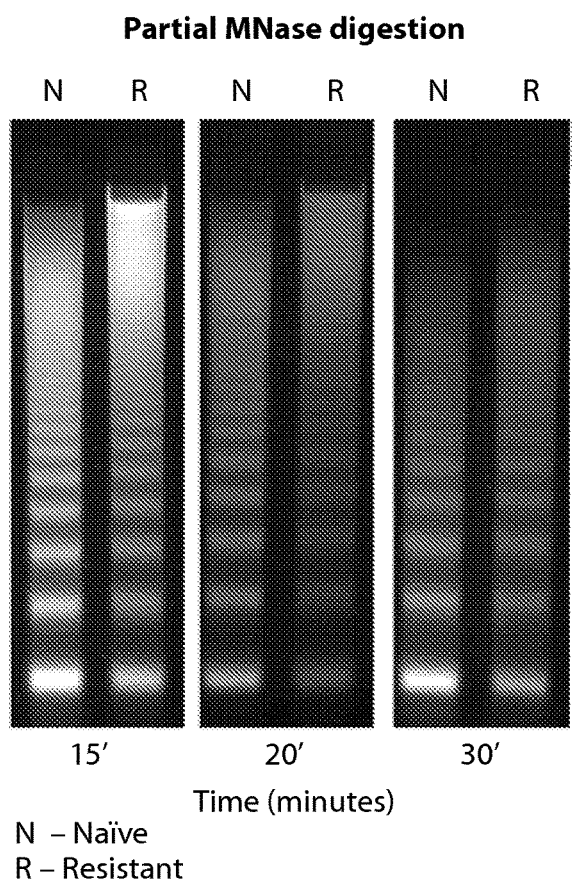
FIG. 4B is a DNA gel showing partial MNase digestion in naïve and resistant leukemia cells.

The smaller nuclear size of resistant cells prompted an investigation of the chromatin status in naïve versus resistant cells. HP1-gamma, a marker of global chromatin compaction was measured using Western blot analysis as described above. A higher level of HP1-gamma was found in resistant cells and those treated for a short period of time with a GSI indicating a higher level of chromatin compaction compared to naïve cells (FIG. 4A). Additionally, a partial MNase digestion was performed as described above and showed that resistant cells are protected from MNase digestion, indicating a higher level of chromatin compaction compared to naïve cells (FIG. 4B).

Figure 5A:
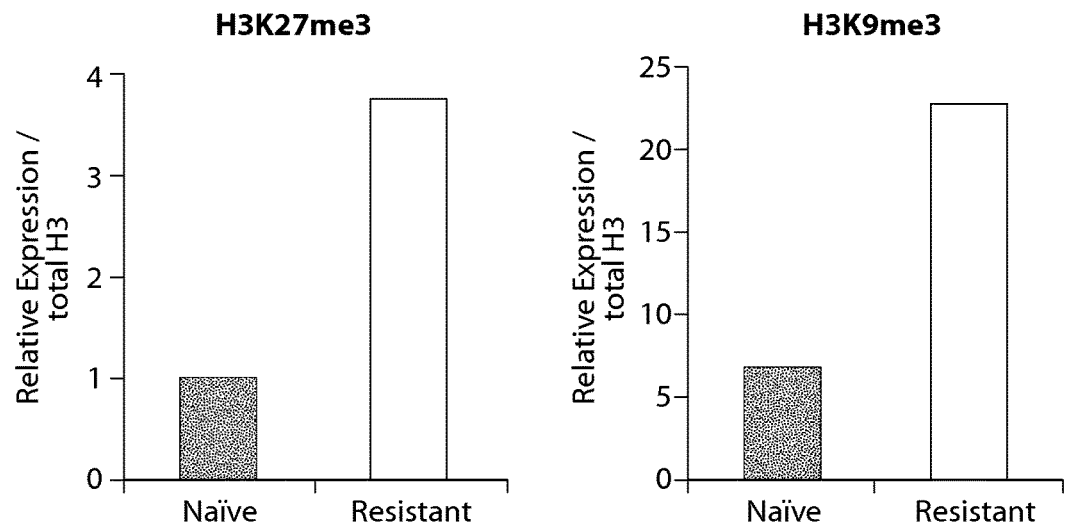
FIG. 5A is a bar graph depicting the levels of chromatin marks H3K27me3 and H3K9me3 in naïve and resistant cells.
Figure 5A:
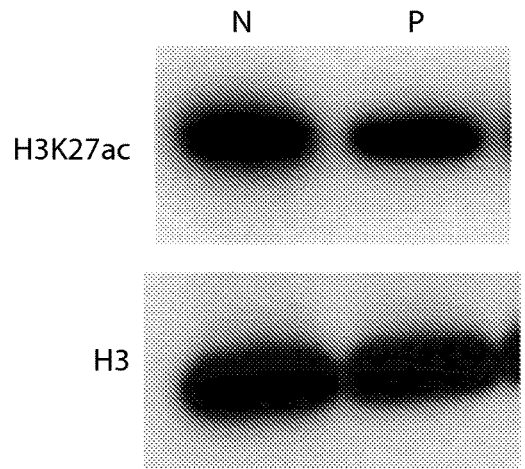

To further analyze the chromatin state in naïve versus resistant cells, the methylation status of certain histone residues that are indicative of the level of chromatin compaction were examined. Tri-methylation of lysine 9 and lysine 27 of histone 3 (H3K9me3 and H3K27me3, respectively) are markers of compacted heterochromatin (a repressed chromatin state). As depicted in FIG. 5A, when assessing global levels of these repressive chromatin marks, both H3K9me3 and H3K27me3 levels were found to be elevated in resistant cells as compared to naïve cells, indicating that resistant had more compacted heterochromatin than naïve cells.

Figure 5B:
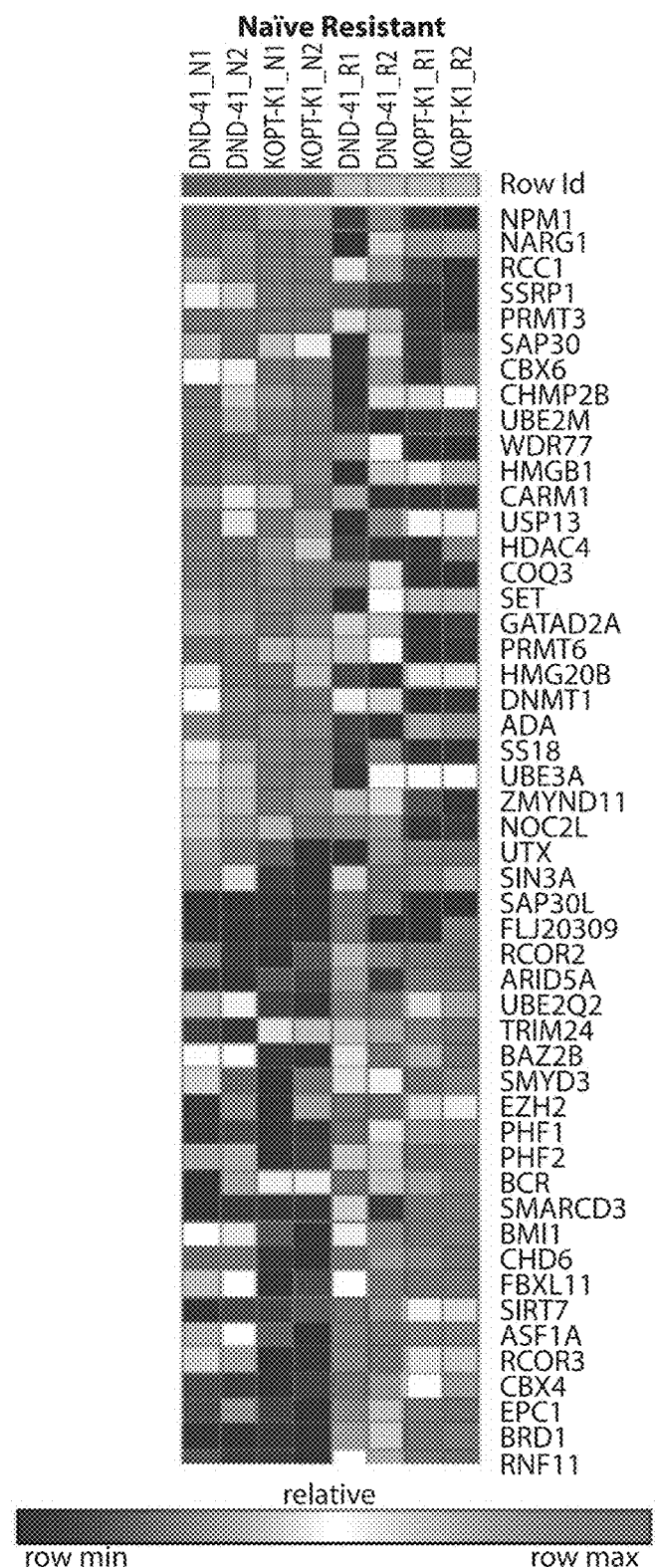
FIG. 5B is a heat map of expression levels of chromatin state biomarkers in naïve and resistant leukemia cells.

Differences in the chromatin regulatory network between naïve and resistant cells were assessed by determining relative expression levels of chromatin state biomarkers. As depicted in FIG. 5B, expression levels of certain chromatin state biomarkers were increased in resistant cells as compared to naïve cells. The chromatin state biomarkers with increased expression levels were UTX, SIN3A, SAP30L, FLJ20309, RCOR2, ARID5A, UBE2Q2, TRIM24, BAZ2B, SMYD3, EZH2, PHF1, PHF2, BCR, SMARCD3, BMI1, CHD6, FBXL11, SIRT7, ASF1A, RCOR3, CBX4, EPC1, BRD1, and BNF11. Such chromatin state biomarkers may be associated with a repressed heterochromatin state.

Conversely, relative expression levels of certain chromatin state biomarkers were decreased in resistant cells as compared to naïve cells. These chromatin state biomarkers included NPM1, NARG1, RCC1, SSRP1, PRMT3, SAP30, CBX6, CHMP2B, UBE2M, WDR77, HMGB1, CARM1, USP13, HDAC4, COQ3, SET, GATAD2A, PRMT6, HMG20B, DNMT1, ADA, SS18, UBE3A, ZMYND11, and NOC2LL. Such chromatin state biomarkers may be associated with promoting an active, open chromatin state.

Example 2

A BRD Inhibitor Blocks Proliferation of and Kills Resistant Leukemia Cells In Vitro and In Vivo Methods:

Notch inhibitor sensitive and resistant T-ALL cell lines were plated in 96 well plates and treated with vehicle, 1 uM GSI and/or increasing concentrations of the bet inhibitor JQ1. Cell viability was determined by measuring luminescence after Celltiterglo® (Promega) addition on day 6. Apoptosis was measured using Caspaseglo® (Promega) on day 4.

Luciferized KOPTK1 cells were injected into NOD/SCID mice by tail vein injection. Tumor burden was measured by following the bioluminescence signal in the mouse body. Following KOPTK1 cell engraftment, mice were treated with a GSI called dibenzazepine (DBZ), JQ1, DBZ+JQ1, or a vehicle control.

Balb/c mice were treated with DBZ+JQ1, DBZ, or vehicle alone. Hyperproliferation of globlet cells was measured by Periodic acid-Schiff (PAS) stain.

Figure 6:
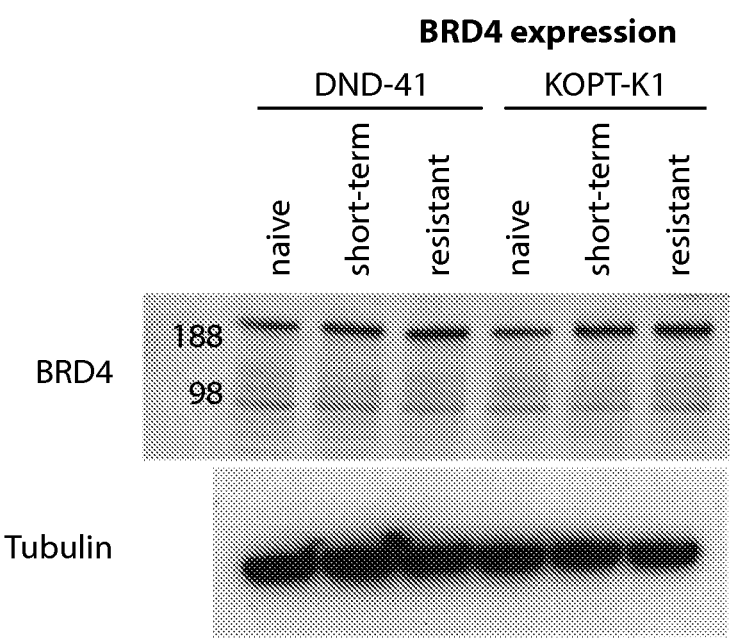
FIG. 6 is a Western blot depicting the protein levels of BRD4 in naïve, short-term GSI treated, and resistant leukemia cells.
Figure 7:
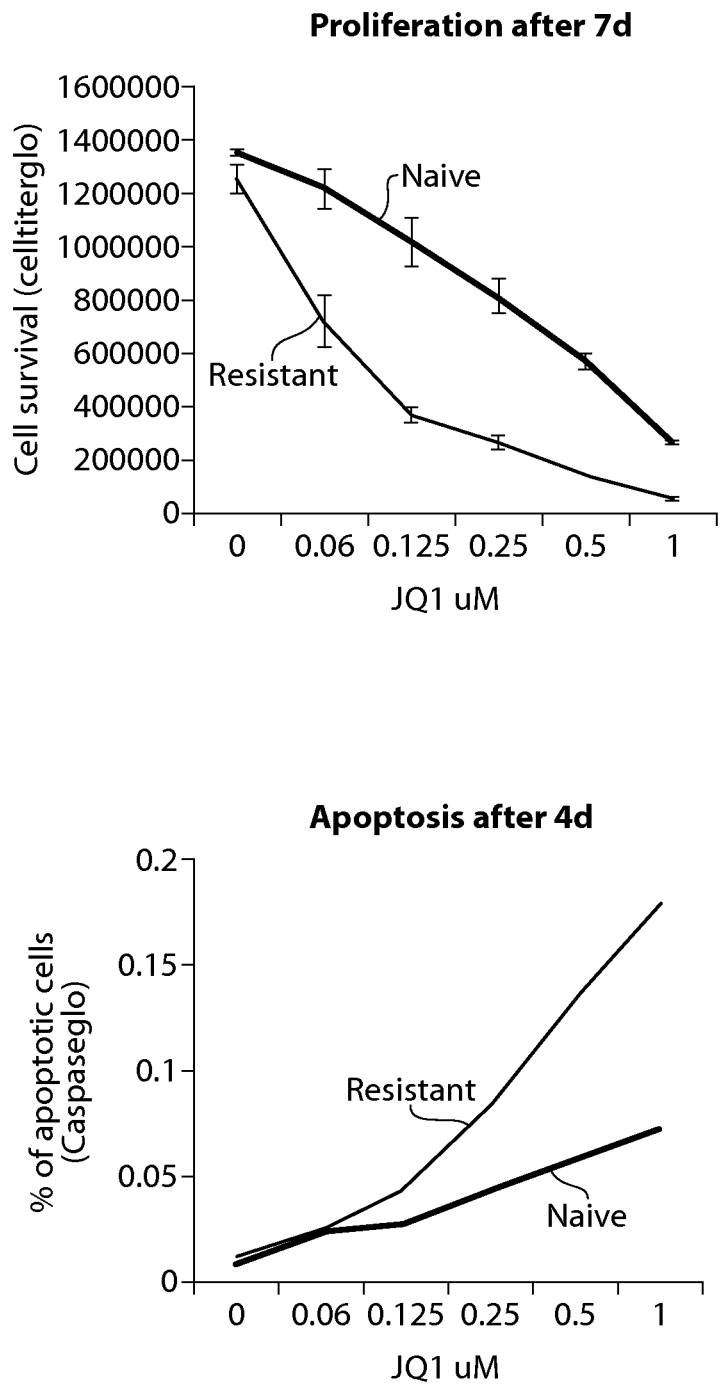
FIG. 7 is two line graphs depicting proliferation of naïve and resistant leukemia cells after 7 days in specific concentrations of JQ1 (left) and apoptosis of naïve and resistant leukemia cells after 4 days in specific concentrations of JQ1 (right).

Results:

One gene from Example 3, BRD4, was chosen as an example chromatin regulatory factor for further analysis in vitro and in vivo. BRD4 was found to be upregulated in leukemia cells that were resistant to a GSI and leukemia cells that underwent short-term treatment with a GSI compared to naïve leukemia cells (FIG. 6). Treatment with a bromodomain inhibitor, JQ1, resulted in a decrease in proliferation and an increase in apoptosis in resistant leukemia cells compared to naïve leukemia cells (FIG. 7).

Figure 8:
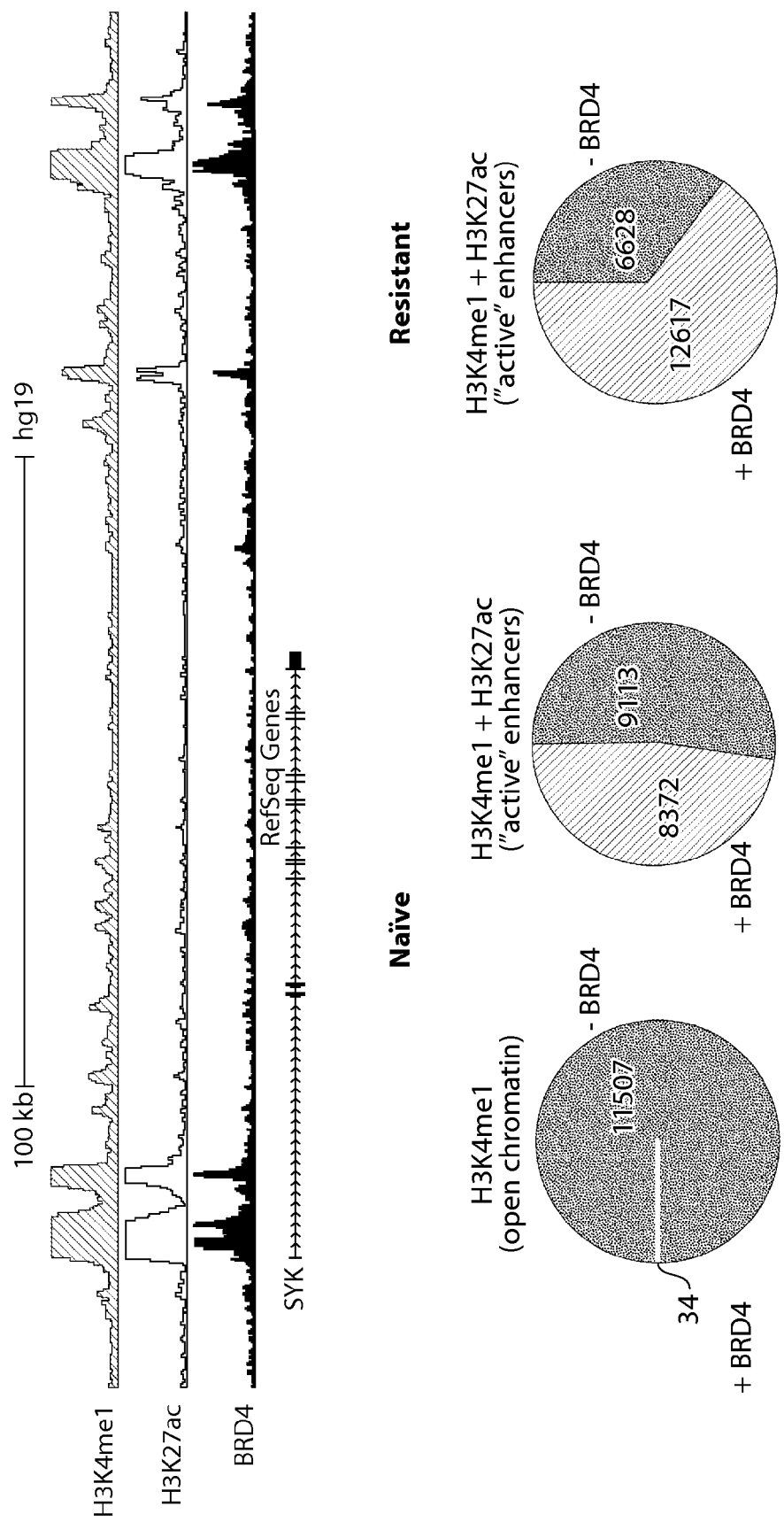
FIG. 8 is an example ChIP-SEQ readout of a genomic location where BRD4, H3K4me1, and H3K27ac all bind in the same place. Peaks indicate potential binding locations. Pie charts depict the number of "active" enhancers occupied by BRD4 in naïve and resistant leukemia cells.
Figure 9A:
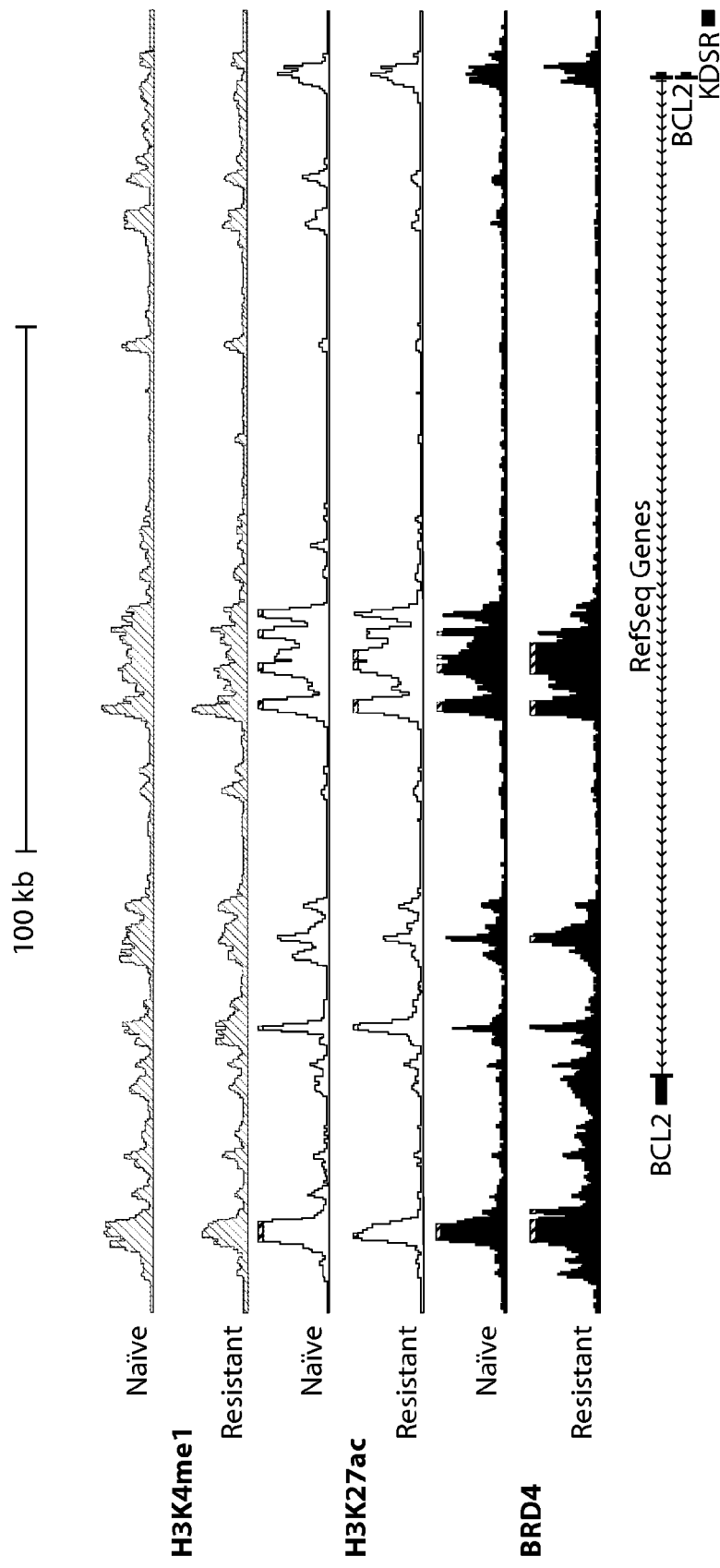
FIG. 9A is a ChIP-Seq readout of the location of BRD4, H3K4me1, and H3K27ac near the Bcl-2 gene. Peaks indicate potential binding locations.
Figure 9B:
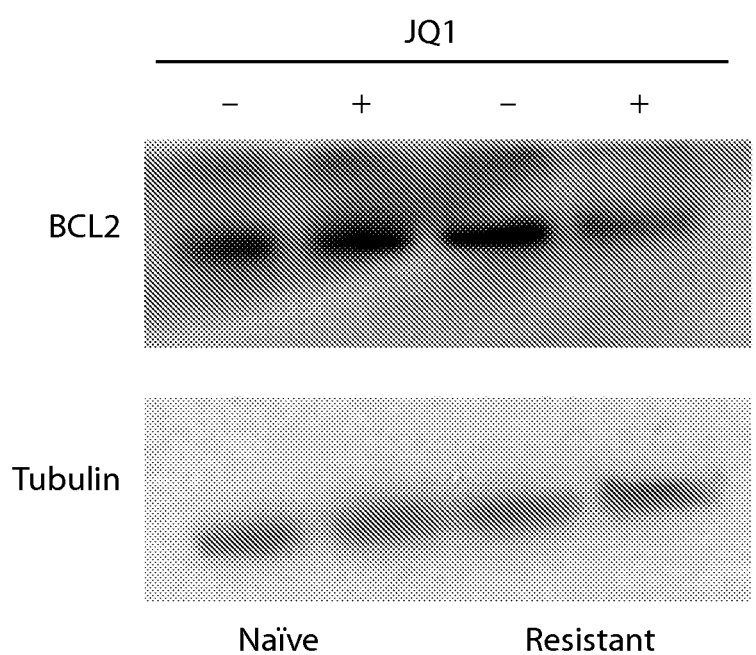
FIG. 9B is a Western blot depicting the protein levels of Bcl-2 in naïve and resistant cells treated with JQ1.

Chromatin Immunoprecipitation (ChIP) with sequencing (Seq) was performed using a BRD4 antibody to identify regions of the genome that were associated with BRD4. BRD4 was found to be associated with enhancers that were also shown to have histone marks H3K4me1 and H3K27ac (FIG. 8). Of interest, BRD4 was found to be associated with the enhancer region of BCL-2, a known anti-apoptotic gene (FIG. 9A). Bcl-2 protein was found to be upregulated in GSI resistant leukemia cells compared to naïve leukemia cells (FIG. 9B). Treatment with the bromodomain inhibitor JQ1 resulted in a decreased level of Bcl-2 protein in resistant cells (FIG. 9B).

Figure 10:
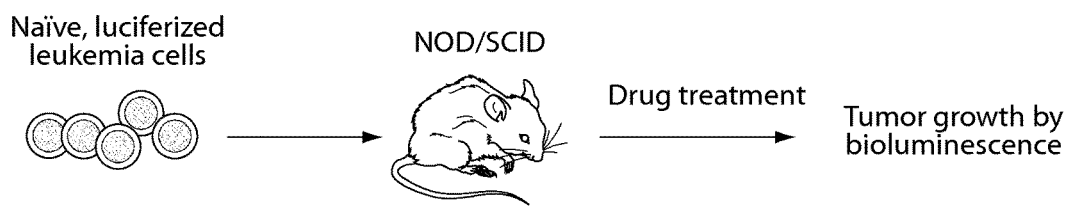
FIG. 10 is a line graph depicting the bioluminescence of luciferized leukemia cells, which is a readout of tumor burden, in mice treated with vehicle, DBZ (a GSI), JQ1, and JQ1+DBZ.
Figure 10:
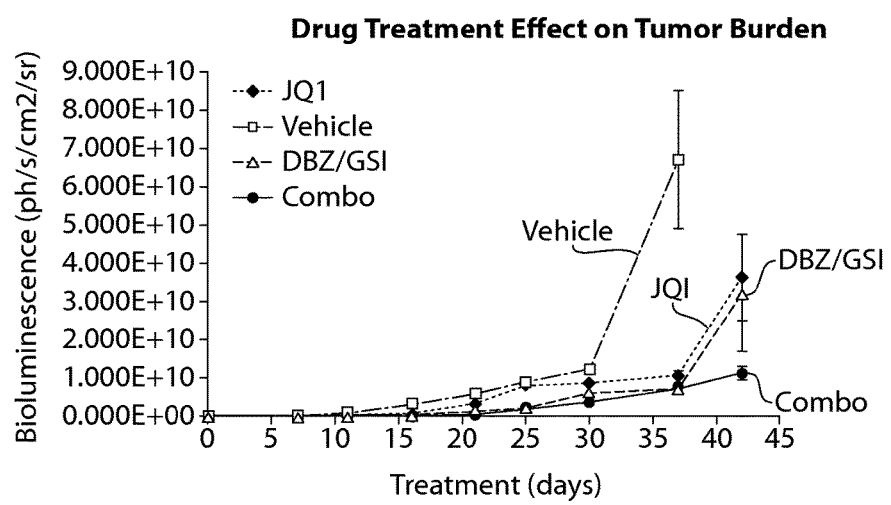
Figure 11:
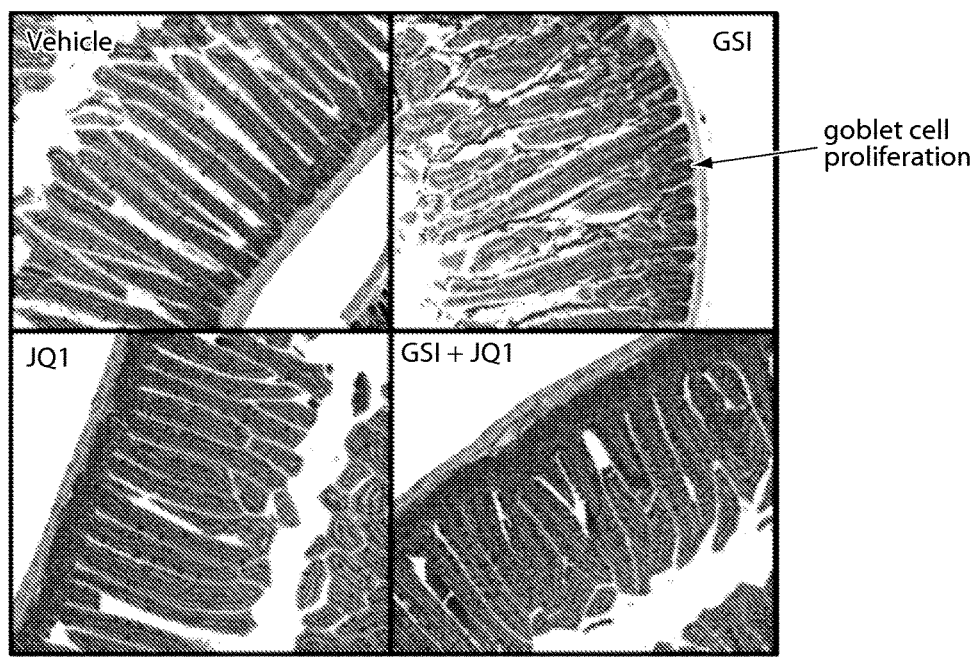
FIG. 11 is a photograph of Periodic acid-Schiff (PAS) staining of a section of the gastrointestinal tract from a mouse treated with vehicle, DBZ, JQ1, or JQ1+DBZ.

Lastly, in vivo animal studies were performed on preclinical model of T-ALL using NOD/SCID mice. Mice were injected via tail-vein with luciferized KOPTK1 cells and engraftment was monitored by bioluminescence. Following leukemia cell engraftment, mice were treated with a GSI dibenzazepine (DBZ), JQ1, DBZ+JQ1, or a vehicle control. As shown in FIG. 10, the combination of DBZ+JQ1 greatly reduced the tumor burden compared to either drug alone or the control. Additionally, side effects normally associated with GSI treatment, namely gastrointestinal damage, were reduced in normal BALB/c mice with the combination of DBZ+JQ1 compared to use of DBZ alone. Mice treated with DBZ showed significant disruption of intestinal villi architecture caused by hyperproliferation of globlet cells, as shown by Periodic acid-Schiff (PAS) stain (FIG. 11). Addition of JQ1 largely ameliorated villi architecture by partially restoring proper enterocyte differentiation.

The results indicate that bromodomain inhibitors and Bcl-2 inhibitors are a useful treatment for cancers with a Notch pathway activation mutation or cancers that are resistant to treatment with a Notch pathway inhibitor.

Example 3

Figure 12A:
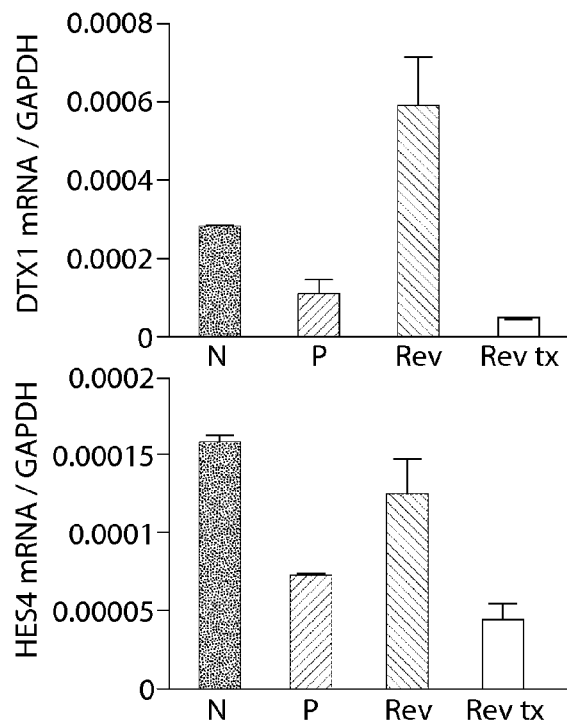
FIG. 12A is a pair of line graphs showing DTX1 and HES4 mRNA expression.
Figure 12B:
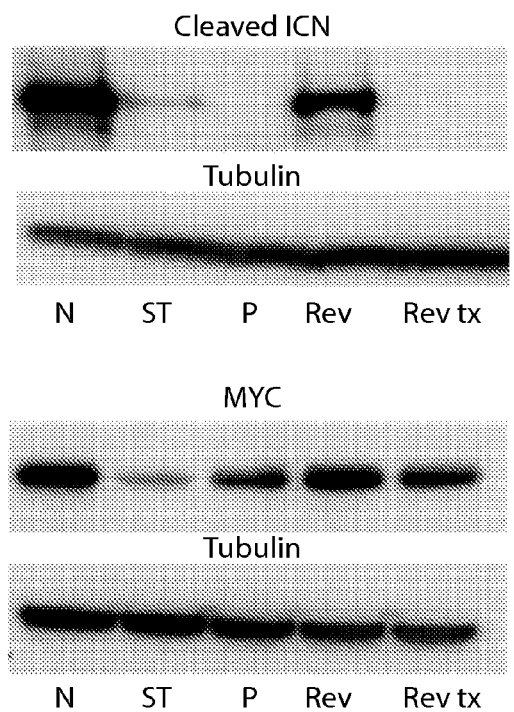
FIG. 12B is a photograph of a western blot showing expression of activated intracellular NOTCH1 (ICN) and MYC.

An Epigenetic Mechanism of Resistance to Targeted Therapy in T-cell Acute Lymphoblastic Leukemia T-ALL is an aggressive malignancy with significant rates of therapy failure that is frequently associated with activating mutations in NOTCH1, a critically important oncogene in this disease. Gamma secretase inhibitors (GSIs) that inhibit NOTCH1 cleavage and activation have been tested in clinical trials and mouse models, but responses have been modest and transient (Palomero, T. & Ferrando, A. Therapeutic targeting of NOTCH1 signaling in T-cell acute lymphoblastic leukemia. Clin Lymphoma Myeloma 9 Suppl 3, S205-210 (2009)). To understand mechanisms by which T-ALL cells overcome chronic Notch1 inhibition, GSI-resistance was modeled in vitro and in vivo, and the functional and molecular characteristics of resistant cells were investigated. When Notch-dependent T-ALL cells were treated with GSI in vitro a majority of cells stopped proliferating over the course of two weeks, but a fraction persisted and recovered their growth capacity. These 'persister' cells tolerated concentrations of GSI (compound E) more than 50-fold higher than the IC50, suggesting that they have become resistant to Notch inhibition. In order to address the mechanism of drug resistance, it was determined whether acquired resistance is fixed or reversible. It was found that, upon removal of GSI, the persisters re-express Notch target genes within a week (FIG. 12). Retreatment of these reversed cells with GSI leads to cell cycle arrest in a pattern similar to that seen for naïve T-ALL cells. Furthermore, the re-treated cells eventually acquired resistance with similar kinetics as the naïve population. The reversibility of acquired GSI tolerance in this model suggests that the resistance phenotype is mediated epigenetically.

To characterize the drug tolerant cells, the active intracellular form of NOTCH1 (ICN) (Guruharsha, K. G., Kankel, M. W. & Artavanis-Tsakonas, S. The Notch signalling system: recent insights into the complexity of a conserved pathway. Nat Rev Genet 13, 654-666 (2012)). ICN was examined and found to be present at high levels in naïve T-ALL cells, but is essentially undetectable in the persisters (FIG. 12). The persisters re-expressed ICN when GSI was removed, consistent with their reversible phenotype. Expression of Notch target genes followed a similar pattern: DTX1 and HES4 were profoundly down-regulated in the persisters (FIG. 12), but gradually recover after removal of GSI. Induction of MYC is thought to be a major mechanism by which constitutive Notch activation leads to malignancy in T-ALL (Weng, A. P. et al. c-Myc is an important direct target of Notch1 in T-cell acute lymphoblastic leukemia/lymphoma. Genes Dev 20, 2096-2109 (2006) and Palomero, T. et al. NOTCH1 directly regulates c-MYC and activates a feed-forward-loop transcriptional network promoting leukemic cell growth. Proc Natl Acad Sci USA 103, 18261-18266 (2006)). Although MYC levels are dramatically reduced by short term GSI treatment, expression of this oncoprotein recovers modestly in the persisters (FIG. 12). Nonetheless, gene expression profiles indicated that the persisters had lost the predominating MYC transcriptional signature of naïve T-ALL cells. These data suggest that the persisters had acquired the ability to proliferate in the absence of Notch signaling, but maintained modest MYC activity through alternative means.

Figure 13:
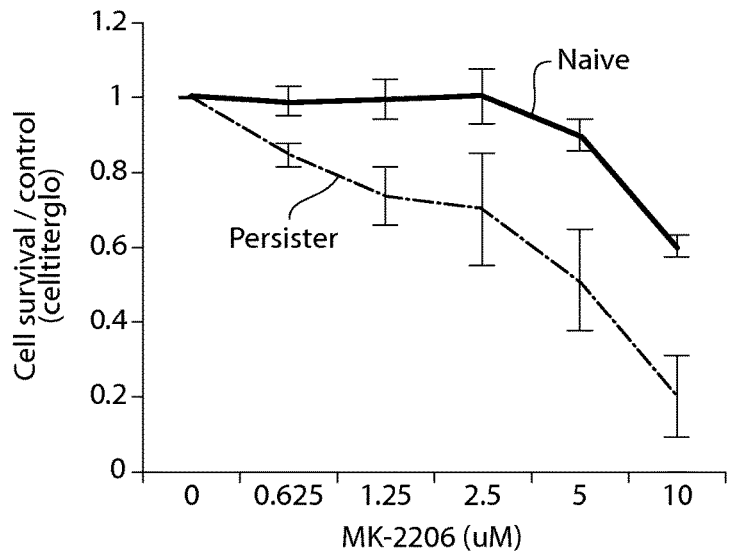
FIG. 13 is a line graph depicting cell proliferative response to the AKT inhibitor MK-2206 in naïve and persister cells.
Figure 14:
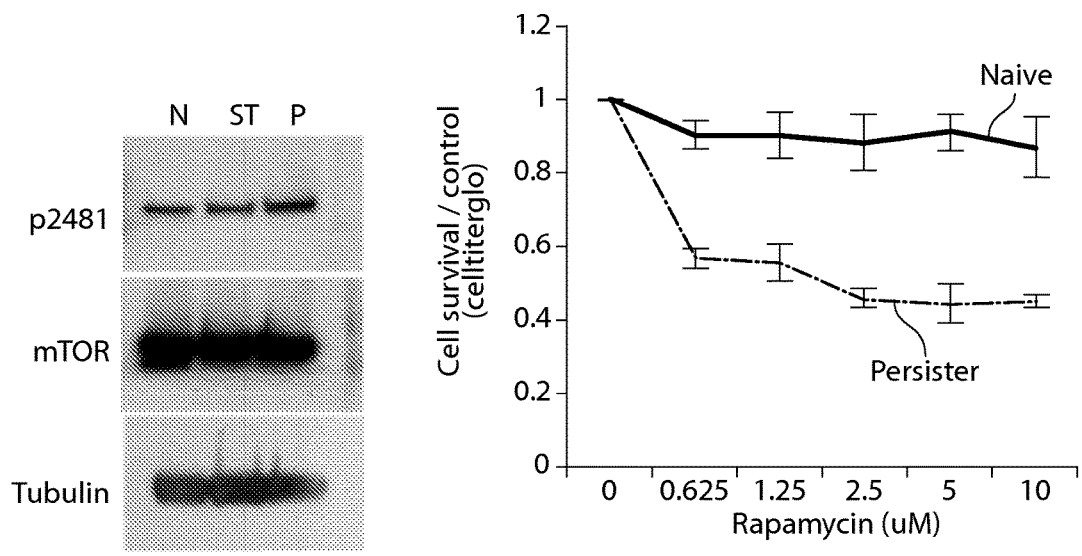
FIG. 14 shows a western blot of Phospho-mTOR (p2481), a marker of activated mTOR signaling, total mTOR and Tubulin for naïve (N), short-term treated (ST) and persister (R) cells and a line graph depicting cell proliferative response to Rapamycin in naïve and persister cells.

In contrast to the reduced MYC signature, gene expression profiles revealed enhanced signatures for MAPK, JNK, PI3K and MTOR signaling in the persisters. Genetic alterations of PTEN resulting in increased AKT pathway activity have been associated with Notch resistance (Gutierrez, A. et al. High frequency of PTEN, PI3K, and AKT abnormalities in T-cell acute lymphoblastic leukemia. Blood 114, 647-650 (2009) and Palomero, T. et al. Mutational loss of PTEN induces resistance to NOTCH1 inhibition in T-cell leukemia. Nat Med 13, 1203-1210 (2007)). Although the T-ALL cell lines modeled here do not harbor PTEN mutations, the persisters have increased levels of phosphorylated PTEN and, accordingly, are more sensitive to treatment with an AKT inhibitor (FIG. 13). mTOR has been demonstrated to be active in leukemia, including Notch-dependent T-ALL (Chan, S. M., Weng, A. P., Tibshirani, R., Aster, J. C. & Utz, P. J. Notch signals positively regulate activity of the mTOR pathway in T-cell acute lymphoblastic leukemia. Blood 110, 278-286 (2007) and Kalaitzidis, D. et al. mTOR complex 1 plays critical roles in hematopoiesis and Pten-loss-evoked leukemogenesis. Cell Stem Cell 11, 429-439 (2012)). The persisters showed increased levels of the phosphorylated form p2481 of mTOR and sensitivity to the mTOR inhibitor Rapamycin (FIG. 14). These alterations in cytoplasmic signaling were accompanied by changes in the metabolic profiles indicative of a shift from a predominantly glycolytic state in naïve T-ALL cells to a greater reliance on oxidative phosphorylation in the persisters (FIG. 2). These data suggest that rewired signaling and metabolic programs in the persister cells are critical for proliferation in the absence of Notch signaling.

Figure 3C:
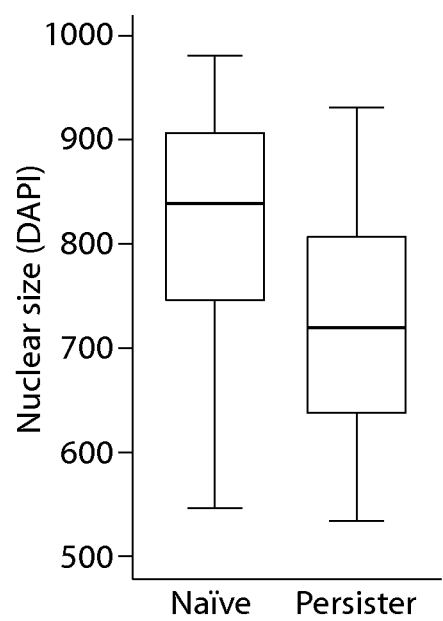
FIG. 3C is a bar graph showing nuclear size (by DAPI) for naïve and persister cells.

The persistence phenotype was also notable for morphologic changes, including a profound decrease in cell and nuclear size, which was reversible after removal of GSI (FIGS. 3A-C). It was postulated that these changes might reflect global chromatin compaction associated with exposure and subsequent tolerance to Notch inhibition. In support of this view, it was found that the persisters up-regulate heterochromatin-associated HP1 proteins and have high global levels of repressive chromatin modifications (FIG. 4A). To evaluate global compaction more directly, chromatin was digested from naïve and persister cells with micrococcal nuclease. It was found that chromatin in the persisters is relatively inaccessible and has a longer average nucleosomal repeat length indicative of linker histone H1 incorporation (FIG. 4B), as is consistent with a more compact chromatin state. Recent links drawn between metabolism and chromatin regulation (Lu, C. & Thompson, C. B. Metabolic regulation of epigenetics. Cell Metab 16, 9-17 (2012)) prompted evaluation of the relationships between metabolic changes and chromatin compaction. It was found that glucose restriction led to increased chromatin compaction in naïve T-ALL cells. It was also found that chromatin compaction was an early consequence of Notch inhibition, with rapid up-regulation of HP1 protein expression upon GSI exposure (FIG. 4A). The functional significance of chromatin state changes in T-ALL persister cells was then investigated further.

First, histone modifications were profiled in naïve and persister T-ALL cells by ChIP-seq. Marks associated with promoters (H3K4me3), transcripts (H3K36me3), enhancers (H3K4me1, H3K27ac) and Polycomb-repressed loci (H3K27me3) were surveyed (Zhou, V. W., Goren, A. & Bernstein, B. E. Charting histone modifications and the functional organization of mammalian genomes. Nat Rev Genet 12, 7-18 (2011) and Dunham, I. et al. An integrated encyclopedia of DNA elements in the human genome. Nature 489, 57-74 (2012)). Striking differences in chromatin state were evident within loci encoding Notch target genes, including CD300A and DELTEX1. Promoter, transcript and enhancer chromatin signals in these loci were markedly reduced in the persisters, consistent with reduced gene expressions[17]. Conversely, chromatin activity was increased within certain loci, such as MAP3K5, that are induced in the persisters. In addition, the persisters exhibited a modest increase in H3K27me3 levels over euchromatic loci and a reduction in bulk H3K27ac levels (FIG. 5A). Thus, acquisition of GSI tolerance is associated with focal chromatin changes at differentially-regulated loci and a genome-wide reduction of accessible euchromatin.

Figure 15:
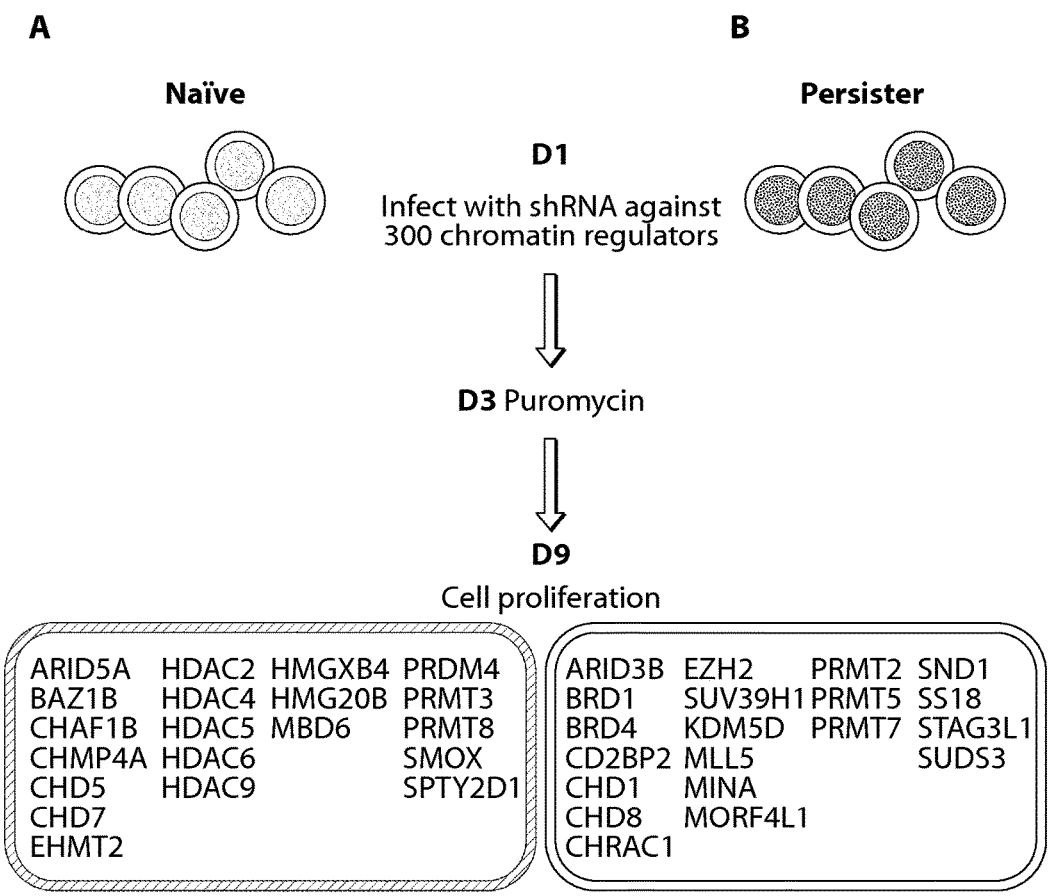
FIG. 15 is a graphical depiction of the shRNA screen for chromatin regulators preferentially required for naïve or persister cell survival. Top hits for each cell state are shown in boxes (left box and right box, naïve and persister cells, respectively).

It was postulated that their altered chromatin state might uncover new susceptibilities in the persister cells that could be targeted by emerging epigenetic therapies. To test this, a lentiviral short-hairpin RNA (shRNA) knockdown screen was designed that targeted ~350 chromatin regulators with an average of 5 independent hairpins per gene (FIG. 15). About 15 genes were identified for which knockdown compromised survival in both naïve and persister cells, and thus presumed to be generally required for T-ALL cells. Riger analysis was then used to identify genes preferentially required for survival of either naïve or persister cells. Naïve cells were found to be preferentially dependent on several histone deactylase (HDACs) enzymes, while the persister cells showed a greater dependence on other genes, including several arginine methyltransferases (FIG. 15). The chromatin regulatory proteins identified for the persister cells include: ARID3B, EZH2, PRMT2, SND1, BRD1, SUV39H1, PRMT5, SS18, BRD4, KDM5D, PRMT7, STAG3L1, CD2BP2, MLL5, SUDS3, CHD1, MINA, CHD8, MORF4L1, or CHRAC1. The gene name and transcript IDs provided in Table 8 can be used to identify the shRNA sequences used by searching the RNAi Consortium (TRC) Portal (Broad Institute, Cambridge, Mass.).

TABLE 8

Chromatin Regulatory Proteins for which the persister cells showed a greater dependence

| GENE NAME | GENE ID | TRANSCRIPT ID | PROTEIN ID |
| --- | --- | --- | --- |
| ARID3B | ENSG00000179361 | ENST00000346246, ENST00000566147, ENST00000563567, ENST00000569680, ENST00000566468 | ENSP00000343126, ENSP00000455668 |
| EZH2 | ENSG00000106462 | ENST00000483967, ENST00000320356, ENST00000478654, ENST00000476773, ENST00000460911, ENST00000350995, ENST00000536783, ENST00000541220, ENST00000492143, ENST00000483012, ENST00000498186, ENST00000469631 | ENSP00000419856, ENSP00000320147, ENSP00000417062, ENSP00000419050, ENSP00000419711, ENSP00000223193, ENSP00000439305, ENSP00000443219, ENSP00000417377, ENSP00000417704 |

TABLE 8-continued

Chromatin Regulatory Proteins for which the persister cells showed a greater dependence

| GENE NAME | GENE ID | TRANSCRIPT ID | PROTEIN ID |
|---|---|---|---|
| PRMT2 | ENSG00000160310 | ENST00000355680 | ENSP00000347906 |
| | | ENST00000334494 | ENSP00000335490 |
| | | ENST00000397637 | ENSP00000380759 |
| | | ENST00000397638 | ENSP00000380760 |
| | | ENST00000455177 | ENSP00000406127 |
| | | ENST00000397628 | ENSP00000380752 |
| | | ENST00000440086 | ENSP00000397266 |
| | | ENST00000291705 | ENSP00000291705 |
| | | ENST00000451211 | ENSP00000411984 |
| | | ENST00000458387 | ENSP00000407463 |
| | | ENST00000498151 | |
| | | ENST00000491389 | |
| | | ENST00000482508 | |
| | | ENST00000481861 | |
| | | ENST00000486520 | |
| SND1 | ENSG00000197157 | ENST00000354725, | ENSP00000346762, |
| | | ENST00000486037, | ENSP00000419327 |
| | | ENST00000461056, | |
| | | ENST00000468621, | |
| | | ENST00000483503, | |
| | | ENST00000492772, | |
| | | ENST00000468166, | |
| | | ENST00000465900, | |
| | | ENST00000467238, | |
| | | ENST00000470723, | |
| | | ENST00000470463, | |
| | | ENST00000485871, | |
| | | ENST00000484767, | |
| | | ENST00000492840, | |
| | | ENST00000489417, | |
| | | ENST00000463020 | |
| BRD1 | ENSG00000100425 | ENST00000542442, | ENSP00000437514, |
| | | ENST00000457780, | ENSP00000410042, |
| | | ENST00000438393, | ENSP00000388027, |
| | | ENST00000419212, | ENSP00000399110, |
| | | ENST00000404760, | ENSP00000385858, |
| | | ENST00000404034, | ENSP00000384076, |
| | | ENST00000342989, | ENSP00000345886, |
| | | ENST00000216267 | ENSP00000216267 |
| SUV39H1 | ENSG00000101945 | ENST00000376687, | ENSP00000365877, |
| | | ENST00000337852, | ENSP00000337976, |
| | | ENST00000453214, | ENSP00000410686 |
| | | ENST00000482260, | |
| | | ENST00000462786 | |
| PRMT5 | ENSG00000100462 | ENST00000324366, | ENSP00000319169, |
| | | ENST00000397440, | ENSP00000380582, |
| | | ENST00000557443, | ENSP00000452501, |
| | | ENST00000397441, | ENSP00000380583, |
| | | ENST00000216350, | ENSP00000216350, |
| | | ENST00000553897, | ENSP00000452555, |
| | | ENST00000553550, | ENSP00000450737, |
| | | ENST00000554910, | ENSP00000452411, |
| | | ENST00000553502, | ENSP00000450956, |
| | | ENST00000556043, | ENSP00000452509, |
| | | ENST00000555530, | ENSP00000452409, |
| | | ENST00000555454, | ENSP00000451245, |
| | | ENST00000454731, | ENSP00000387663, |
| | | ENST00000421938, | ENSP00000409482, |
| | | ENST00000556616, | ENSP00000450919, |
| | | ENST00000554867, | ENSP00000452218, |
| | | ENST00000538452, | ENSP00000444915, |
| | | ENST00000556426, | ENSP00000451127, |
| | | ENST00000553915, | ENSP00000450633, |
| | | ENST00000557415, | ENSP00000452102 |
| | | ENST00000553787, | |
| | | ENST00000476175, | |
| | | ENST00000554716, | |
| | | ENST00000553641, | |
| | | ENST00000557015, | |
| | | ENST00000557758, | |
| | | ENST00000553417, | |
| | | ENST00000556032 | |
| SS18 | ENSG00000141380 | ENST00000269137, | ENSP00000269137, |
| | | ENST00000542420, | ENSP00000438066, |
| | | ENST00000415083, | ENSP00000414516, |

TABLE 8-continued

Chromatin Regulatory Proteins for which the persister cells showed a greater dependence

| GENE NAME | GENE ID | TRANSCRIPT ID | PROTEIN ID |
|---|---|---|---|
| | | ENST00000581021, | ENSP00000463586, |
| | | ENST00000584083, | ENSP00000463943, |
| | | ENST00000579061, | ENSP00000462766, |
| | | ENST00000539849, | ENSP00000444647, |
| | | ENST00000542743, | ENSP00000444551, |
| | | ENST00000545952, | ENSP00000443097, |
| | | ENST00000579640, | ENSP00000462363, |
| | | ENST00000585121, | ENSP00000462838, |
| | | ENST00000539244, | ENSP00000441760, |
| | | ENST00000269138, | ENSP00000269138, |
| | | ENST00000582448, | ENSP00000464609, |
| | | ENST00000578700, | ENSP00000464673, |
| | | ENST00000577572, | ENSP00000463802, |
| | | ENST00000578954, | ENSP00000464664, |
| | | ENST00000581570, | ENSP00000464556, |
| | | ENST00000582792, | ENSP00000463928, |
| | | ENST00000580751, | ENSP00000464049, |
| | | ENST00000580642, | ENSP00000462104, |
| | | ENST00000577636, | ENSP00000463933 |
| | | ENST00000577751, | |
| | | ENST00000583595, | |
| | | ENST00000578595, | |
| | | ENST00000585241, | |
| | | ENST00000582092, | |
| | | ENST00000580003, | |
| | | ENST00000580958 | |
| BRD4 | ENSG00000141867 | ENST00000371835, | ENSP00000360901, |
| | | ENST00000360016, | ENSP00000353112, |
| | | ENST00000263377 | ENSP00000263377 |
| KDM5D | ENSG00000012817 | ENST00000317961, | ENSP00000322408, |
| | | ENST00000382806, | ENSP00000372256, |
| | | ENST00000447300, | ENSP00000416377, |
| | | ENST00000440077, | ENSP00000398543, |
| | | ENST00000415360, | ENSP00000389433, |
| | | ENST00000535647, | ENSP00000445530, |
| | | ENST00000541639, | ENSP00000444293 |
| | | ENST00000492117, | |
| | | ENST00000469599, | |
| | | ENST00000485154, | |
| | | ENST00000478891 | |
| PRMT7 | ENSG00000132600 | ENST00000339507, | ENSP00000343103, |
| | | ENST00000563562, | ENSP00000455238, |
| | | ENST00000449359, | ENSP00000414716, |
| | | ENST00000565745, | ENSP00000456190, |
| | | ENST00000566657, | ENSP00000454980, |
| | | ENST00000569571, | ENSP00000455538, |
| | | ENST00000569047, | ENSP00000456848, |
| | | ENST00000348497, | ENSP00000345775, |
| | | ENST00000441236, | ENSP00000409324, |
| | | ENST00000568975, | ENSP00000454776, |
| | | ENST00000562050, | ENSP00000457381, |
| | | ENST00000566341, | ENSP00000455705, |
| | | ENST00000562381 | ENSP00000456364 |
| STAG3L1 | ENSG00000205583 | ENST00000404291, | |
| | | ENST00000487154, | |
| | | ENST00000402225, | |
| | | ENST00000456374, | |
| | | ENST00000338421 | |
| | | ENST00000339898, | |
| | | ENST00000436837, | |
| CD2BP2 | ENSG00000169217 | ENST00000305596, | ENSP00000304903, |
| | | ENST00000569466, | ENSP00000456935 |
| | | ENST00000564525 | |
| MLL5 | ENSG00000005483 | ENST00000311117, | ENSP00000312379, |
| | | ENST00000476671, | ENSP00000417888, |
| | | ENST00000473063, | ENSP00000417156, |
| | | ENST00000495267, | ENSP00000420415, |
| | | ENST00000478990, | ENSP00000419883, |
| | | ENST00000474203, | ENSP00000420206, |
| | | ENST00000257745, | ENSP00000257745, |
| | | ENST00000334877, | ENSP00000335599, |
| | | ENST00000334914, | ENSP00000333986, |
| | | ENST00000334884, | ENSP00000335398, |
| | | ENST00000482560, | ENSP00000417193, |
| | | ENST00000478079, | ENSP00000419525 |

TABLE 8-continued

Chromatin Regulatory Proteins for which the persister cells showed a greater dependence

| GENE NAME | GENE ID | TRANSCRIPT ID | PROTEIN ID |
|---|---|---|---|
| SUDS3 | ENSG00000111707 | ENST00000480368, ENST00000485619, ENST00000468607, ENST00000496191, ENST00000479838 ENST00000543473, ENST00000397564, ENST00000541591, ENST00000541280, ENST00000360286 | ENSP00000443988, ENSP00000380695 |
| CHD1 | ENSG00000153922 | ENST00000284049, ENST00000512844, ENST00000505657, ENST00000511067, ENST00000514344, ENST00000512392, ENST00000511628, ENST00000513064, ENST00000508756, ENST00000414220, ENST00000505982 | ENSP00000284049, ENSP00000422589, ENSP00000422225 |
| MINA | ENSG00000170854 | ENST00000394198, ENST00000333396, ENST00000360258, ENST00000507612, ENST00000503097, ENST00000506099, ENST00000330299, ENST00000514314, ENST00000506682, ENST00000503517 | ENSP00000377748, ENSP00000328251, ENSP00000353395, ENSP00000424530, ENSP00000421347, ENSP00000423816, ENSP00000327424, ENSP00000424955 |
| CHD8 | ENSG00000100888 | ENST00000430710, ENST00000557364, ENST00000553622, ENST00000555935, ENST00000553283, ENST00000553870, ENST00000399982, ENST00000553651, ENST00000555962, ENST00000556833, ENST00000557727, ENST00000557329, ENST00000554384, ENST00000555301 | ENSP00000406288, ENSP00000451601, ENSP00000450957, ENSP00000451442, ENSP00000450860, ENSP00000451071, ENSP00000382863 |
| MORF4L1 | ENSG00000185787 | ENST00000331268, ENST00000426013, ENST00000559345, ENST00000379535, ENST00000560422, ENST00000559690, ENST00000559158, ENST00000559930, ENST00000559244, ENST00000559751, ENST00000558746, ENST00000558830, ENST00000558502, ENST00000559697, ENST00000558539, ENST00000561171, ENST00000558893, ENST00000558522, ENST00000559258, ENST00000557961, ENST00000559619, ENST00000558923, ENST00000560710 | ENSP00000331310, ENSP00000408880, ENSP00000452717, ENSP00000368850, ENSP00000453625, ENSP00000453351, ENSP00000453432, ENSP00000454191, ENSP00000454030, ENSP00000453972, ENSP00000453231, ENSP00000453738, ENSP00000452808 |
| CHRAC1 | ENSG00000104472 | ENST00000220913, ENST00000519533, ENST00000518971, ENST00000519618, ENST00000523569 | ENSP00000220913, ENSP00000428697, ENSP00000430484, ENSP00000430003 |

BRD4 was identified as a top hit in the screen, with 3 shRNAs significantly reducing persister cell proliferation without affecting the naïve population. BRD4 is a member of the BET family of bromodomains that selectively bind acetylated histones and mediate epigenetic gene regulation (Dawson, M. A. & Kouzarides, T. Cancer epigenetics: from mechanism to therapy. Cell 150, 12-27 (2012) and Zhao, R., Nakamura, T., Fu, Y., Lazar, Z. & Spector, D. L. Gene bookmarking accelerates the kinetics of post-mitotic transcriptional re-activation. Nat Cell Biol 13, 1295-1304 (2011)). BRD4 has been implicated in several malignancies, including acute myeloid leukemia and lymphoma (Blobel, G. A., Kalota, A., Sanchez, P. V. & Carroll, M. Short hairpin RNA screen reveals bromodomain proteins as novel targets in acute myeloid leukemia. Cancer Cell 20, 287-288 (2011) and Zuber, J. et al. RNAi screen identifies Brd4 as a therapeutic target in acute myeloid leukemia. Nature 478, 524-528 (2011)). It was confirmed that the shRNAs silence BRD4 at protein levels and also replicated their selective effect on persister cell survival. The exquisite dependency of GSI tolerant persister cells on BRD4 is of particular interest given the recent development of small molecule BET inhibitors, such as JQ1 (Filippakopoulos, P. et al. Selective inhibition of BET bromodomains. Nature 468, 1067-1073 (2010) and Nicodeme, E. et al. Suppression of inflammation by a synthetic histone mimic. Nature 468, 1119-1123 (2010)). Indeed, it was found that the persisters undergo proliferation arrest in response to JQ1 concentrations that are well tolerated by naïve T-ALL cells (FIG. 7), whereas a JQ1 enantiomer had no effect. Thus, chromatin state changes in the persister cells are accompanied by markedly increased sensitivity to inhibition of BRD4, a 'reader' of acetylated chromatin.

Figure 16B:
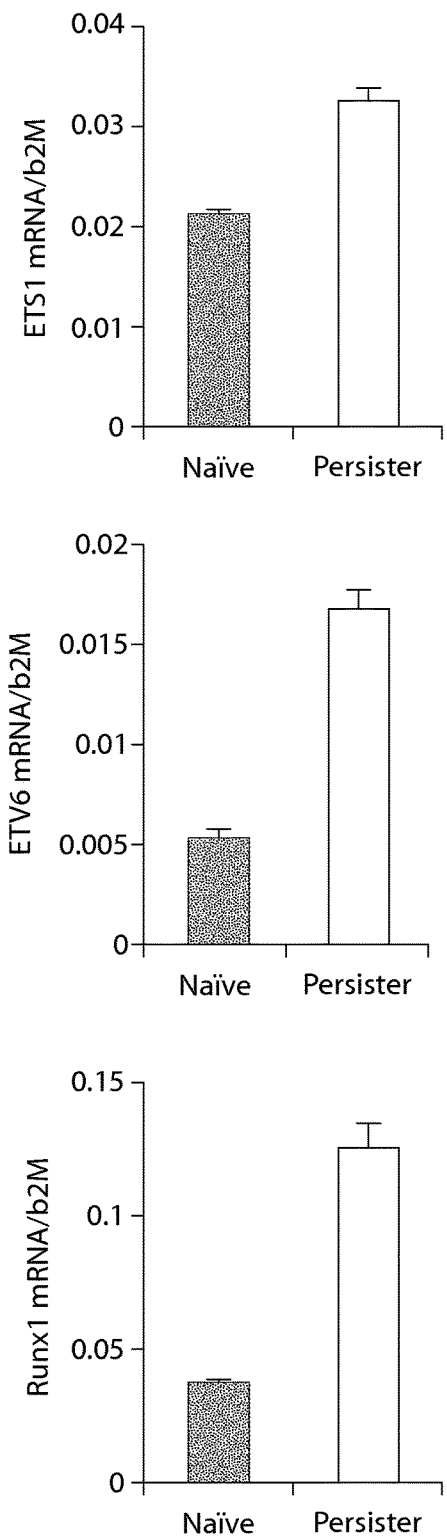
FIG. 16B shows mRNA levels of ETS1, ETV6, and Runx1 in naïve and persister cells.

To investigate its regulatory functions, BRD4 was mapped genome-wide in persister cells. BRD4 bound mainly to promoters (~30% of sites) and putative enhancers enriched for H3K4me1 and H3K27ac (~60%), consistent with its biochemical affinity for acetylated histones. In contrast, sites of open chromatin marked exclusively by H3K4me1 were rarely bound by BRD4. BRD4-bound enhancers were enriched near genes with functions related to phosphoprotein signaling (539/989 genes; 53%), including many in the AKT and mTOR pathways. The binding sites were also found to be enriched for consensus motifs for ETS family and RUNX transcription factors (FIG. 16). Consistently, RT-PCR revealed increased expression of ETS1, ETV6 and RUNX1 in the persister cells (FIG. 16B). Our analysis suggests that BRD4 mediates gene regulatory programs required for the proliferation of drug tolerant T-ALL cells. The global chromatin compaction in the persister cells may render enhancers and their gene targets particularly reliant on BRD4 for their epigenetic maintenance.

Figure 17A:
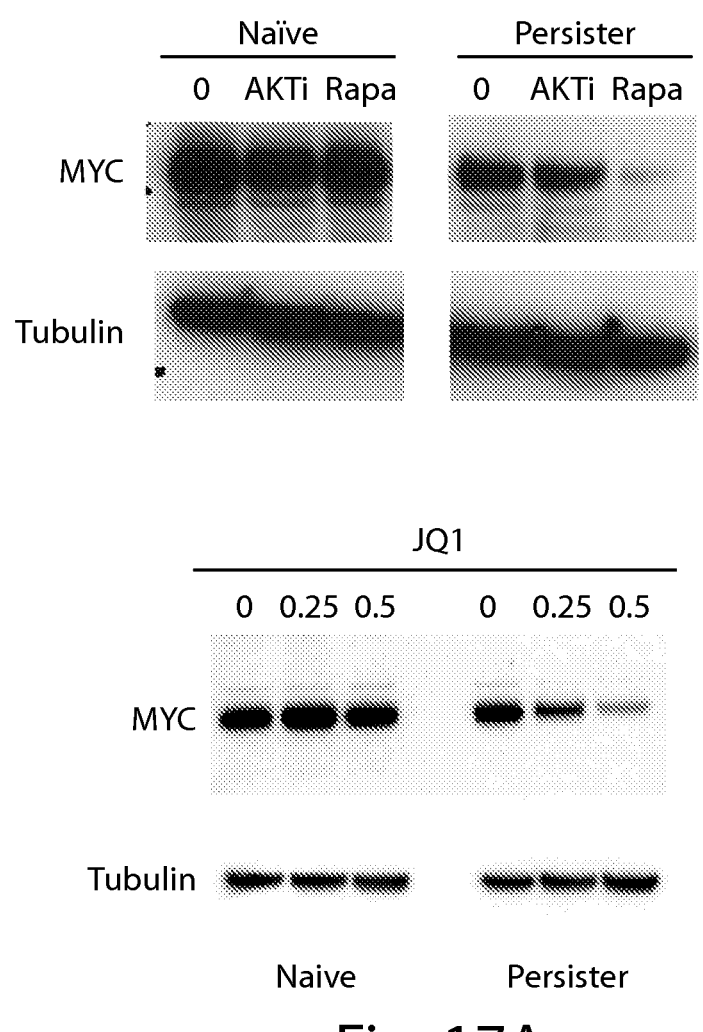
FIG. 17A is two photographs of western blots show MYC expression in naïve and persister cells after 3 day treatment with 2 µM AKT inhibitor, MK-2206, or 10 nM mTOR inhibitor, Rapamycin.
Figure 17B:
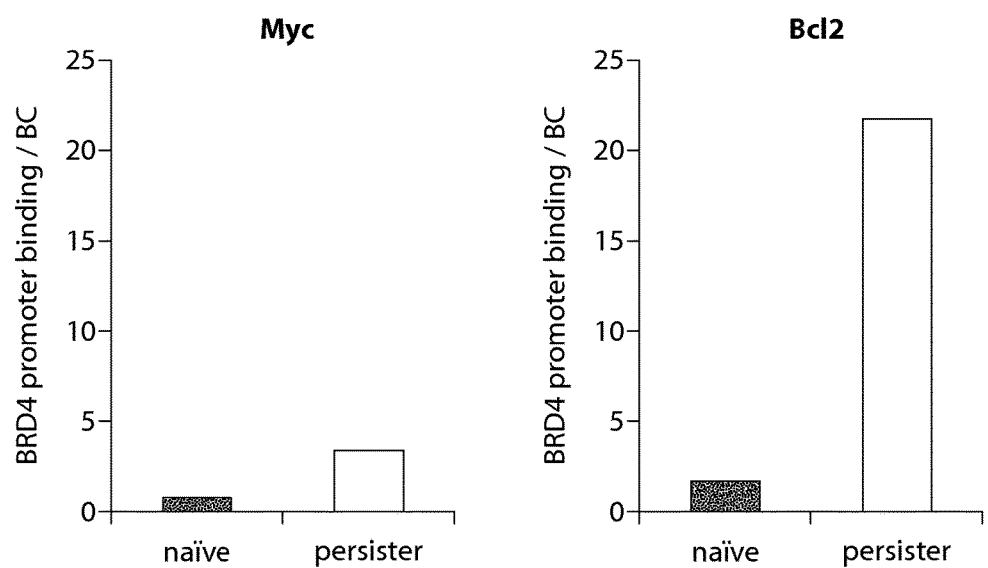
FIG. 17B depicts graphs showing BRD4 binding at the MYC and BCL2 promoters.

Next, individual genes that might account for the BRD4 dependency of the persister cells were examined. MYC was focused on first, as it is a known BRD4 target (Filippakopoulos, P. et al. Selective inhibition of BET bromodomains. Nature 468, 1067-1073 (2010)), whose expression is sustained in the persister cells, albeit at a lower level compared to the naïve. It was postulated that increased AKT and mTOR signaling might maintain MYC expression in these cells. Indeed, a small molecule inhibitor of the mTOR pathway markedly reduce MYC expression in persister cells, but have essentially no effect in naïve cells (FIG. 17A). BRD4 bound several putative enhancers in the MYC locus (FIG. 17B). JQ1 significantly reduced MYC expression in the persisters at doses that did not alter MYC in naïve cells (FIG. 17A). Thus, altered mechanisms of MYC activation appear to sensitize persister cells to BRD4 inhibition.

Figure 18A:
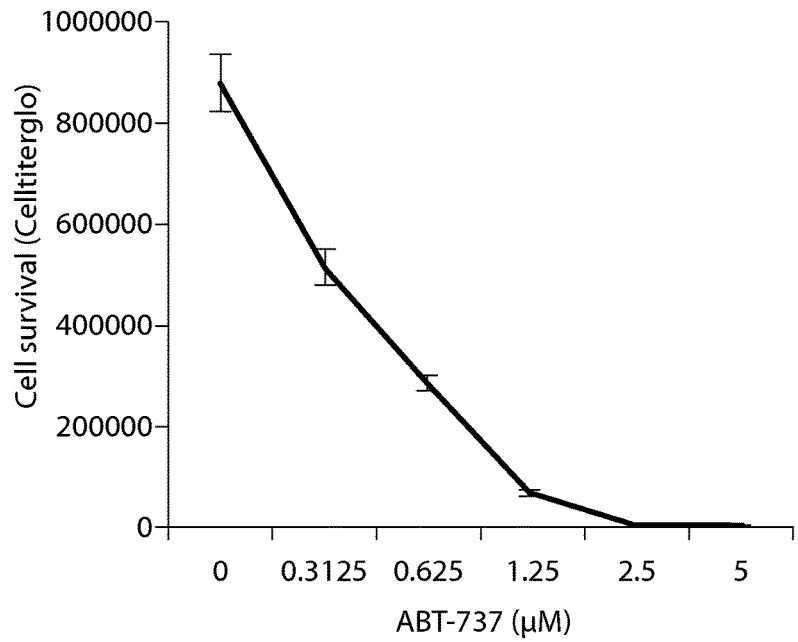
FIG. 18A is a line graph showing the proliferative response of persister cells after 6 days of treatment with the Bcl-2 inhibitor ABT-737.
Figure 18B:
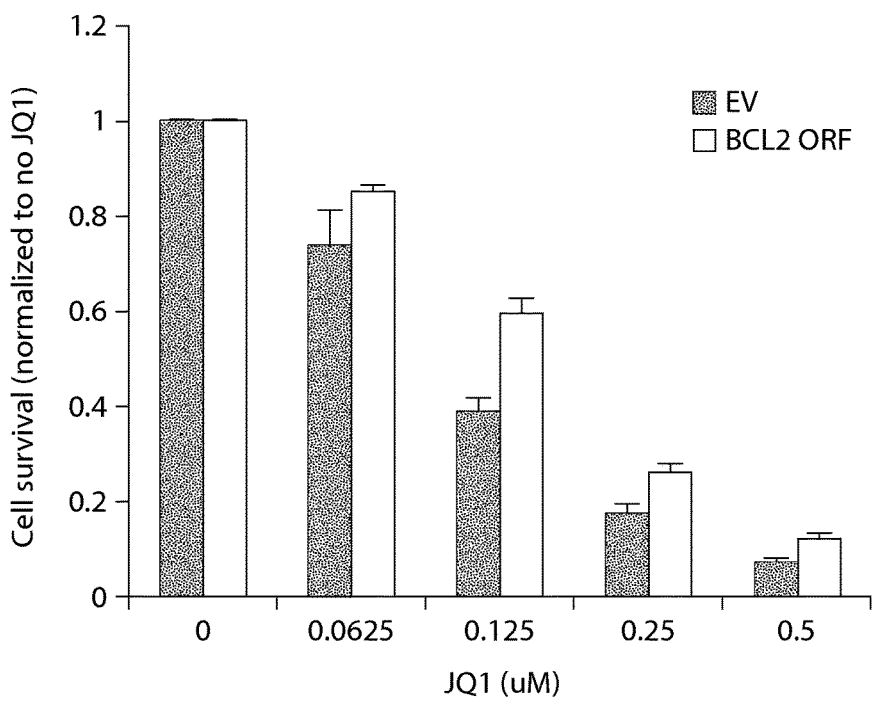
FIG. 18B is a bar graph depicting the proliferative response of persister cells transfected with Bcl-2 expression vector (or empty vector control) after 6 days of treatment with JQ1.

The anti-apoptosis regulator BCL2 is an established BRD4-dependent gene in mixed lineage leukemia (Dawson, M. A. et al Inhibition of BET recruitment to chromatin as an effective treatment for MLL-fusion leukemia. Nature 478, 529-533 (2011)). Intense BRD4 binding is evident throughout the BCL2 locus (FIGS. 9A and 17B), which is highly expressed in the drug tolerant T-ALL cells. JQ1 treatment significantly reduced Bcl-2 expression in these cells, but had little effect on the naïve population (FIG. 9B). It was reasoned that loss of Bcl-2 might account for the apoptosis seen in persisters treated with JQ1 (FIG. 7). In support of this model, the Bcl-2 inhibitor ABT-737 effectively killed persister cells (FIG. 18A). Furthermore, Bcl-2 over-expression partially rescues persister cells from JQ1 treatment (FIG. 18B). Hence, down-regulation of this survival gene is critical for JQ1-induced cell death in drug tolerant T-ALL cells.

Figure 19A:
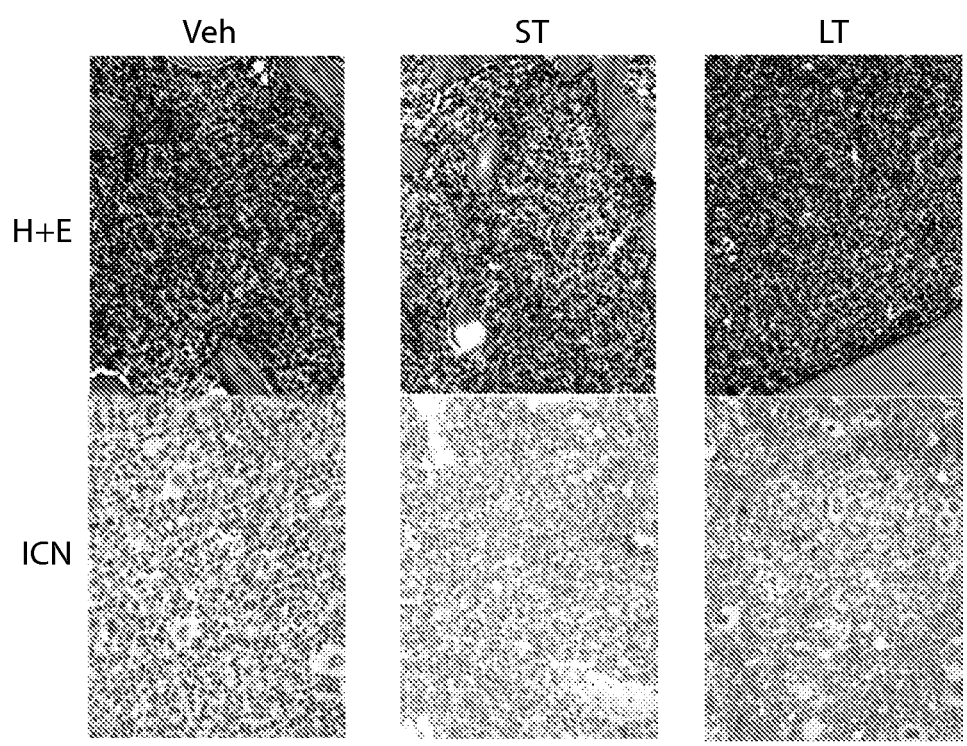
FIG. 19A is a series of photographs depicting hematoxylin and eosin (H&E) stains and immunohistochemistry for activated Notch (ICN) for bone marrow from leukemic mice treated with Notch inhibitor DBZ for 5 days (ST) or 3 weeks (LT) or treated with vehicle (Veh).
Figure 19B:
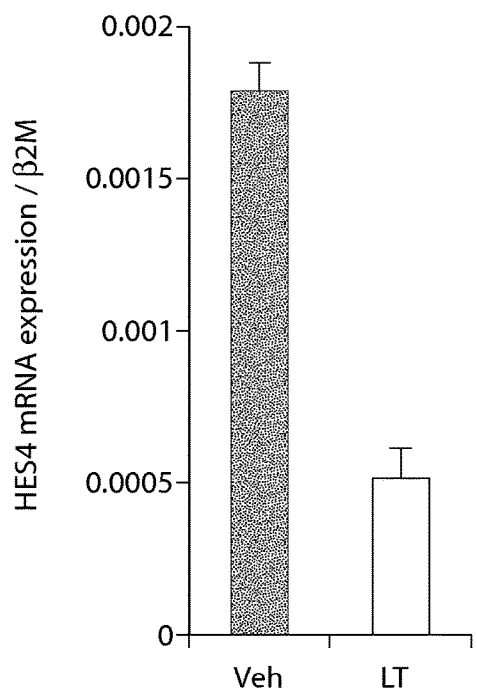
FIG. 19B is a series of bar graphs showing levels of HES4, DTX1, HP1γ, and Bcl-2 for leukemia cells sorted from spleens of vehicle (Veh) or long-term (LT) treated mice.
Figure 19B:
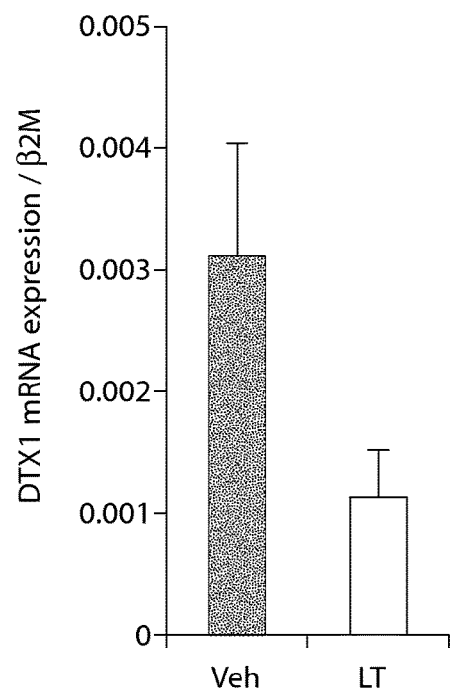
Figure 19B:
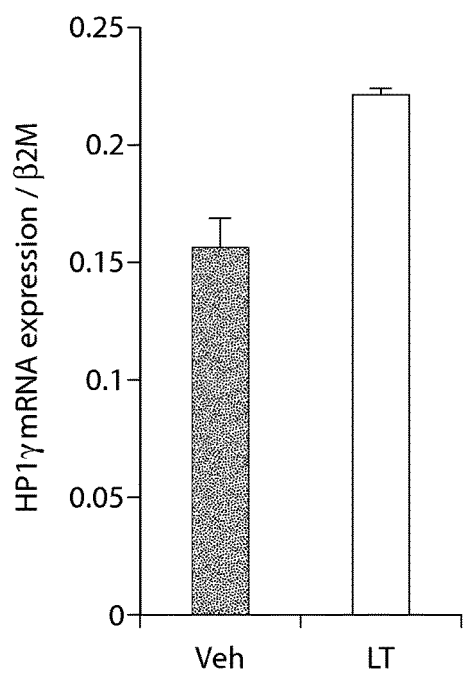
Figure 19B:
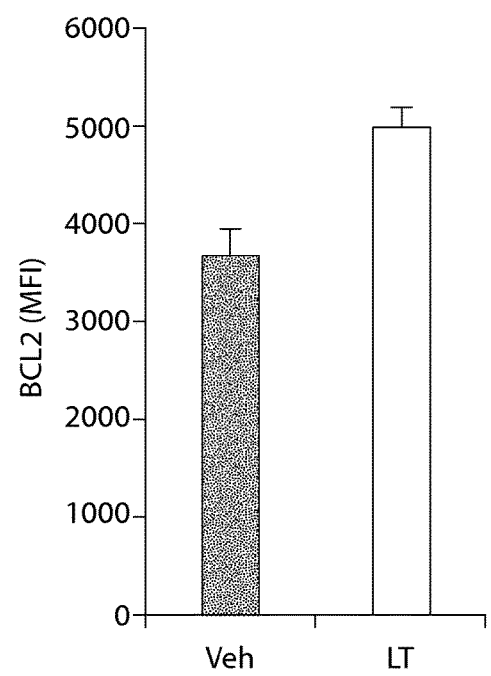
Figure 20:
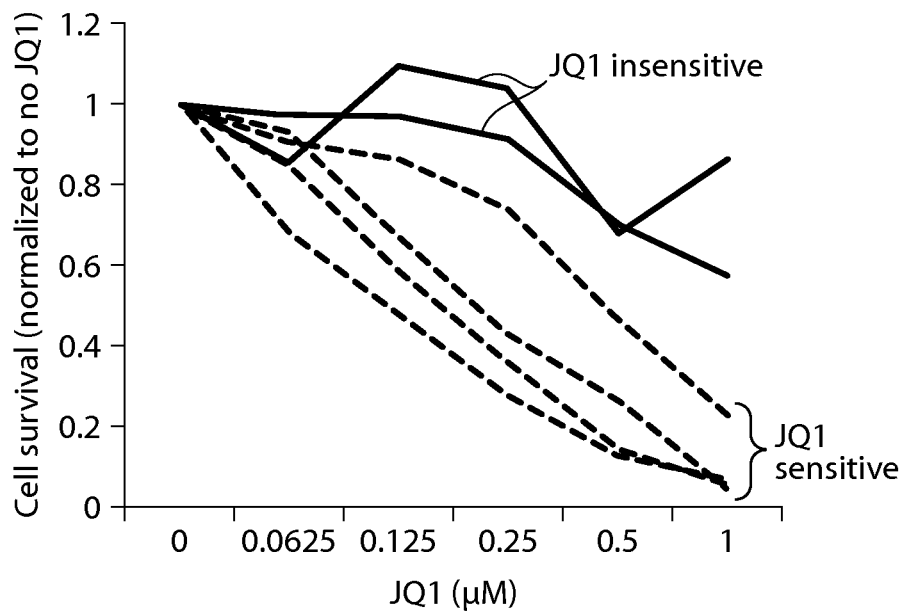
FIG. 20 is a pair of graphs depicting the level of CD1d in in vitro naïve and persister cells. The left graph shows expression of CD in naïve or persister populations. The right graph depicts quantification of CD1d expression for clones originating from single naïve cells that proliferated in the presence of GSI (n=7) or control conditions (n=7)(p<0.002).
Figure 20:
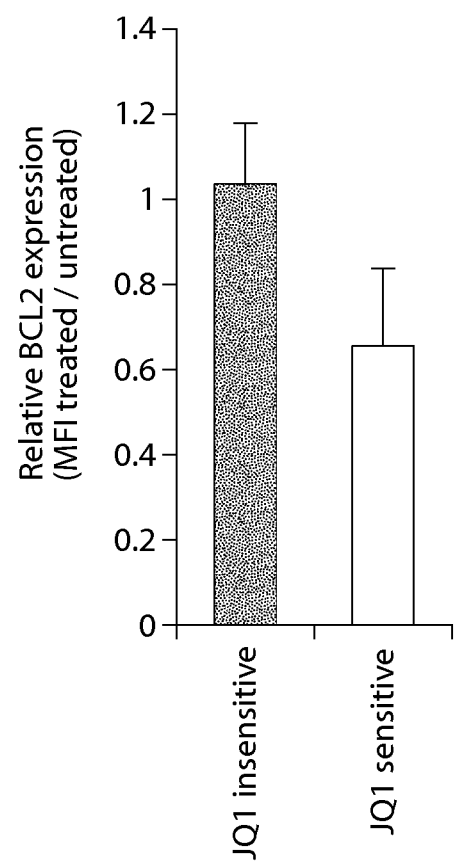

To investigate the in vivo relevance of the GSI resistance and associated epigenetic changes, KOPT-K1 T-ALL cells with a mcherry marker were injected orthotopically into NOD-SCID mice and the bioluminescence was followed over time. GSI resistance developed rapidly in vivo after a short period of slowed tumor growth. ICN levels were drastically reduced in bone marrow of GSI-treated mice and Notch target genes were down-regulated in the corresponding leukemia cells, indicating that resistance is not due to Notch reactivation (FIG. 19A). The 'in vivo persisters' also share other phenotypic characteristics with their in vitro counterparts, including increased HP1γ, Bcl-2 and CD52 expression and decreased CD1d expression, suggestive of a common mechanism (FIG. 19B). Primary T-ALL cells were also examined for their sensitivity to the combination of GSI and JQ1. Growth arrest was observed in two-thirds of cases, and this was associated with marked reduction in BCL2 expression (FIG. 20). These data support the in vivo relevance of GSI drug tolerance and a shared mechanism of BET inhibitor sensitivity in primary T-ALL.

Figure 21:
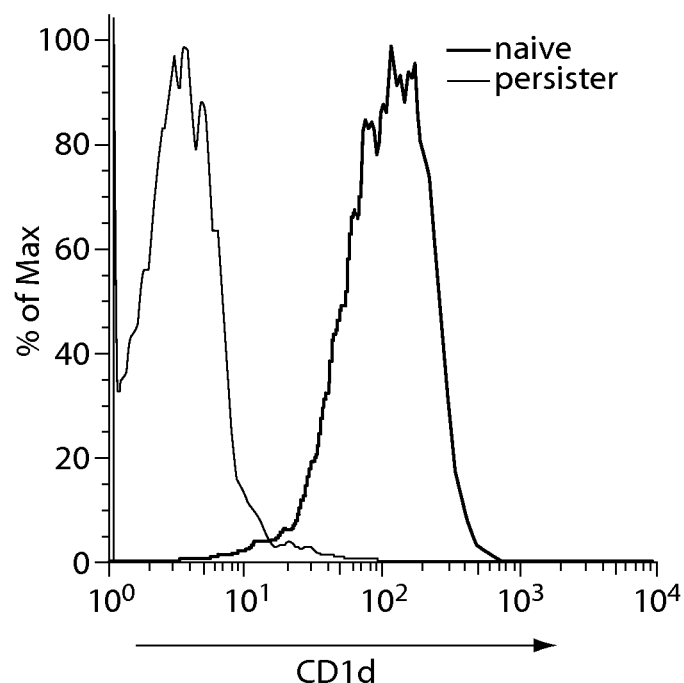
FIG. 21 is a pair of graphs depicting data from primary human T-ALL cells. The left graph shows the proliferative response of primary human T-ALL cells from 6 different patients after 5 days of treatment with 1 micromolar GSI and the indicated JQ1 doses, relative to no JQ1 control. The right graphs shows the relative expression of intracellular BCL2 measured by flow cytometry in primary T-ALL cells after 3 days of treatment with 1 micromolar GSI and 0.5 micromolar JQ1, normalized to untreated.
Figure 21:
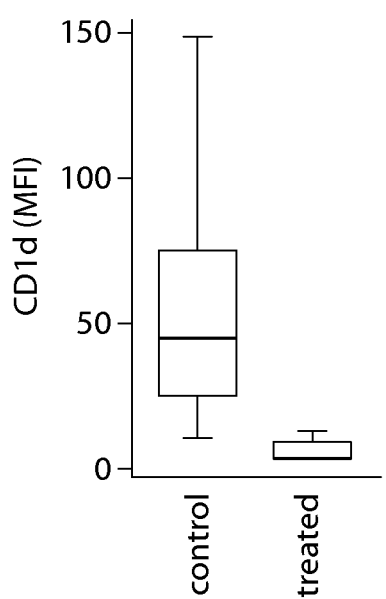

Finally, the population level dynamics of naïve T-ALL cells exposed to GSI were considered. The initial response to drug appears relatively homogeneous, with near complete loss of activated Notch, rapid chromatin compaction and a marked reduction in the size distribution of the population. However, striking cell-to-cell variability was observed in terms of the efficiency with which naïve cells acquire resistance. Specifically, when single cell clones were isolated and treated with GSI, it was found that ~3% of clones in the starting population could resume growth in the presence of drug. The single cell persister clones shared phenotypic markers with persisters derived by treating naïve T-ALL populations (FIG. 21). The reversibility of the persister phenotype indicates that these clones are distinguished by epigenetic as opposed to genetic alterations. This suggests that while Notch inhibition elicits a relatively uniform response, GSI resistance may depend on a pre-existing population of epigenetically distinct T-ALL cells able to engage requisite resistance mechanisms.

Therapeutic resistance plagued early GSI trials in humans (Palomero, T. & Ferrando, A. Therapeutic targeting of NOTCH1 signaling in T-cell acute lymphoblastic leukemia. Clin Lymphoma Myeloma 9 Suppl 3, S205-210 (2009)) and is a major challenge in cancer treatment today, pertinent to conventional chemotherapy and targeted therapy alike (Haber, D. A., Gray, N. S. & Baselga, J. The evolving war on cancer. Cell 145, 19-24 (2011)). As shown herein, T-ALL cells can acquire GSI resistance by a fully reversible epigenetic mechanism reminiscent of a previously established model of drug tolerant lung cancer cells (Sharma, S. V. et al. A chromatin-mediated reversible drug-tolerant state in cancer cell subpopulations. Cell 141, 69-80 (2010)). GSI resistance in T-ALL is mediated through rewired signaling and metabolic pathways, and a dramatic chromatin state transition that uncovers a new therapeutic sensitivity to BET inhibition. The data shown herein suggests that the heightened sensitivity of persister cells to BET inhibition reflects a stringent requirement for BRD4 to sustain the activity of distal gene enhancers, as is consistent with previously established bookmarking functions at promoters (Zhao, R., Nakamura, T., Fu, Y., Lazar, Z. & Spector, D. L. Gene bookmarking accelerates the kinetics of post-mitotic transcriptional re-activation. Nat Cell Biol 13, 1295-1304 (2011)). The study described herein provides a framework for understanding epigenetic alterations that underlie tumor pathogenesis, and suggests the potential of combination therapy that incorporates new classes of epigenetic therapies as a means to avert resistance phenotypes.

Without further elaboration, it is believed that one skilled in the art can, based on the above description, utilize the present invention to its fullest extent. The specific embodiments are, therefore, to be construed as merely illustrative, and not limitative of the remainder of the disclosure in any way whatsoever. All publications, patent application, and patents cited herein are incorporated by reference for the purposes or subject matter referenced herein.

The indefinite articles "a" and "an," as used herein in the specification and in the claims, unless clearly indicated to the contrary, should be understood to mean "at least one."

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method comprising administering to a subject having cancer a bromodomain inhibitor, with or without a Bcl-2 inhibitor, and a Notch pathway inhibitor, in an effective amount to treat the cancer, wherein the cancer is characterized by the presence of a Notch pathway activation mutation.

2. The method of claim 1, wherein the bromodomain inhibitor, without the Bcl-2 inhibitor, and the Notch pathway inhibitor are administered.

3. The method of claim 1, wherein the bromodomain inhibitor, the Bcl-2 inhibitor and the Notch pathway inhibitor are administered.

4. The method of claim 3, wherein the bromodomain inhibitor, the Bcl-2 inhibitor and the Notch pathway inhibitor are administered concurrently or sequentially.

5. The method of claim 1, further comprising identifying the subject as a subject having cancer characterized by the presence of a Notch pathway activation mutation.

6. The method of claim 2, wherein the bromodomain inhibitor and the Notch pathway inhibitor are administered concurrently or sequentially.

7. The method of claim 3, wherein the bromodomain inhibitor and the Bcl-2 inhibitor are administered concurrently or sequentially.

8. The method of claim 3, wherein the Bcl-2 inhibitor is G3139, GX15-070, ABT-737 or ABT-199.

9. The method of claim 1, wherein the bromodomain inhibitor is a BET inhibitor.

10. The method of claim 1, wherein the bromodomain inhibitor is JQ1 or a derivative thereof.

11. The method of claim 1, wherein the Notch pathway inhibitor is a gamma secretase inhibitor.

12. The method of claim 3, wherein the bromodomain inhibitor, the Bcl-2 inhibitor and/or the Notch pathway inhibitor is an siRNA, shRNA, or antisense nucleic acid molecule.

* * * * *